United States Patent
Prakash et al.

(10) Patent No.: US 11,260,073 B2
(45) Date of Patent: Mar. 1, 2022

(54) COMPOUNDS AND METHODS FOR MODULATING C9ORF72

(71) Applicants: IONIS PHARMACEUTICALS, INC., Carlsbad, CA (US); BOARD OF REGENTS OF THE UNIVERSITY OF TEXAS SYSTEM, Austin, TX (US)

(72) Inventors: Thazha P. Prakash, Carlsbad, CA (US); Frank Rigo, Carlsbad, CA (US); David Corey, Dallas, TX (US)

(73) Assignees: IONIS PHARMACEUTICALS, INC., Carlsbad, CA (US); BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/772,805

(22) PCT Filed: Nov. 2, 2016

(86) PCT No.: PCT/US2016/060106
§ 371 (c)(1),
(2) Date: May 1, 2018

(87) PCT Pub. No.: WO2017/079291
PCT Pub. Date: May 11, 2017

(65) Prior Publication Data
US 2018/0318330 A1    Nov. 8, 2018

Related U.S. Application Data

(60) Provisional application No. 62/249,833, filed on Nov. 2, 2015.

(51) Int. Cl.
| | | |
|---|---|---|
| *C07H 21/04* | (2006.01) | |
| *A61K 31/712* | (2006.01) | |
| *A61K 31/7125* | (2006.01) | |
| *C12N 15/113* | (2010.01) | |
| *C12Q 1/6883* | (2018.01) | |
| *A61K 31/7115* | (2006.01) | |
| *A61P 21/00* | (2006.01) | |
| *A61P 25/28* | (2006.01) | |
| *A61K 48/00* | (2006.01) | |

(52) U.S. Cl.
CPC ........ *A61K 31/712* (2013.01); *A61K 31/7115* (2013.01); *A61K 31/7125* (2013.01); *A61K 48/0066* (2013.01); *A61P 21/00* (2018.01); *A61P 25/28* (2018.01); *C12N 15/113* (2013.01); *C12Q 1/6883* (2013.01); *C12N 2310/113* (2013.01); *C12N 2310/14* (2013.01); *C12N 2310/345* (2013.01); *C12N 2310/346* (2013.01); *C12Q 2600/178* (2013.01)

(58) Field of Classification Search
USPC ......................................................... 536/24.5
See application file for complete search history.

(56) References Cited

U.S. PATENT DOCUMENTS

| | | |
|---|---|---|
| 5,801,154 A | 9/1998 | Baracchini et al. |
| 5,998,148 A | 12/1999 | Bennett et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel et al. |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 7,759,478 B1 | 7/2010 | Bentwich et al. |
| 8,501,805 B2 | 8/2013 | Seth et al. |
| 8,530,640 B2 | 9/2013 | Seth et al. |
| 8,546,556 B2 | 10/2013 | Seth et al. |
| 8,927,513 B2* | 1/2015 | Manoharan ............ C07H 19/11 514/44 A |
| 9,012,421 B2 | 4/2015 | Migawa et al. |
| 9,605,263 B2 | 3/2017 | Rigo |
| 9,896,729 B2 | 2/2018 | Pickering-Brown et al. |
| 9,963,699 B2 | 5/2018 | Bennett et al. |
| 10,066,228 B2* | 9/2018 | Linsley ............... C07F 9/65616 |
| 10,138,482 B2 | 11/2018 | Rigo |
| 10,221,414 B2 | 3/2019 | Freier et al. |
| 10,443,052 B2 | 10/2019 | Freier |
| 10,577,604 B2 | 3/2020 | Bennett et al. |

(Continued)

FOREIGN PATENT DOCUMENTS

| | | |
|---|---|---|
| EP | 1752536 | 2/2007 |
| WO | WO 2016/050822 | 4/1916 |

(Continued)

OTHER PUBLICATIONS

Mori et al. (Acta Neuropathol 2013:126: 881-893).*
Kurreck, Jens. "Antisense technologies: improvement through novel chemical modifications." *European Journal of Biochemistry* 270.8 (2003): 1628-1644.
"The ALS Association and the Packard Center Partner to Develop Animal Model Systems for Most Common Cause of Familial ALS", http://www.alsa.org/news/archive/new-animal-model-systems.html Mar. 1, 2012 (printed Oct. 23, 2015).
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — Kimberly Chong
(74) *Attorney, Agent, or Firm* — Parker Highlander PLLC

(57) ABSTRACT

Disclosed herein are compounds and methods for modulating C9orf72 transcript. Such compounds and methods are useful to treat, prevent, or ameliorate neurodegenerative diseases in an individual in need thereof.

35 Claims, 4 Drawing Sheets
Specification includes a Sequence Listing.

(56) References Cited

U.S. PATENT DOCUMENTS

| | | |
|---|---|---|
| 2001/0053519 A1 | 12/2001 | Fodor et al. |
| 2003/0228597 A1 | 12/2003 | Cowsert et al. |
| 2004/0038274 A1 | 2/2004 | Cook et al. |
| 2004/0171570 A1 | 9/2004 | Allerson et al. |
| 2004/0181048 A1 | 9/2004 | Wang |
| 2005/0130923 A1 | 6/2005 | Bhat et al. |
| 2006/0003322 A1 | 1/2006 | Bentwich et al. |
| 2007/0031844 A1 | 2/2007 | Khvorova et al. |
| 2008/0039618 A1 | 2/2008 | Allerson et al. |
| 2009/0012281 A1 | 1/2009 | Swayze et al. |
| 2010/0216864 A1 | 8/2010 | Staarup et al. |
| 2012/0149757 A1 | 6/2012 | Krainer et al. |
| 2012/0214865 A1 | 8/2012 | Bennett et al. |
| 2013/0035366 A1 | 2/2013 | Swayze et al. |
| 2014/0255936 A1 | 9/2014 | Rademakers |
| 2014/0303238 A1 | 10/2014 | Linsley et al. |
| 2015/0148404 A1 | 5/2015 | de Visser et al. |
| 2015/0259679 A1* | 9/2015 | Bennett ............. C12N 15/113 514/44 A |
| 2015/0267197 A1 | 9/2015 | Bennett et al. |
| 2016/0024496 A1 | 1/2016 | Bennett et al. |
| 2016/0108396 A1 | 4/2016 | Jensen et al. |
| 2016/0251655 A1 | 9/2016 | Freier et al. |
| 2016/0304871 A1 | 10/2016 | Rigo |
| 2017/0349897 A1 | 12/2017 | Rigo |
| 2019/0092618 A1 | 5/2019 | Bennett et al. |
| 2019/0142856 A1 | 5/2019 | Bennett et al. |
| 2019/0264204 A1 | 8/2019 | Rigo |
| 2019/0367916 A1 | 12/2019 | Freier et al. |
| 2021/0230589 A1 | 7/2021 | Rigo |

FOREIGN PATENT DOCUMENTS

| | | |
|---|---|---|
| WO | WO 2018/064600 | 4/1918 |
| WO | WO 1996/014329 | 5/1996 |
| WO | WO 1998/039352 | 9/1998 |
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2005/040180 | 5/2005 |
| WO | WO 2005/044981 | 5/2005 |
| WO | WO 2005/113016 | 12/2005 |
| WO | WO 2005/121368 | 12/2005 |
| WO | WO 2007/056113 | 5/2007 |
| WO | WO 2007/089584 | 8/2007 |
| WO | WO 2007/131237 | 11/2007 |
| WO | WO 2007/134181 | 11/2007 |
| WO | WO 2007/146511 | 12/2007 |
| WO | WO 2008/076324 | 6/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/007855 | 1/2009 |
| WO | WO 2009/049166 | 4/2009 |
| WO | WO 2009/060124 | 5/2009 |
| WO | WO 2010/019270 | 2/2010 |
| WO | WO 2010/148013 | 12/2010 |
| WO | WO 2011/005793 | 1/2011 |
| WO | WO 2011/135396 | 11/2011 |
| WO | WO 2012/005898 | 1/2012 |
| WO | WO 2012/012443 | 1/2012 |
| WO | WO 2012/012467 | 1/2012 |
| WO | WO 2012/087983 | 6/2012 |
| WO | WO 2012/092367 | 7/2012 |
| WO | WO 2012/135736 | 10/2012 |
| WO | WO 2013/030588 | 3/2013 |
| WO | WO 2013/036833 | 3/2013 |
| WO | WO 2013/075079 | 5/2013 |
| WO | WO 2013/082548 | 6/2013 |
| WO | WO 2013/086207 | 6/2013 |
| WO | WO 2013/173608 | 11/2013 |
| WO | WO 2014/062686 | 4/2014 |
| WO | WO 2014/062691 | 4/2014 |
| WO | WO 2014/062736 | 4/2014 |
| WO | WO 2014/114660 | 7/2014 |
| WO | WO 2015/054676 | 4/2015 |
| WO | WO 2015/057727 | 4/2015 |
| WO | WO 2015/057738 | 4/2015 |
| WO | WO 2016/024205 | 2/2016 |
| WO | WO 2016/060919 | 4/2016 |
| WO | WO 2016/168592 | 10/2016 |
| WO | WO 2017/079291 | 5/2017 |
| WO | WO 2017/180835 | 10/2017 |

OTHER PUBLICATIONS

Altmann et al., "Second Generation Antisense Oligonucleotides-Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nucleosides & Nucleotides. (1997) 16:917-926.

Altmann et al., "Second Generation of Antisense Oligonucleotides: From Nuclease Resistance to Biological Efficacy in Animals " Chimia (1996) 50(4):168-176.

Altmann et al., "Second-generation antisense oligonucleotides: structure-activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Al-Sarraj et al., "p62 positive, TDP-43 negative, neuronal cytoplasmic and intranuclear inclusions in the cerebellum and hippocampus define the pathology of C9orf72-linked FTLD and MND/ALS" Acta Neuropathol (2011) 122:691-702.

Ash et al., "Unconventional Translation of C9ORF72 GGGGCC Expansion Generates Insoluble Ploypeptides Specific to c9FTD/ALS" Neuron (2013) 77(4): 639-646.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Baloh, R.H, "Generation of Non-Integrating iPS Cells and Motor Neurons from C9orf72 Repeat Expansion ALS Patients" 65th AAN Annual Meeting, San Diego, CA, Mar. 16-23, 2013.

Baloh, R.H., "Targeting RNA foci shows a therapeutic effect in iPSC-derived motor neurons from C9orf72 repeat patients" ALSMND meeting, Milan, Dec. 6, 2013.

Baloh, R.H., "Induced Pluripotent stem cell models from C9orf72 patients." Oral presentation, California ALS PAC10 Research Summit, Los Angeles, CA, Nov. 11, 2012.

Baughn et al., "Antisense Oligonucleotide as a Potential Therapy for Amyotrophic Lateral Sclerosis with C9orf72 Expansion" Poster Presentation, Keystone Symposia, New Frontiers in Neurodegenerative Disease Research, Santa Fe, NM, Feb. 3-8, 2013.

Baughn et al, "Sense and Anti-Sense RNA Foci in c9ALS/FTD: More Light in a House of Mirrors" Annals of Neurology (Oct. 14, 2013) 74(17): p. S60.

Bennett et al., "Antisense oligonucleotides as a tool for gene functionalization and target validation," Biochimica et Biophysica Acta (1999) 1489: 19-30.

Bieniek et al., "Tau pathology in frontotemporal lobar degeneration with C9ORF72 hexanucleotide repeat expansion" Acta Neuropathol (2013) 125(2):289-302.

Boxer et al. "Clinical, neuroimaging and neuropathological features of a new chromosome 9p-linked FTD-ALS family" J. Neurol. Neurosurg. Psychiatry (2011) 82:196-203.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brettschneider et al., "Microglial activation correlates with disease progression and upper motor neuron clinical symptoms in Amyotrophic Lateral Sclerosis", PLOS ONE (2012) 7:e39216.

Chin "On the Preparation and Utilization of Isolated and Purified Oligonucleotides" Document purportedly located on a CD-ROM

(56) References Cited

OTHER PUBLICATIONS and contributed to the public collection of the Katherine R. Everett Law Library of the University of North Carolina on Mar. 14, 2002.
Chio et al., "Prevalence of SOD1 mutations in the Italian ALS population" Neurology (2008) 70:533-537.
Crooke et al., "Basic Principles of Antisense Therapeutics" Antisense Research and Application (1998) Chapter 1:1-50.
Dejesus-Hernandez et al., "Expanded GGGGCC Hexanucleotide Repeat in Noncoding Region of C9ORF72 Causes Chromosome 9p-Linked FTD and ALS" Neuron (2011) 72:245-256.
Donnelly et al., "Development of a C9ORF72 ALS antisense therapy and a therapeutic biomarker" Abstracts of the Society for Neuroscience, Washington, DC, US, Oct. 17, 2012, Retrieved from the Internet Aug. 15, 2016: http://www.abstractsonline.com/Plan/ViewAbstract.aspx?sKey=c4cccfd5-5e4c-4d1e-9569-9a1b1eb21d80&cKev=c5c69155-5d2b-467c-8d1f-87299c514c7f&mKey=%7b70007181-01C9-4DE9-A0A2-EEBFA14CD9F1%7d.
Donnelly et al., "Development of C9ORF72 ALS Biomarkers and Therapeutics" American Neurological Association 2012 Annual Meeting, Poster Presentation, Boston, MA Oct. 10, 2012.
Donnelly et al., "Development of C9orf72 ALS Biomarkers and Therapeutics" Annals of Neurology (Oct. 10, 2012) 72(16):S67-S68.
Donnelly et al., "Limited availability of ZBP1 restricts axonal mRNA localization and nerve regeneration capacity" EMBO J. (2011) 30:4665-4677.
Donnelly et al., "RNA toxicity from the ALS/FTD C9ORF72 expansion is mitigated by antisense intervention" Neuron (2013) 80(2):415-428.
Donnelly et al., "Transcriptome analysis of C9orf72 ALS patient derived CNS iPS cells and autopsy tissue reveals a unique expression and splicing profile." Abstracts of the Society for Neuroscience, Washington, DC, US, Oct. 16, 2012, Retrieved from the Internet Aug. 19, 2016: http://www.abstractsonline.com/Plan/ViewAbstract.aspx?sKey=99bd542e-9dff-4338-9756-dfbeb1839aa6&cKey=63d1b086-9f01-43d4-ab3f-d258faa86d9e&mKey=%7b70007181-01C9-4DE9-A0A2-EEBFA14CD9F1%7d.
Donnelly et al., "Transcriptome analysis of C9orf72 ALS patient derived CNS iPS cells and autopsy tissue reveals a unique expression and splicing profile." Oral Presentation, Neuroscience 2012, Washington, DC, US, Oct. 17, 2012.
Elayadi et al., "Application of PNA and LNA oligomers to chemotherapy" Curr. Opinion Invens. Drugs (2001) 2:558-561.
European Search Report for application No. 13847957.1 dated Jul. 13, 2016.
European Search Report for application No. 13846313.8 dated May 11, 2016.
European Search Report for application No. 13847099.2 dated May 25, 2016.
Extended European Search Report for application No. 14852924.1 dated Jun. 20, 2017.
Fernandes et al., "Oligonucleotide-Based Therapy for FTD/ALS Caused by the C9orf72 Repeat Expansion: A Perspective" Journal of Nucleic Acids (2013) :1-11.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Ganesalingam et al., "Combination of neurofiliment heavy chain and complement C3 as CSF biomarkers for ALS" Journal of Neurochemistry (2011) 117: 528-537.
Gautschi et al., "Activity of a novel bcl-2/bcl-xLbispecific antisense oligonucleotide against tumors of diverse histologic origins" J. Natl. Cancer Inst. (2001) 93:463-471.
GenBank: Accession No. NT_008413 Jul. 24, 2012.
GenBank: JU333328.1 TSA: Macaca mulatta Mamu_527777 mRNA sequence. Mar. 26, 2012 (Retrieved from the internet Sep. 12, 2016: http://www.ncbi.nlm.nih.gov/nuccore/380810415?sat=18&satkey=24474174).
Gendron et al., "Poly(GP) proteins are a useful pharmacodynamic marker for C9ORF72-associated amyotrophic lateral sclerosis" Sci Tran Med (2017) 9(383):1-12.
Hirtz et al., "How common are the "common" neurologic disorders?" Neurology (2007) 68:326-337.
Ince et al., "Molecular pathology and genetic advances in amyotrophic lateral sclerosis: an emerging molecular pathway and the significance of glial pathology," Acta Neuro. (2011) 122:657-671.
International Search Report for application No. PCT/US2013/065073 dated Apr. 22, 2014.
International Search Report for application No. PCT/US2013/065067 dated Jan. 24, 2014.
International Search Report for application No. PCT/US2013/065131 dated Feb. 14, 2014.
International Search Report for application on. PCT/US2014/060194 dated Apr. 14, 2015.
International Search Report for application on. PCT/US2016/027747 dated Sep. 30, 2016.
International Search Report for application No. PCT/US17/27355 dated Jul. 26, 2017.
International Search Report for application No. PCT/US2016/060106 dated Feb. 1, 2017.
Jiang et al., "Antisense oligonucleotide therapy for ALS/FTD caused by a gain of toxicity from C9orf72 hexanucleotide expansions." Poster Presentation, 10th Brain Research Conference, RNA Metabolism in Neurological Disease, Oct. 16, 2015.
Jiang et al. "Gain of Toxicity from ALS/FTG-Linked Repeat Expansions in C9ORF72 Is Alleviated by Antisense Oligonucleotides Targeting GGGCC-Containing RNAs." Neuron (2016) 90:535-550.
Jeong et al., "Rapid Identification of Monospecific Monoclonal Antibodies Using a Human Proteome Microarray." Mol. Cell. Proteomics (2012) 11(6): O111.016253-1 to O111.016253-10.
Johnson et al., "Exome sequencing reveals VCP mutations as a cause of familial ALS" Neuron (2010) 68:857-864.
Jones et al., "RNA quantitation by fluorescence-based solution assay: RiboGreen reagent characterization" Analytical Biochemistry (1998) 265(2):368-374.
Klein et al., "Gain of RNA function in pathological cases: Focus on myotonic dystrophy" Biochimie (2011) 93(11):2006-2012.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Kwiatkowski et al., "Mutations in the FUS/TLS gene on chromosome 16 cause familial amyotrophic lateral sclerosis" Science (2009) 323:1205-1208.
Laaksovirta et al, "Chromosome 9p21 in amyotrophic lateral sclerosis in Finland. A genome-wide association study" Lancet Neurol. (2010) 9:978-985.
Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.
Lagier-Tourenne, C., "Targeted degradation of sense and antisense C9orf72 nuclear foci as therapy for ALS and FTD" Oral Presentation, 24th International Symposium on ALS/MND, Milan, Dec. 6, 2013.
Lagier-Tourenne, C., "Identifying mechanisms and therapy for ALS/FTD from C9orf72 expansion", Oral Presentation, ALSA and AFTD Symposium, Society for Neuroscience Annual Meeting, New Orleans; Oct. 15, 2012.
Lagier-Tourenne, C. "Therapy Development for ALS/MND and Frontotemporal Dementia with C9orf72 Expansion: Antisense Oligonucleotide Mediated Reduction in Nuclear RNA Foci." ALS FD (Nov. 4, 2013) 14(sup2): p. 17.

(56) References Cited

OTHER PUBLICATIONS

Lagier-Tourenne et al., "Targeted Degradation of Sense and Antisense C9ORF72 RNA Foci as Therapy for ALS and Frontotemporal Degeneration" PNAS (2013) 110(47):E4530-E4539.
Lee et al., "Antisense Therapy in Neurology" Journal of Personalized Medicine (2013) 3(3): 144-176.
Leumann et al., "DNA Analogues: From Supramolecular Principles to Biological Properties" Bioorganic & Medicinal Chemistry (2002) 10:841-854.
Lillo et al., "Frontotemporal dementia and motor neurone disease: overlapping clinic-pathological disorders" J. Clin. Neurosci. (2009) 16:1131-1135.
Lindquist et al, "Corticobasal and ataxia syndromes widen the spectrum of C9ORF72 hexanucleotide expansion disease." Clin Genet (2013) 83:279-283.
Madson, "Antisense Against C9ORF72", http://alsn.mda.org/article/antisense-against-c9orf72 Jul. 1, 2012 (printed Oct. 28, 2015).
Maher et al., "Comparative hybrid arrest by tandem antisense oligodeoxyribonucleotides or oligodeoxyribonucleoside methylpbosphonates in a cell-free system" Nucl. Acid. Res. (1998) 16(8):3341-3358.
Mahoney et al., "Frontotemporal dementia with the C9ORF72 hexanucleotide repeat expansion: clinical, neuroanatomical and neuropathological features" Brain (2012) 135: 736-750.
Margolis et al., "DM2 intronic expansions: evidence for CCUG accumulation without flanking sequence or effects on ZNF9 mRNA processing or protein expression" Hum. Mol. Genet. (2006) 15:1808-1815.
Martin, "New acces to 2'-O-alkylated ribonucleosides and properties of 2'-O-alkylated oligoribonucleotides" Helv. Chim. Acta. (1995) 78:486-504.
Maruyama et al., "Mutations of optineurin in amyotrophic lateral sclerosis" Nature (2010) 465:223-226.
Morita et al., "A locus on chromosome 9p confers susceptibility to ALS and frontotemporal dementia" Neurology (2006) 66:839-844.
Mulders et al., "Triplet-repeat oligonucleotide-mediated reversal of RNA toxicity in myotonic dystrophy" PNAS (2009) 106(33):13915-13920.
Nelson et al., "The unstable repeats--three evolving faces of neurological disease." Neuron (2013) 77(5):825-43.
Neumann et al., "Ubiquitinated TDP-43 in frontotemporal lobar degeneration and amyotrophic lateral sclerosis" Science (2006) 314:130-133.
New England Biolabs 1998/99 Catalog (cover page and pp. 121 and 284).
O'Rourke et al., "C9orf72 BAC Transgenic Mice Display Typical Pathologic Features of ALS/FTD." Neuron (2015) 88(5):892-901.
Orum et al., "Locked nucleic acids: A promising molecular family for gene-function analysis and antisense drug development" Curr. Opinion Mol. Ther. (2001) 3:239-243.
Ostrow et al., "The C9orf72 ALS mutation causes both increased expression and aberrant splicing og the endothelin-B receptor, and its ligand endothelin-1 is increased in CNS tissue from ALS patients and mutant mice," Abstracts of the Society for Neuroscience (Oct. 17, 2012) 42: p. 1.
Pearson et al., "Familial frontotemporal dementia with amyotrophic lateral sclerosis and a shared haplotype on chromosome 9p" J. Nerol. (2011) 258:647-655.
Rabin et al., "Sporadic ALS has compartment-specific aberrant exon splicing and altered cell-matrix adhesion biology" Hum Mol Genet. (2010) 19(2):313-328.
Ravits, J., "Expanding Neurodegenerations: C9orf72-ALS/FTD" Oral Presentation, ANA Meeting, New Orleans, LA, (Oct. 15, 2013).
Ravits. J., "Regional Spread in ALS: Mechanisms and Pathogenesis." Oral Presentation, 2nd Annual Neuromuscular Colloquium, UC Irvine, Newport Beach, CA, May 4, 2012.
Renton et al., "A Hexanucleotide Repeat Expansion in C9ORF72 Is the Cause of Chromosome 9p21-Linked ALS-FTD" Neuron (2011) 72:257-268.
Reynolds et al., "Rational siRNA design for RNA interference" Nature Biotechnology (2004) 22(3):326-330.
Riboldi et al., "Antisense Oligonucleotide Therapy for the Treatment of C9ORF72 ALS/FTD Diseases." Mol Neurobiol (2014) 50:721-732.
Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 14, 2015.
Rosen et al., "Mutations in Cu/Zn superoxide dismutase gene are associated with familial amyotrophic lateral sclerosis" Nature (1993) 362:59-62.
Rowland et al., "Amyotrophic lateral sclerosis" N. Engl. J. Med. (2001) 344(22):1688-1700.
Sareen et al., "Targeting RNA foci shows a therapeutic effect in iPSC-derived motor neurons from C9orf72 repeat patients." ALS FD (Nov. 4, 2013) 14(sup2): pp. 16-17.
Sareen et al., "Targeting RNA foci in iPSC-derived motor neurons from ALS patients with a C9ORF72 repeat expansion." Sci Tran Med (2013) 5(208): 1-13.
Sanghvi et al., "Heterocyclic Base Modifications in Nucleic Acids and Their Applications in Antisense Oligonucleotides" Antisense Research and Applications (1993) pp. 273-288.
Sha et al., "Treatment implications of C9ORF72" Alzheimers Res Ther (2012) 4(6): 46.
Singh et al., "LNA (locked nucleic acids): synthesis and high-affinity nucleic acid recognition" Chem. Commun. (1998) 4:455-456.
Singh et al., "Synthesis of 2'-amino-LNA: A novel conformationally restricted high-affinity oligonucleotide analogue with a handle" J. Org. Chem. (1998) 63: 10035-10039.
Simon-Sanchez et al., "The clinical and pathological phenotype of C9OFR72 hexanucleotide repeat expansions", Brain: Journal of Neurology (2012) 135:723-735.
Smith et al., "Comparison of biosequences" Adv. Appl. Math (1981) 2(4):482-489.
Sreedharan et al., "TDP-43 mutations in familial and sporadic amyotrophic lateral sclerosis" Science (2008) 319:1668-1672.
Srivastava et al., "Five- and Six-Membered Conformationally Locked 2',4'Carbocyclic ribo-Thymidines: Synthesis, Structure, and Biochemical Studies" J. Am. Chem. Soc. (2007) 129(26):8362-8379.
Thomsen, "Dramatically improved RNA in 1-15 situ hybridization signals using LNA-modified probes" RNA (2005) 11(11): 1745-1748.
Todd et al. "RNA mediated neurodegeneration in repeat expansion disorders," Annals of Neurology (2009) 67(3):291-300.
Vance et al., "Familial amyotrophic lateral sclerosis with frontotemporal dementia is linked to a locus on chromosome 9p13.2-21.3" Brain (2006) 129:868-876.
Wahlestedt et al., "Potent and nontoxic antisense oligonucleotide containing locked nucleic acids" Proc. Natl. Acad. Sci. USA (2000) 97: 5633-5638.
Watts et al., "Silencing disease genes in the laboratory and the clinic" J Pathol (2012) 226(2): 365-379.
Wojciechowska et al., "Cellular toxicity of expanded RNA repeats: focus on RNA foci" Human Molecular Genetics (2011) 1-11.
Woolf et al., "Specificity of antisense oligonucleotides in vivo" PNAS (1992) 89: 7305-7309.
Zhang et al., "PowerBLAST: A New Network BLAST Application for Interactive or Automated Sequence Analysis and Annotation" Genome Res. (1997) 7:649-656.
Zhang et al., "The C9orf72 repeat expansion disrupts nucleocytoplasmic transport." Nature (2015) 525(7567):56-61.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Ciura et al., "Loss of function of C9orf72 causes motor deficits in a zebrafish model of amyotrophic lateral sclerosis" Ann Neurol (2013) 74(2): 180-187.
Extended European Search Report for application No. 16780833.6 dated Nov. 15, 2018.

(56) References Cited

OTHER PUBLICATIONS

Shao, Yu, et al. "Rational design and rapid screening of antisense oligonucleotides for prokaryotic gene modulation." *Nucleic Acids Research* 34.19 (2006): 5660-5669.
Sohail, M., and E. M. Southern. "Selecting optimal antisense reagents." *Advanced Drug Delivery Reviews* 44.1 (2000): 23-34.
Boeve et al., "Characterization of frontotemporal dementia and/or amyotrophic lateral sclerosis associated with the GGGGCC repeat expansion in C9ORF72" Brain (2012) 135: 765-783.
COOK "Medicinal Chemistry of Antisense Oligonucleotides" Chapter 2 -Medicinal Chemistry of Antisense Oligonucleotides, Antisense Drug Technology, 1st Edition (2001).
Lee et al., "Rnase H-mediated degradation of toxic RNA in myotonic dystrophy type 1" PNAS (2012) 109: 4221-4226.
Wheeler et al., "Targeting nuclear RNA for in vivo correction of myotonic dystrophy" Nature (2012)488: 111-117.

\* cited by examiner

FIGS. 1A-D
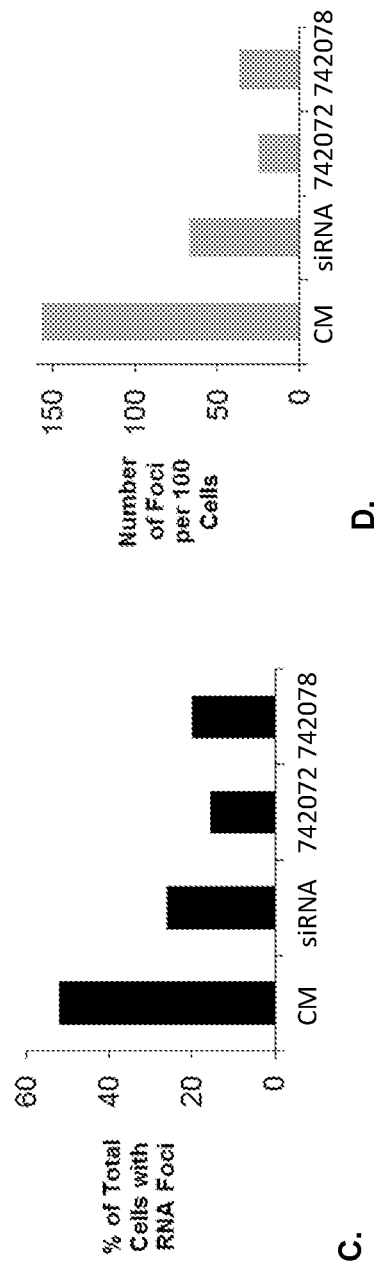

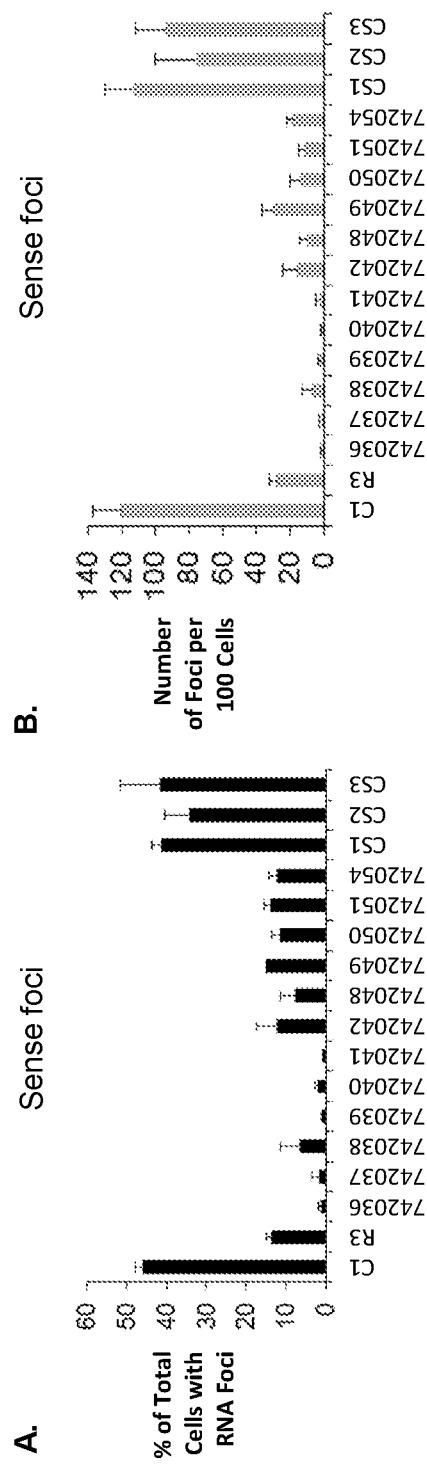
FIGS. 2A-B

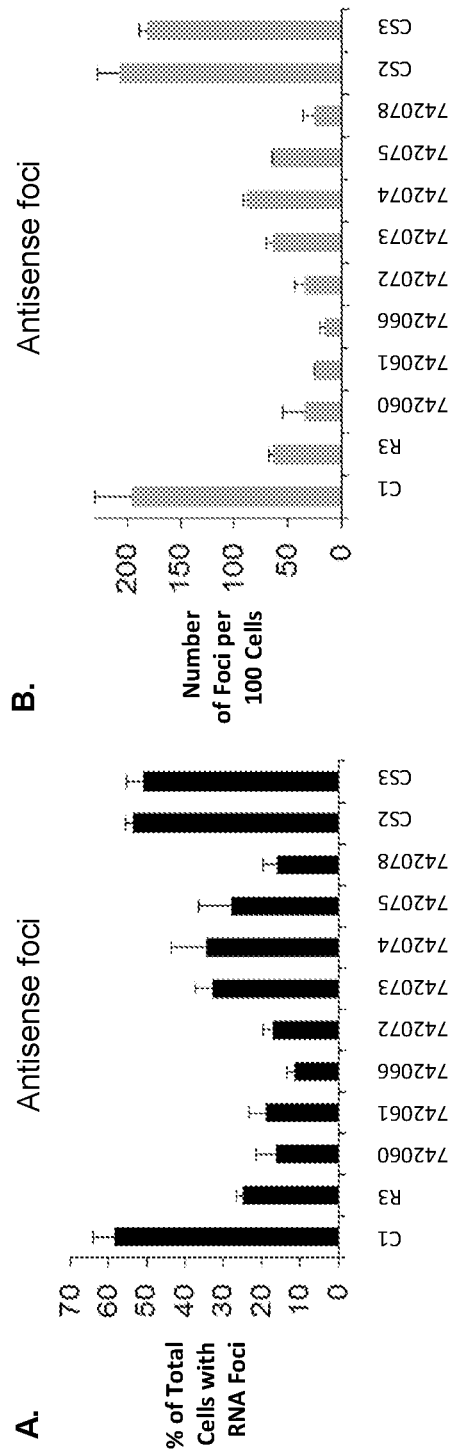
FIGS. 3A-B

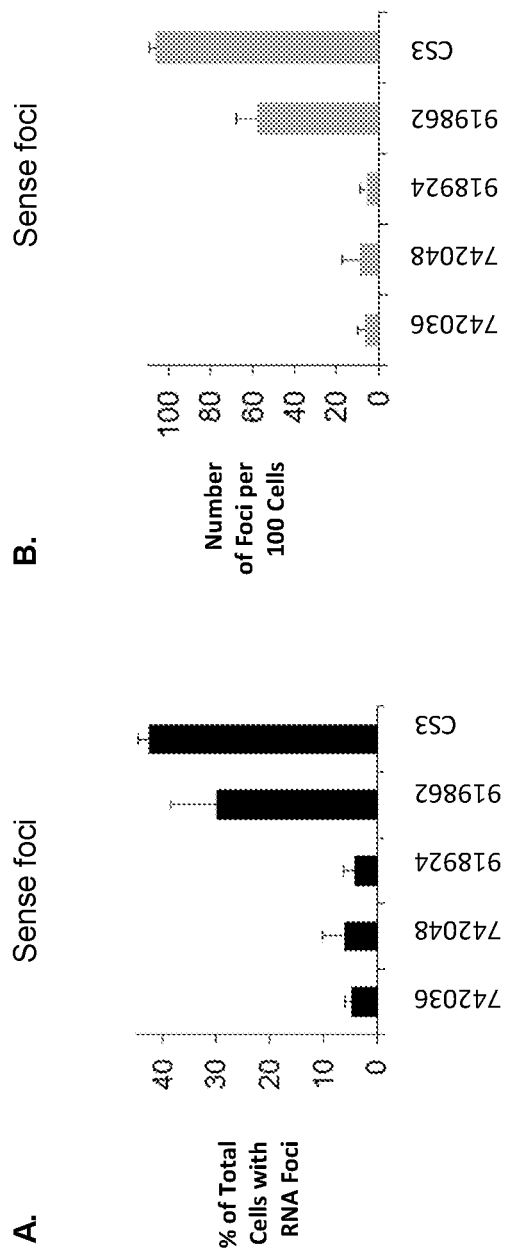
FIGS. 4A-B

COMPOUNDS AND METHODS FOR MODULATING C90RF72

This application is a national phase application under 35 U.S.C. § 371 of International Application No. PCT/US2016/060106, filed Nov. 2, 2016, which claims benefit of priority to U.S. Provisional Application No. 62/249,833, filed Nov. 2, 2015, the entire contents of each of which are hereby incorporated by reference.

STATEMENT AS TO FEDERALLY SPONSORED RESEARCH

This invention was made with government support under Grant Number GM R35118103 awarded by the National Institutes of Health. The government has certain rights in the invention.

SEQUENCE LISTING

The present application is being filed along with a Sequence Listing in electronic format. The Sequence Listing is provided as a file entitled CORE0129WOSEQ_ST25.txt, created Oct. 27, 2016, which is 52 kb in size. The information in the electronic format of the sequence listing is incorporated herein by reference in its entirety.

FIELD

Provided are compounds and methods for inhibiting expression, activity, or foci formation of C9orf72 in an animal. Such methods are useful to treat, prevent, or ameliorate neurodegenerative diseases, including amyotrophic lateral sclerosis (ALS), frontotemporal dementia (FTD), corticalbasal degeneration syndrome (CBD), atypical Parkinsonian syndrome, and olivopontocerellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). This mutation has been found to be the most common genetic cause of ALS and FTD. It is postulated that the ALS-FTD causing mutation is a large hexanucleotide (GGGGCC) repeat expansion in the first intron of the C9orf72 gene (Renton et al., Neuron, 2011, 72, 257-268; DeJesus-Hernandez et al., Neuron, 2011, 72, 245-256). A founder haplotype, covering the C9orf72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985). There are currently no effective therapies to treat such neurodegenerative diseases.

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression, activity, or function. The modulation of gene expression can be achieved by, for example, target degradation or occupancy-based inhibition. Antisense technology is an effective means for modulating the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

BRIEF SUMMARY

Provided herein are compounds comprising modified oligonucleotides complementary to a C9orf72 transcript. Such oligomeric compounds comprise a 5'-terminal group, wherein the 5'-terminal group is a phosphorus moiety. In certain embodiments, the modified oligonucleotides provided herein are expected to have enhanced nuclease stability. In certain embodiments, the modified oligonucleotides are expected to hybridize to a portion of a target RNA resulting in modulation of normal function of the target RNA, wherein the target RNA is a C9orf72 transcript. In certain embodiments, the modified oligonucleotides are complementary to the hexanucleotide repeat region of a C9orf72 transcript. In certain embodiments, the modified oligonucleotides are complementary to the hexanucleotide repeat region of a C9orf72 sense transcript. In certain embodiments, the modified oligonucleotides are complementary to the hexanucleotide repeat region of a C9orf72 antisense transcript.

The compounds are defined individually in further detail herein. It is to be understood that the oligomeric compounds provided herein include all combinations of the embodiments disclosed and variables defined herein.

The following non-limiting numbered embodiments are provided.

Embodiment 1

A compound comprising a modified oligonucleotide and a terminal group at the 5'-end of the modified oligonucleotide, wherein
the modified oligonucleotide consists of 13 to 30 linked nucleosides and has a nucleobase sequence comprising a complementary region having at least 7 contiguous nucleobases complementary to an equal-length portion within a target region of a target nucleic acid, wherein the target nucleic acid is a C9orf72 transcript;
and wherein the terminal group comprises a phosphorus moiety.

Embodiment 2

The compound of embodiment 1, wherein the target region of the C9orf72 transcript comprises a hexanucleotide repeat.

Embodiment 3

The compound of any of embodiments 1 or 2, wherein the target region of the C9orf72 transcript is within a hexanucleotide repeat region.

Embodiment 4

The compound of any of embodiments 1 to 3, wherein the complementary region comprises at least 10 contiguous nucleobases complementary to an equal-length portion within the target region of the C9orf72 transcript.

Embodiment 5

The compound of any of embodiments 1 to 3, wherein the complementary region comprises at least 12 contiguous nucleobases complementary to an equal-length portion within the target region of the C9orf72 transcript.

Embodiment 6

The compound of any of embodiments 1 to 3, wherein the complementary region comprises at least 14 contiguous nucleobases complementary to an equal-length portion within the target region of the C9orf72 transcript.

Embodiment 7

The compound of any of embodiments 1 to 3, wherein the complementary region comprises at least 16 contiguous nucleobases complementary to an equal-length portion within the target region of the C9orf72 transcript.

Embodiment 8

The compound of any of embodiments 1 to 3, wherein the complementary region comprises at least 18 contiguous nucleobases complementary to an equal-length portion within the target region of the C9orf72 transcript.

Embodiment 9

The compound of any of embodiments 1 to 8, wherein the C9orf72 transcript is a C9orf72 sense transcript.

Embodiment 10

The compound of any of embodiments 1 to 8, wherein the C9orf72 transcript is a C9orf72 antisense transcript.

Embodiment 11

The compound of any of embodiments 1 to 10, wherein the 5'-terminal nucleoside and terminal group of the compound has Formula I:

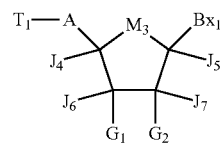

wherein:
$T_1$ is a phosphorus moiety;
A has a formula selected from among:

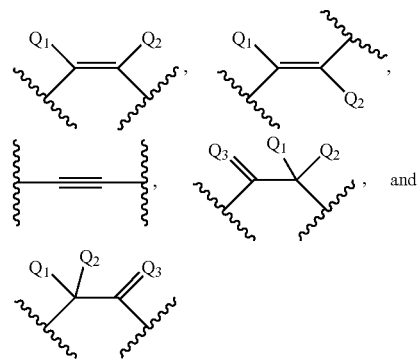

$Q_1$ and $Q_2$ are each independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl, and $N(R_3)(R_4)$;
$Q_3$ is selected from among: O, S, $N(R_5)$, and $C(R_6)(R_7)$;
each $R_3$, $R_4$ R5, $R_6$ and $R_7$ is independently selected from among: H, $C_1$-$C_6$ alkyl, substituted $C_1$-$C_6$ alkyl, and $C_1$-$C_6$ alkoxy;
$M_3$ is selected from among: O, S, $NR_{14}$, $C(R_{15})(R_{16})$, $C(R_{15})(R_{16})C(R_{17})(R_8)$, $C(R_{15})$=$C(R_{17})$, $OC(R_{15})(R_{16})$, and $OC(R_{15})(Bx_2)$;
$R_{14}$ is selected from among: H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
$R_{15}$, $R_{16}$, $R_{17}$ and $R_{18}$ are each independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

if $Bx_2$ is present, then $Bx_2$ is a nucleobase and $Bx_1$ is selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

if $Bx_2$ is not present, then $Bx_1$ is a nucleobase;

either each of $J_4$, $J_5$, $J_6$ and $J_7$ is independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

or $J_4$ forms a bridge with one of $J_5$ or $J_7$ wherein the bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

each $R_{19}$, $R_{20}$ and $R_{21}$ is independently selected from among: H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

one of $G_1$ and $G_2$ is selected from among: H, OH, halogen and O—$[C(R_8)(R_9)]_n$—$[(C=O)_m$—$X_1]_j$—Z;

and the other of $G_1$ and $G_2$ is: O-$T_2$;

$T_2$ is an internucleoside linking group linking the 5'-terminal nucleoside of Formula I to the remainder of the oligonucleotide;

each $R_8$ and $R_9$ is independently selected from among: H, halogen, $C_1$-$C_6$ alkyl, and substituted $C_1$-$C_6$ alkyl;

$X_1$ is O, S or $N(E_1)$;

Z is selected from among: H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, and $N(E_2)(E_3)$;

$E_1$, $E_2$ and $E_3$ are each independently selected from among: H, $C_1$-$C_6$ alkyl, and substituted $C_1$-$C_6$ alkyl;

n is from 1 to 6;

m is 0 or 1;

j is 0 or 1;

provided that, if j is 1, then Z is other than halogen or $N(E_2)(E_3)$;

each substituted group comprises one or more optionally protected substituent groups independently selected from among: a halogen, $OJ_1$, $N(J_1)(J_2)$, =$NJ_1$, $SJ_1$, $N_3$, CN, $OC(=X_2)J_1$, $OC(=X_2)N(J_1)(J_2)$, and $C(=X_2)N(J_1)(J_2)$;

$X_2$ is O, S or $NJ_3$; and each $J_1$, $J_2$ and $J_3$ is independently selected from among: H and $C_1$-$C_6$ alkyl.

Embodiment 12

The compound of embodiment 11, wherein $M_3$ is selected from among: O, CH=CH, $OCH_2$, and $OC(H)(Bx_2)$.

Embodiment 13

The compound of embodiment 11, wherein $M_3$ is O.

Embodiment 14

The compound of any of embodiments 11 to 13, wherein each of $J_4$, $J_5$, $J_6$ and $J_7$ is H.

Embodiment 15

The compound of any of embodiments 11 to 14, wherein $J_4$ forms a bridge with either $J_5$ or $J_7$.

Embodiment 16

The compound of any of embodiments 11 to 15, wherein A has the formula:

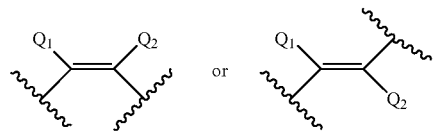

wherein:
$Q_1$ and $Q_2$ are each independently selected from among: H, halogen, $C_1$-$C_6$ alkyl, substituted $C_1$-$C_6$ alkyl, $C_1$-$C_6$ alkoxy, and substituted $C_1$-$C_6$ alkoxy.

Embodiment 17

The compound of embodiment 16, wherein each of $Q_1$ and $Q_2$ is H.

Embodiment 18

The compound of embodiment 16, wherein $Q_1$ and $Q_2$ are each independently selected from among: H and a halogen.

Embodiment 19

The compound of embodiment 16, wherein one of $Q_1$ and $Q_2$ is H and the other of $Q_1$ and $Q_2$ is F, $CH_3$ or $OCH_3$.

Embodiment 20

The compound of any of embodiments 11 to 19, wherein $T_1$ has the formula:

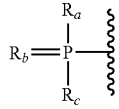

wherein:
$R_a$ and $R_c$ are each independently selected from among: hydroxyl, protected hydroxyl, thiol, protected thiol, $C_1$-$C_6$ alkyl, substituted $C_1$-$C_6$ alkyl, $C_1$-$C_6$ alkoxy, substituted $C_1$-$C_6$ alkoxy, amino, protected amino or substituted amino; and
$R_b$ is O or S.

Embodiment 21

The compound of embodiment 20, wherein $R_b$ is O and $R_a$ and $R_c$ are each, independently selected from among: OH, $OCH_3$, $OCH_2CH_3$, $OCH(CH_3)_2$.

Embodiment 22

The compound of any of embodiments 11 to 21, wherein one of $G_1$ and $G_2$ is selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2-CH=CH_2$, $O(CH_2)_2-OCH_3$, $O(CH_2)_2-SCH_3$, $O(CH_2)_2-OCF_3$, $O(CH_2)_3-N(R_{10})(R_{11})$, $O(CH_2)_2-ON(R_{10})(R_{11})$, $O(CH_2)_2-O(CH_2)_2-N(R_{10})(R_{11})$, $OCH_2C(=O)-N(R_{10})(R_{11})$, $OCH_2C(=O)-N(R_{12})-(CH_2)_2-N(R_{10})(R_{11})$, and $O(CH_2)_2-N(R_{12})-C(=NR_{13})[N(R_{10})(R_{11})]$; wherein $R_{10}$, $R_{11}$, $R_{12}$ and $R_{13}$ are each, independently, H or $C_1-C_6$ alkyl.

Embodiment 23

The compound of any of embodiments 11 to 22, wherein one of $G_1$ and $G_2$ is selected from among: a halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$, and $OCH_2-N(H)-C(=NH)NH_2$.

Embodiment 24

The compound of any of embodiments 11 to 23, wherein one of $G_1$ and $G_2$ is selected from among: F, $OCH_3$, and $O(CH_2)_2-OCH_3$.

Embodiment 25

The compound of embodiment 24, wherein one of $G_1$ and $G_2$ is $O(CH_2)_2-OCH_3$.

Embodiment 26

The compound of any of embodiments 11 to 25, wherein the 5'-terminal nucleoside and terminal group of the compound has Formula III:

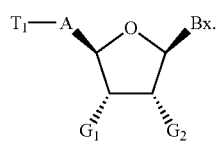

III

Embodiment 27

The compound of embodiment 26, wherein A has the formula:

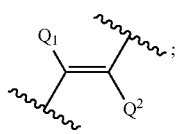

wherein $Q_1$ and $Q_2$ are each independently selected from among: H, a halogen, $C_1-C_6$ alkyl, substituted $C_1-C_6$ alkyl, $C_1-C_6$ alkoxy, and substituted $C_1-C_6$ alkoxy.

Embodiment 28

The compound of embodiment 27, wherein $Q_1$ and $Q_2$ are each independently selected from among: H, F, $CH_3$, and $OCH_3$.

Embodiment 29

The compound of any of embodiments 11 to 28, wherein the 5'-terminal nucleoside and the terminal group has Formula V:

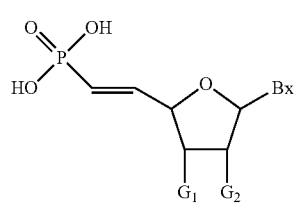

V wherein:
Bx is selected from among: uracil, thymine, cytosine, 5-methyl cytosine, adenine, and guanine;
one of $G_1$ and $G_2$ is selected from among: a halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$ and $OCH_2-N(H)-C(=NH)NH_2$;
and the other of $G_1$ and $G_2$ is $O-T_2$, wherein $T_2$ is a phosphorothioate internucleoside linking group linking the compound of Formula V to the remainder of the oligonucleotide.

Embodiment 30

The compound of any of embodiments 1 to 29, wherein the modified oligonucleotide comprises at least two modified sugar moieties.

Embodiment 31

The compound of embodiment 30, wherein the modified oligonucleotide is fully modified.

Embodiment 32

The compound of any of embodiments 30 to 31, wherein each modified sugar moiety is independently selected from among: 2'-F, 2'-MOE, 2'-OMe, LNA, F-HNA, and cEt.

Embodiment 33

The compound of any of embodiments 1 to 32, wherein the modified oligonucleotide comprises at least one region having sugar motif:

$-[(A)_x-(B)_y-(A)_z]_q$ wherein
A is a modified nucleoside of a first type,
B is a modified nucleoside of a second type;
each x and each y is independently 1 or 2;
z is 0 or 1;
q is 3-15.

Embodiment 34

The compound of embodiment 33, wherein each x and each y is 1.

Embodiment 35

The compound of embodiment 33 or 34, wherein A is a modified nucleoside selected from among: a 2'-F, a 2'-OMe, and a F-HNA modified nucleoside.

Embodiment 36

The compound of embodiment 33 or 34, wherein B is a modified nucleoside selected from among: a 2'-F, a 2'-OMe, and a F-HNA modified nucleoside.

Embodiment 37

The compound of any of embodiments 33 to 36, wherein A is a 2'-F modified nucleoside and B is a 2'-OMe modified nucleoside.

Embodiment 38

The compound of any of embodiments 33 to 36, wherein B is a 2'-F modified nucleoside and A is a 2'-OMe modified nucleoside.

Embodiment 39

The compound of any of embodiments 1 to 38, wherein the modified oligonucleotide comprises 1-4 3'-terminal nucleosides, each comprising the same modified sugar moiety, wherein the modified sugar moiety of the 1-4 3'-terminal nucleosides is different from the modified sugar moiety of the immediately adjacent nucleoside.

Embodiment 40

The compound of embodiment 39, wherein the 3'-terminal nucleosides are each 2'-MOE nucleosides.

Embodiment 41

The compound of embodiment 39 or 40 comprising two 3'-terminal nucleosides.

Embodiment 42

The compound of any of embodiments 1 to 41, wherein the modified oligonucleotide comprises at least one modified internucleoside linkage.

Embodiment 43

The compound of any of embodiments 1 to 42, wherein each internucleoside linkage of the modified oligonucleotide is selected from a phosphorothioate internucleoside linkage and an unmodified, phosphate internucleoside linkage.

Embodiment 44

The compound of embodiment 42 or 43, wherein each of the 6-10 3'-most internucleoside linkages of the modified oligonucleotide is a phosphorothioate internucleoside linkage.

Embodiment 45

The compound of any of embodiments 42 to 44, wherein the 5'-most internucleoside linkage of the modified oligonucleotide is a phosphorothioate internucleoside linkage.

Embodiment 46

The compound of any of embodiments 42 to 45, wherein the modified oligonucleotide comprises a region of at least 4 internucleoside linkages that alternate between phosphorothioate and phosphate internucleoside linkages.

Embodiment 47

The compound of any of embodiments 1 to 46, comprising the motif:

$$\text{5'-(Nucleoside of Formula I, III, or V)-}s\text{-(A-}s\text{-B-}o\text{-A)}_x\text{ (-}s\text{-B)}_Y$$

wherein:

A is a nucleoside of a first type;

B is a nucleoside of a second type;

s is a phosphorothioate internucleoside linkage;

o is a phosphate internucleoside linkage;

x is 1-8; and

Y is 1 or 0.

Embodiment 48

The compound of any of embodiments 1 to 47, comprising the motif:

$$(A\text{-}s\text{-}B\text{-}s\text{-}A)_z(\text{-}s\text{-}B)_q\text{-}s\text{-}(D)\text{-}(s\text{-}D)_r\text{-3'}$$

wherein:

s is a phosphorothioate linkage;

A is a nucleoside of a first type;

B is a nucleoside of a second type;

D is a nucleoside of a third type;

Z is 1-5;

q is 1 or 0; and and r is 0-3.

Embodiment 49

The compound of embodiment 47 or 48, wherein A is a 2'-F modified nucleoside.

Embodiment 50

The compound of any of embodiments 47 to 49, wherein B is a 2'-OMe modified nucleoside.

Embodiment 51

The compound of any of embodiments 48 to 50, wherein D is a 2'-MOE modified nucleoside.

Embodiment 52

The compound of any of embodiments 1 to 46, comprising the motif:

(Nucleoside of Formula V)-*s*-A-*s*-B-*o*-A-*s*-B-*o*-A-*s*-
B-*o*-A-*s*-B-*o*-A-*s*-B-*o*-A-*s*-B-*o*-A-*s*-B-*s*-A-*s*-B-*s*-
A-*s*-B-*s*-D-*s*-D-*s* wherein:
s is a phosphorothioate internucleoside linkage;
o is a phosphate internucleoside linkage;
A is a nucleoside of a first type;
B is a nucleoside of a second type; and
D is a nucleoside of a third type.

Embodiment 53

The compound of any of embodiments 1 to 46, consisting of the motif:

(Nucleoside of Formula V)-*s*-A-*s*-B-*o*-A-*s*-B-*o*-A-*s*-
B-*o*-A-*s*-B-*o*-A-*s*-B-*o*-A-*s*-B-*o*-A-*s*-B-*s*-A-*s*-B-*s*-
A-*s*-B-*s*-D-*s*-D-*s* wherein:
s is a phosphorothioate linkage;
o is a phosphate internucleoside linkage;
A is a nucleoside of a first type;
B is a nucleoside of a second type; and
D is a nucleoside of a third type.

Embodiment 54

The compound of any of embodiments 52 to 53, wherein A is a 2'-F modified nucleoside.

Embodiment 55

The compound of any of embodiments 52 to 53, wherein B is a 2'-OMe modified nucleoside.

Embodiment 56

The compound of any of embodiments 52 to 55, wherein D is a 2'-MOE modified nucleoside.

Embodiment 57

The compound of any of embodiments 1 to 56, wherein the modified oligonucleotide has two mismatches relative to the target region of the C9orf72 transcript.

Embodiment 58

The compound of any of embodiments 1 to 56, wherein the modified oligonucleotide has three mismatches relative to the target region of the C9orf72 transcript.

Embodiment 59

The compound of any of embodiments 1 to 56, wherein the modified oligonucleotide has four mismatches relative to the target region of the C9orf72 transcript.

Embodiment 60

The compound of any of embodiments 1 to 56, wherein the modified oligonucleotide has five mismatches relative to the target region of the C9orf72 transcript.

Embodiment 61

The compound of any of embodiments 1 to 56, wherein the modified oligonucleotide has six mismatches relative to the target region of the C9orf72 transcript.

Embodiment 62

The compound of any of embodiments 57 to 61, wherein the 5'-most nucleobase and 3'-most nucleobase of the modified oligonucleotide are mismatches relative to the target region of the C9orf72 transcript.

Embodiment 63

The compound of any of embodiments 58 to 61, wherein the 5'-most nucleobase and the two 3'-most nucleobases of the modified oligonucleotide are mismatches relative to the target region of the C9orf72 transcript.

Embodiment 64

The compound of any of embodiments 57 to 61, wherein the nucleobases at positions 9 and 14 of the modified oligonucleotide are mismatches relative to the target region of the C9orf72 transcript.

Embodiment 65

The compound of any of embodiments 58 to 61, wherein the nucleobases at positions 9, 10, and 11 of the modified oligonucleotide are mismatches relative to the target region of the C9orf72 transcript.

Embodiment 66

The compound of any of embodiments 1 to 65, wherein the complementary region is between the 5'-most nucleoside and the two 3'-most nucleosides of the modified oligonucleotide and is 100% complementary to the target region of the C9orf72 transcript.

Embodiment 67

The compound of any of embodiments 1 to 65, wherein the complementary region is between the 5'-most nucleoside and the two 3'-most nucleosides of the modified oligonucleotide and is 90% complementary to the target region of the C9orf72 transcript.

Embodiment 68

The compound of any of embodiments 1 to 65, wherein the complementary region is between the 5'-most nucleoside and the two 3'-most nucleosides of the modified oligonucleotide and is 80% complementary to the target region of the C9orf72 transcript.

Embodiment 69

The compound of any of embodiments 1 to 68, wherein each of the nucleobases in the complementary region of the modified oligonucleotide is selected from among: adenine, guanine, cytosine, 5'-methylcytosine, thymine, and uracil.

Embodiment 70

The compound of any of embodiments 1 to 69, wherein each of the nucleobases in the modified oligonucleotide is selected from among: adenine, guanine, cytosine, 5'-methylcytosine, thymine, and uracil.

Embodiment 71

The compound of any of embodiments 1 to 70, wherein the modified oligonucleotide does not comprise a modified nucleobase.

Embodiment 72

The compound of any of embodiments 1 to 70, wherein the modified oligonucleotide comprises 5-methylcytosine.

Embodiment 73

The compound of any of embodiments 1 to 8 or 10 to 72, wherein the nucleobase sequence of the oligonucleotide comprises a nucleobase sequence selected from among: SEQ ID NO: 26, 27, 28, 29, 30, 31, 32, 33, 34, 35, 36, 37, 38, 39, 40, 41, 42, 43, 44, 45, 46, 47, 48, and 49.

Embodiment 74

The compound of any of embodiments 1 to 9 or 11 to 72, wherein the nucleobase sequence of the oligonucleotide comprises a nucleobase sequence selected from among: SEQ ID NO: 2, 3, 4, 5, 6, 7, 8, 9, 10, 11, 12, 13, 14, 15, 16, 17, 18, 19, 20, 21, 22, 23, 24, and 25.

Embodiment 75

The compound of any of embodiments 1 to 74, wherein the phosphorus moiety is an unmodified phosphate.

Embodiment 76

The compound of any of embodiments 1 to 74, wherein the phosphorus moiety is a 5'-(E)-vinylphosphonate group having the formula:

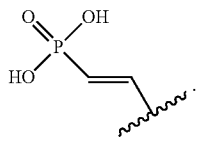

Embodiment 77

The compound of any of embodiments 1 to 76, wherein the compound comprises an unlocked nucleic acid or an abasic nucleoside.

Embodiment 78

The compound of embodiment 77, wherein the compound comprises an unlocked nucleic acid.

Embodiment 79

The compound of embodiment 78, wherein the nucleobase attached to the sugar moiety of the unlocked nucleic acid is mismatched relative to the corresponding nucleobase of the target region of the C9orf72 transcript.

Embodiment 80

The compound of any of embodiments 1 to 79, wherein the compound is an oligomeric compound.

Embodiment 81

The compound of embodiment 80, wherein the compound consists of the oligomeric compound.

Embodiment 82

The compound of any of embodiments 80 or 81, wherein the oligomeric compound is paired with a second oligomeric compound to form a duplex.

Embodiment 83

The compound of any of embodiments 1 to 81, wherein the compound is single-stranded.

Embodiment 84

A pharmaceutical composition comprising the compound of any of embodiments 1 to 83, and a pharmaceutically acceptable carrier or diluent.

Embodiment 85

A method of treating a neurodegenerative disease comprising contacting a cell with the compound or composition of any of embodiments 1 to 84.

Embodiment 86

A method of reducing C9orf72 foci comprising contacting a cell with the compound or composition of any of embodiments 1 to 84.

Embodiment 87

The method of embodiments 85 or 86, wherein the cell is in vitro.

Embodiment 88

The method of embodiments 85 or 86, wherein the cell is in an animal.

Embodiment 89

The method of embodiment 88, wherein the animal is a human.

Embodiment 90

Use of the compound or composition of any of embodiments 1 to 84 for the manufacture of a medicament for treating a neurodegenerative disease.

Embodiment 91

Use of the compound or composition of any of embodiments 1 to 84 for treating a neurodegenerative disease.

Embodiment 92

The method or use of any of embodiments 85 or 89 to 91, wherein the neurodegenerative disease is amyotrophic lateral sclerosis.

BRIEF DESCRIPTION OF FIGURES

FIGS. 1A-D show the percentage of observed cells containing C9orf72 sense or antisense foci and the number of foci per 100 cells for cells treated with a negative control oligonucleotide ("CM"), positive control siRNA, or Isis No. 742048, 742054, 742072, or 742078.

FIGS. 2A-B show the percentage of observed cells containing C9orf72 sense foci and the number of foci per 100 cells for cells treated with a control compound or modified oligonucleotide.

FIGS. 3A-B show the percentage of observed cells containing C9orf72 antisense foci and the number of foci per 100 cells for cells treated with a control compound or modified oligonucleotide.

FIGS. 4A-B show the percentage of observed cells containing C9orf72 sense foci and the number of foci per 100 cells for cells treated with a control compound or modified oligonucleotide lacking a 5'-phosphate.

DETAILED DESCRIPTION

It is to be understood that both the foregoing general description and the following detailed description are exemplary and explanatory only and are not restrictive. Herein, the use of the singular includes the plural unless specifically stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"Antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound. In certain embodiments, antisense activity is a change in splicing of a pre-mRNA nucleic acid target. In certain embodiments, antisense activity is a change in the localization or structural formation of a nucleic acid target. In certain such embodiments, antisense activity is a decrease in foci formation of a nucleic acid target.

"Antisense compound" means a compound comprising an antisense oligonucleotide and optionally one or more additional features, such as a conjugate group or terminal group.

"Antisense oligonucleotide" means an oligonucleotide that (1) has a nucleobase sequence that is at least partially complementary to a target nucleic acid and that (2) is capable of producing an antisense activity in a cell or animal.

"Ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

"Bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"C9orf72 antisense transcript" means a RNA produced from the non-coding strand (also antisense strand and template strand) of the C9orf72 gene. The C9orf72 antisense transcript differs from the canonically transcribed "C9orf72 sense transcript", which is a RNA produced from the coding strand (also sense strand) of the C9orf72 gene.

"C9orf72 associated disease" means any disease associated with any C9orf72 nucleic acid or expression product thereof, regardless of which DNA strand the C9orf72 nucleic acid or expression product thereof is derived from. Such diseases may include a neurodegenerative disease. Such neurodegenerative diseases may include ALS and FTD.

"C9orf72 foci" means nuclear foci comprising a C9orf72 transcript. In certain embodiments, C9orf72 foci comprises at least one C9orf72 sense transcript (herein "C9orf72 sense foci"). In certain embodiments, C9orf72 sense foci comprise C9orf72 sense transcripts comprising any of the following hexanucleotide repeats: GGGGCC, GGGGGG, GGGGGC, and/or GGGGCG. In certain embodiments, a C9orf72 foci comprises at least one C9orf72 antisense transcript (herein "C9orf72 antisense foci"). In certain embodiments, C9orf72 antisense foci comprise C9orf72 antisense transcripts comprising any of the following hexanucleotide repeats: GGCCCC, CCCCCC, GCCCCC, and/or CGCCCC. In certain embodiments, C9orf72 foci comprise both C9orf72 sense transcripts and C9orf72 antisense transcripts.

"C9orf72 hexanucleotide repeat" means a portion of a C9orf72 transcript that is 6 nucleotides in length and appears consecutively in the transcript at least two times. In certain embodiments, the C9orf72 hexanucleotide repeat sequence is GGCCCC or CCGGGG. A "C9orf72 hexanucleotide repeat region" is a region of a C9orf72 transcript containing only consecutive hexanucleotide repeats.

"C9orf72 hexanucleotide repeat expansion associated disease" means any disease associated with a C9orf72 nucleic acid containing a hexanucleotide repeat expansion. In certain embodiments, the hexanucleotide repeat expansion may comprise any of the following hexanucleotide repeats: GGGGCC, GGGGGG, GGGGGC, GGGGCG, GGCCCC, CCCCCC, GCCCCC, and/or CGCCCC. In certain embodiments, the hexanucleotide repeat is repeated at least 24 times. Such diseases may include a neurodegenerative disease. Such neurodegenerative diseases may include ALS and FTD.

"C9orf72 nucleic acid" means any nucleic acid derived from the C9orf72 locus, regardless of which DNA strand the C9orf72 nucleic acid is derived from. In certain embodiments, a C9orf72 nucleic acid includes a DNA sequence encoding C9orf72, an RNA sequence transcribed from DNA encoding C9orf72 including genomic DNA comprising introns and exons (i.e., pre-mRNA), and an mRNA sequence encoding C9orf72. "C9orf72 mRNA" means an mRNA encoding a C9orf72 protein. In certain embodiments, a C9orf72 nucleic acid includes transcripts produced from the coding strand of the C9orf72 gene. C9orf72 sense transcripts are examples of C9orf72 nucleic acids. In certain embodiments, a C9orf72 nucleic acid includes transcripts produced from the non-coding strand of the C9orf72 gene. C9orf72 antisense transcripts are examples of C9orf72 nucleic acids.

"C9orf72 pathogenic associated mRNA variant" means the C9orf72 mRNA variant processed from a C9orf72 pre-mRNA variant containing the hexanucleotide repeat. A C9orf72 pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 1, the complement of GENBANK Accession No. NT_008413.18 truncated from nucleosides 27535000 to 27565000). In certain embodiments, the level of a C9orf72 pathogenic associated mRNA variant is measured to determine the level of a C9orf72 pre-mRNA containing the hexanucleotide repeat in a sample.

"C9orf72 transcript" means a RNA transcribed from C9orf72. In certain embodiments, a C9orf72 transcript is a C9orf72 sense transcript. In certain embodiments, a C9orf72 transcript is a C9orf72 antisense transcript. In certain embodiments, a C9orf72 transcript comprises nucleotides upstream of nucleotide 1520 of SEQ ID NO: 1.

"Complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include, but unless otherwise specific are not limited to, adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

"Conjugate group" means a group of atoms that is directly or indirectly attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Duplex" means two oligomeric compounds that are paired. In certain embodiments, the two oligomeric compounds are paired via hybridization of complementary nucleobases.

"Fully modified" in reference to a modified oligonucleotide means a modified oligonucleotide in which each sugar moiety is modified. "Uniformly modified" in reference to a modified oligonucleotide means a fully modified oligonucleotide in which each sugar moiety is the same. For example, the nucleosides of a uniformly modified oligonucleotide can each have a 2'-MOE modification but different nucleobase modifications, and the internucleoside linkages may be different.

"Hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage.

"Linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

"Non-bicyclic modified sugar" or "non-bicyclic modified sugar moiety" means a modified sugar moiety that comprises a modification, such as a substitutent, that does not form a bridge between two atoms of the sugar to form a second ring.

"Linked nucleosides" are nucleosides that are connected in a continuous sequence (i.e. no additional nucleosides are present between those that are linked).

"Mismatch" or "non-complementary" means a nucleobase of a first oligonucleotide that is not complementary with the corresponding nucleobase of a second oligonucleotide or target nucleic acid when the first and second oligomeric compound are aligned.

"MOE" means methoxyethyl. "2'-MOE" means a —OCH$_2$CH$_2$OCH$_3$ group at the 2' position of a furanosyl ring.

"Motif" means the pattern of unmodified and/or modified sugar moieties, nucleobases, and/or internucleoside linkages, in an oligonucleotide.

"Naturally occurring" means found in nature.

"Nucleobase" means an unmodified nucleobase or a modified nucleobase. As used herein an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

"Nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase.

"Oligomeric compound" means a compound consisting of an oligonucleotide and optionally one or more additional features, such as a conjugate group or terminal group.

"Oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

"Pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

"Pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

"Pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

"Phosphorus moiety" means a group of atoms comprising a phosphorus atom. In certain embodiments, a phosphorus moiety comprises a mono-, di-, or tri-phosphate, or phosphorothioate. In certain embodiments, a phosphorus moiety comprises a modified phosphate.

"Prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

"Single-stranded" in reference to an oligomeric compound means such a compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case it would no longer be single-stranded.

"Standard cell assay" means the assay described in Example 2 and reasonable variations thereof.

"Standard in vivo experiment" means the procedure described in Example 3 and reasonable variations thereof.

"Sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Target nucleic acid" means a naturally occurring, identified nucleic acid. In certain embodiments, target nucleic acids are endogenous cellular nucleic acids, including, but not limited to RNA transcripts, pre-mRNA, mRNA, microRNA. In certain embodiments, target nucleic acids are viral nucleic acids. In certain embodiments, target nucleic acids are nucleic acids that an antisense compound is designed to affect.

"Target region" means a portion of a target nucleic acid to which an antisense compound is designed to hybridize.

"Terminal group" means a chemical group or group of atoms that is covalently linked to a terminus of an oligonucleotide.

"Unlocked nucleic acid" means a nucleoside comprising an unlocked sugar moiety. As used herein, "unlocked sugar" or "unlocked sugar moiety" means a modified sugar moiety comprising no rings. In certain embodiments, one of the bonds that is part of the ring of a furanosyl moiety is broken in an unlocked sugar.

I. Certain Oligonucleotides

In certain embodiments, the invention provides oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$ SCH$_3$, O(CH$_2$)$_2$ON(R$_m$)(R$_n$), O(CH$_2$)$_2$O(CH$_2$)$_2$N (CH$_3$)$_2$, and N-substituted acetamide (OCH$_2$C(=O)—N (R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a non-bridging 2'-substituent group selected from: F, OCH$_3$, and OCH$_2$CH$_2$OCH$_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N (OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C—(=CH$_2$)-2' and analogs thereof (see e.g., Seth et al., U.S. Pat. No. 8,278,426), 4'-C(R$_a$R$_b$)—N(R)—O-2', 4'—C (R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J Org. Chem.*, 1998, 63, 10035-10039; Srivastava et al., *J Am. Chem. Soc.*, 20017, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

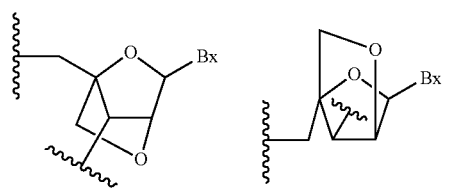

LNA (β-D-configuration)  α-L-LNA (α-L-configuration)
bridge = 4'-CH$_2$—O-2'  bridge = 4'-CH$_2$—O-2'

α-L-methyleneoxy (4'-CH$_2$—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP").

Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. &Med. Chem.* 2002, 10, 841-854), fluoro HNA:

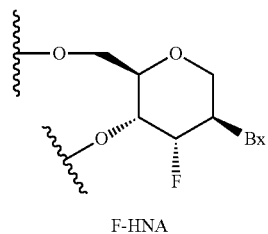

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

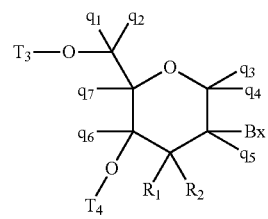

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

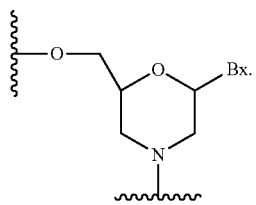

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie, International Edition*, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

B. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS-P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and nonphosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

C. Certain Motifs

In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

In certain embodiments, the present invention provides oligomeric compounds comprising one or more regions having a particular nucleoside motif. In certain embodiments, the 5'-terminal group and 5'-terminal nucleoside of an oligomeric compound of the present invention comprises a compound of Formula II, IIa, IIb, or IIc.

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a fully modified sugar motif. In such embodiments, each nucleoside of the fully modified region of the modified oligonucleotide comprises a modified sugar moiety. In certain such embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification. In certain embodiments, modified oligonucleotides comprise or consist of a region having a fully modified sugar motif, wherein the fully modified sugar motif is an alternating motif. In certain such embodiments, the sugar moieties of the alternating motif alternate between 2'-OMe and 2'-F.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage.

In certain embodiments, the oligonucleotide comprises a region of alternating internucleoside linkages. In certain such embodiments, the alternating internucleoside linkages are phosphorothioate and phosphate internucleoside linkages. In certain embodiments, the terminal internucleoside linkages are modified.

4. Certain Alternating Motifs

In certain embodiments, oligonucleotides of the present invention comprise one or more regions of alternating modifications. In certain embodiments, oligonucleotides comprise one or more regions of alternating nucleoside modifications. In certain embodiments, oligonucleotides comprise one or more regions of alternating linkage modifications. In certain embodiments, oligonucleotides comprise one or more regions of alternating nucleoside and linkage modifications.

In certain embodiments, oligonucleotides of the present invention comprise one or more regions of alternating 2'-F modified nucleosides and 2'-OMe modified nucleosides. In certain such embodiments, such regions of alternating 2'F modified and 2'OMe modified nucleosides also comprise alternating linkages. In certain such embodiments, the linkages at the 3' position of the 2'-F modified nucleosides are phosphorothioate linkages. In certain such embodiments, the linkages at the 3' position of the 2'OMe nucleosides are phosphate linkages.

In certain embodiments, oligomeric compounds comprise 2, 3, 4, 5, 6, 7, 8, 9, 10, or 11 regions of alternating modifications. Such regions may be contiguous or may be interrupted by differently modified nucleosides or linkages.

In certain embodiments, alternating motifs have a pattern in which every other moiety is a first type or a second type, e.g., ABABA, etc. In certain embodiments, alternating motifs have a pattern in which the moieties of a first type and the moieties of a second type alternate in varied numbers. For example, oligonucleotide of the present invention may include one or more regions of any of the following alternating motifs:
AABBAA;
ABBABB;
AABAAB;
ABBABAABB;
ABABAA;
AABABAB;
ABABAA;
ABBAABBABABAA;
BABBAABBABABAA; or
ABABBAABBABABAA;
wherein A is a nucleoside or internucleoside linkage of a first type and B is a nucleoside or internucleoside linkage of a second type. In certain embodiments, A and B are each selected from 2'-F, 2'-OMe, BNA, DNA, and MOE.

In certain embodiments, compounds comprising such an alternating motif also comprise a 5' terminal group and 5'-terminal nucleoside of formula II, IIa, IIb, or IIc.

5. Combinations of Motifs

It is to be understood, that certain of the above described motifs and modifications may be combined. Since a motif may comprise only a few nucleosides, a particular oligonucleotide may comprise two or more motifs. Oligonucleotides having any of the various nucleoside motifs described herein, may have any linkage motif. The lengths of the regions defined by a nucleoside motif and that of a linkage motif need not be the same. For example, non-limiting nucleoside motifs and sequence motifs are combined to show five examples in the table below. The first column of the table lists nucleosides and linkages by position from N1 (the 5'-end) to N20 (the 20$^{th}$ position from the 5'-end). In certain embodiments, oligonucleotides of the present invention are longer than 20 nucleosides (the table is merely exemplary). Certain positions in the table recite the nucleoside or linkage "none" indicating that the oligonucleotide has no nucleoside at that position.

| Pos | A | B | C | D | E |
|---|---|---|---|---|---|
| N1 | Formula II, IIa, IIb, or IIc | Formula II, IIa, IIb, or IIc | Formula II, IIa, IIb, or IIc | Formula II, IIa, IIb, or IIc | Formula II, IIa, IIb, or IIc |
| L1 | PS | PS | PS | PS | PO |
| N2 | 2'-F | 2'-F | 2'-F | 2'-OMe | MOE |
| L2 | PS | PS | PS | PO | PS |
| N3 | 2'-OMe | 2'-F | 2'-F | 2'-F | 2'-F |
| L3 | PO | PS | PS | PS | PS |
| N4 | 2'-F | 2'-F | 2'-F | 2'-OMe | 2'-F |
| L4 | PS | PS | PS | PO | PS |
| N5 | 2'-OMe | 2'-F | 2'-F | 2'-F | 2'-OMe |
| L5 | PO | PS | PS | PS | PO |
| N6 | 2'-F | 2'-OMe | 2'-F | 2'-OMe | 2'-OMe |
| L6 | PS | PO | PS | PO | PO |
| N7 | 2'-OMe | 2'-OMe | 2'-F | 2'-F | 2'-OMe |
| L7 | PO | PO | PS | PS | PO |
| N8 | 2'-F | 2'-F | 2'-F | 2'-OMe | 2'-F |
| L8 | PS | PS | PS | PO | PS |
| N9 | 2'-OMe | 2'-F | 2'-F | 2'-F | 2'-F |
| L9 | PO | PS | PS | PS | PS |
| N10 | 2'-F | 2'-OMe | 2'-F | 2'-OMe | 2'-OMe |
| L10 | PS | PO | PS | PO | PO |
| N11 | 2'-OMe | 2'-OMe | 2'-F | 2'-F | 2'OMe |
| L11 | PO | PO | PS | PS | PO |
| N12 | 2'-F | 2'-F | 2'-F | 2'-F | 2'-F |
| L12 | PS | PS | PS | PO | PS |
| N13 | 2'-OMe | 2'-F | 2'-F | 2'-F | 2'-F |
| L13 | PO | PS | PS | PS | PS |
| N14 | 2'-F | 2'-OMe | 2'-F | 2'-F | 2'-F |
| L14 | PS | PS | PS | PS | PS |
| N15 | 2'-OMe | 2'OMe | 2'-F | 2'-F | 2'-MOE |
| L15 | PS | PS | PS | PS | PS |
| N16 | 2'-F | 2'OMe | 2'-F | 2'-F | 2'-MOE |
| L16 | PS | PS | PS | PS | PS |
| N17 | 2'-OMe | 2'-MOE U | 2'-F | 2'-F | 2'-MOE |
| L17 | PS | PS | PS | PS | None |
| N18 | 2'-F | 2'-MOE U | 2'-F | 2'-OMe | None |
| L18 | PS | None | PS | PS | None |
| N19 | 2'-MOE U | None | 2'-MOE U | 2'-MOE A | None |
| L19 | PS | None | PS | PS | None |
| N20 | 2'-MOE U | None | 2'-MOE U | 2'-MOE A | None |

In the above, non-limiting examples:

Column A represents an oligomeric compound comprising a modified oligonucleotide consisting of 20 linked nucleosides, wherein the oligomeric compound comprises: a 5'-terminal group and 5'-terminal nucleoside of Formula II, IIa, IIb, or IIc; a region of alternating nucleosides; a region of alternating linkages; two 3'-terminal MOE nucleosides, each of which comprises a uracil base; and a region of six phosphorothioate linkages at the 3'-end.

Column B represents an oligomeric compound comprising a modified oligonucleotide consisting of 18 linked nucleosides, wherein the oligomeric compound comprises: a 5'-terminal group and 5'-terminal nucleoside of Formula II, IIa, IIb, or IIc; two 3'-terminal MOE nucleosides, each of which comprises a uracil base; and a region of six phosphorothioate linkages at the 3'-end.

Column C represents an oligomeric compound comprising a modified oligonucleotide consisting of 20 linked nucleosides, wherein the oligomeric compound comprises: a 5'-terminal group and 5'-terminal nucleoside of Formula II, IIa, IIb, or IIc; a region of uniformly modified 2'-F nucleosides; two 3'-terminal MOE nucleosides, each of which comprises a uracil base; and wherein each internucleoside linkage is a phosphorothioate linkage.

Column D represents an oligomeric compound comprising a modified oligonucleotide consisting of 20 linked nucleosides, wherein the oligomeric compound comprises: a 5'-terminal group and 5'-terminal nucleoside of Formula II, IIa, IIb, or IIc; a region of alternating 2'-OMe/2'-F nucleosides; a region of uniform 2'F nucleosides; a region of alternating phosphorothioate/phosphodiester linkages; two 3'-terminal MOE nucleosides, each of which comprises an adenine base; and a region of six phosphorothioate linkages at the 3'-end.

Column E represents an oligomeric compound comprising a modified oligonucleotide consisting of 17 linked nucleosides, wherein the oligomeric compound comprises: a 5'-terminal group and 5'-terminal nucleoside of Formula II, IIa, IIb, or IIc; three 3'-terminal MOE nucleosides.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation. It is also noted that the lengths of oligomeric compounds, such as those exemplified in the above tables, can be easily manipulated by lengthening or shortening one or more of the described regions, without disrupting the motif.

D. Certain Lengths

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides E. Certain Modified Oligonucleotides In certain embodiments, the above modifications and motifs (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a fully modified sugar motif may be modified or unmodified and may or may not follow the modification pattern of the sugar modifications. Likewise, such fully modified sugar motifs may comprise one or more modified nucleobase independent of the pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists if of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a fully modified sugar motif without further description may have any length, internucleoside linkage motif, and nucleobase motif. Unless otherwise indicated, all modifications are independent of nucleobase sequence.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

II. Certain Oligomeric Compounds

In certain embodiments, oligomeric compounds of the present invention are single-stranded. In certain embodiments, an oligomeric compound of the present invention hybridizes to a second oligomeric compound and forms a duplex. In certain embodiments, such duplexes are double-stranded antisense compounds. Such double-stranded antisense compounds comprise a first oligomeric compound having a region complementary to a target nucleic acid and a second oligomeric compound having a region complementary to the first oligomeric compound. The first oligomeric compound of such double-stranded antisense compounds typically comprises or consists of a modified oligonucleotide and optionally a terminal group or conjugate group. The oligonucleotide of the second oligomeric compound of such double-stranded antisense compound may be modified or unmodified. Either or both oligomeric compounds of a double-stranded antisense compound may comprise a terminal group or a conjugate group. The oligomeric compounds of double-stranded antisense compounds may include non-complementary overhanging nucleosides. Although certain oligomeric compounds of the present invention have particular use as single-stranded compounds, such compounds may also be paired with a second oligomeric compound to create a duplex. In such embodiments, the second oligomeric compound of the duplex may or may not be an oligomeric compound of the present invention.

In certain embodiments, oligomeric compounds of the present invention are single-stranded compounds that interact with a member of the RNA-induced silencing complex (RISC) and/or other member of the RNA interference pathway. Certain 5'-terminal groups, such as phosphorus moieties, described herein are suited for use in such single-stranded oligomeric compounds. In certain embodiments, 5'-terminal groups and 5'-terminal nucleosides of the present invention are resistant to nucleases. In certain embodiments, the motifs of the present invention are particularly suited for use in single-stranded oligomeric compounds.

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphorus moieties (both unmodified phosphorus moieties and modified phosphorus moieties), protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N. Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBSLett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes. In certain embodiments, lipid conjugates include palmityl, $C_{22}$ alkyl, $C_{20}$ alkyl, $C_{16}$ alkyl, $C_{10}$ alkyl, and $C_8$ alkyl.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Certain Antisense Activities

In certain embodiments, the present invention provides antisense compounds, which comprise or consist of an oligomeric compound comprising an antisense oligonucleotide, having a nucleobase sequence complementary to that of a target nucleic acid. In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprises a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain embodiments, the invention provides compounds and methods for antisense activity in a cell. In certain embodiments, the cell is in an animal. In certain embodiments, the animal is a human. In certain embodiments, the invention provides methods of administering a compound of the present invention to an animal to modulate one or more target nucleic acid.

In certain antisense activities, hybridization of an antisense compound to a target nucleic acid results in recruitment of a protein that cleaves the target nucleic acid. For example, certain antisense compounds or a portion of an antisense compound is loaded into an RNA-induced silencing complex (RISC), ultimately resulting in cleavage of the target nucleic acid.

In certain embodiments, hybridization of an antisense compound to a target nucleic acid does not result in cleavage of the target nucleic acid. In certain such embodiments, hybridization of the antisense compound to the target nucleic acid results in inhibition of formation of aggregates or foci that comprise the target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, a change in the number of aggregates or foci comprising the target nucleic acid, and/or a phenotypic change in a cell or animal.

IV. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a C9orf72 pre-mRNA. In certain embodiments, the C9orf72 pre-mRNA is a sense transcript. In certain embodiments, the C9orf72 pre-mRNA is an antisense transcript.

In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target region is completely within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism (SNP). In certain such embodiments, the antisense compound is capable of modulating expression of one allele of the SNP-containing target nucleic acid to a greater or lesser extent than it modulates another allele. In certain embodiments, an antisense compound hybridizes to a (SNP)-containing target nucleic acid at the single-nucleotide polymorphism site.

In certain embodiments, antisense compounds are at least partially complementary to more than one target nucleic acid. For example, antisense compounds of the present invention may mimic microRNAs, which typically bind to multiple targets.

A. Complementarity/Mismatches to the Target Nucleic Acid

In certain embodiments, antisense compounds comprise antisense oligonucleotides that are complementary to the target nucleic acid over the entire length of the oligonucleotide. In certain embodiments, such oligonucleotides are 99% complementary to a C9orf72 transcript. In certain embodiments, such oligonucleotides are 95% complementary to a C9orf72 transcript. In certain embodiments, such oligonucleotides are 90% complementary to a C9orf72 transcript. In certain embodiments, such oligonucleotides are 85% complementary to a C9orf72 transcript. In certain embodiments, such oligonucleotides are 80% complementary to a C9orf72 transcript. In certain embodiments, antisense oligonucleotides are at least 80% complementary to a C9orf72 transcript over the entire length of the oligonucleotide and comprise a region that is 100% or fully complementary to a C9orf72 transcript. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, the oligonucleotides of antisense compounds comprise one or more mismatched nucleobases relative to the target nucleic acid, e.g., a C9orf72 transcript. In certain such embodiments, antisense activity against the target is reduced by such mismatch, but activity against a non-target is reduced by a greater amount. Thus, in certain such embodiments selectivity of the antisense compound is improved. In certain embodiments, antisense activity against the target is increased by such mismatch. In certain such embodiments, the position or positions of the mismatch affect the antisense activity of the compound. In certain such embodiments, the mismatch is at position 21, 20, 19, 18, 17, 16, 15, 14, 13, 12, 11, 10, 9, 8, 7, 6, 5, 4, 3, 2, and/or 1 from the 5'-end of the oligonucleotide. In certain embodiments, the oligonucleotides of antisense compounds comprise two or more mismatches relative to the target nucleic acid.

V. Certain Pharmaceutical Compositions

In certain embodiments, the present invention provides pharmaceutical compositions comprising one or more antisense compound, oligomeric compound, and/or a salt thereof. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

In certain embodiments, pharmaceutical compositions comprise one or more or antisense compound and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an antisense compound encompass any pharmaceutically acceptable salts of the antisense compound, esters of the antisense compound, or salts of such esters. In certain embodiments, pharmaceutical compositions comprising antisense compounds comprising one or more antisense oligonucleotide, upon administration to an animal, including a human, are capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an antisense compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for intrathecal administration. In certain embodiments, a pharmaceutical composition is prepared for administration by injection (e.g., intravenous, subcutaneous, intramuscular, intrathecal etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

Nonlimiting Disclosure and Incorporation by Reference

All documents, or portions of documents, cited in this application, including, but not limited to, patents, patent applications, articles, books, GenBank accession numbers, and treatises, are hereby expressly incorporated by reference for the portions of the document discussed herein, as well as in their entirety. While certain compounds, compositions and methods described herein have been described with specificity in accordance with certain embodiments, such examples serve only to illustrate the compounds described herein and are not intended to limit the same.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or 3 such as for sugar anomers, or as (D) or (L), such as for amino acids, etc. Included in the compounds provided herein are all such possible isomers, including their racemic and optically pure forms, unless specified otherwise. Likewise, all cis- and trans-isomers, E and Z isomers, and tautomeric forms are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

Examples

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular modification appears at a particular position, other modifications at the same position are considered suitable, unless otherwise indicated.

Synthesis of Oligomeric Compounds

The oligonucleotides and oligomeric compounds provided herein can be prepared by any of the applicable techniques of organic synthesis. Many such techniques are well known in the art and described in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry*, in 9 Volumes, Barry M. Trost, Editor-in-Chief, Pergamon Press, New York, 1993; *Advanced Organic Chemistry*, Part B: Reactions and Synthesis, 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis*, 4th Edition, John Wiley & Sons, New York, 1991; and Larock, R. C., *Comprehensive Organic Transformations*, 2nd Edition, John Wiley & Sons, New York, 1999. Protocols for Oligonucleotides and Analogs, Agrawal, Ed., Humana Press, 1993, and/or RNA: Scaringe, Methods, 2001, 23, 206-217; Gait et al., *Applications of Chemically synthesized RNA in RNA:Protein Interactions*, Smith, Ed., 1998, 1-36; Gallo et al., *Tetrahedron*, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725, 677 and Re. 34,069. Additional methods applicable to synthesis of the compounds herein may be found in U.S. Pat. No. 8,993,738 and US 2014/0316121.

Example 1: Modified ss-siRNAs Complementary to the Hexanucleotide Repeat Region of a C9orf72 Transcript Modified oligonucleotides complementary to the hexanucleotide repeat region of human C9orf72 sense transcript or to the hexanucleotide repeat region of human C9orf72 antisense transcript are shown in the tables below. The nucleoside at the 5' end of each oligonucleotide and the two nucleosides at the 3' end of each oligonucleotide are not complementary to the target. In tables 1 and 5, the nucleosides at positions 2-19, e.g., the complementary region, of each oligonucleotide are 100% complementary to the target. In tables 2-4 and 6-8, the nucleosides at positions 2-19 of each oligonucleotide contain 1, 2, or 3 mismatches to the target. All of the mismatches, whether they are inside or outside of the complementary region, are underlined.

TABLE 1 ss-siRNAs 100% complementary to C9orf72 sense transcript at positions 2-19

| Isis No. | Sequence (5' to 3') | SEQ ID NO. |
| --- | --- | --- |
| 742036 | P-$\underline{T}_{es}G_{fs}G_{mo}C_{fs}C_{mo}C_{fs}C_{mo}G_{fs}G_{mo}C_{fs}C_{mo}C_{fs}C_{mo}G_{fs}G_{ms}C_{fs}C_{ms}C_{fs}C_{ms}\underline{A}_{es}A_{e}$ | 2 |
| 742037 | P-$\underline{T}_{es}C_{fs}G_{mo}G_{fs}C_{mo}C_{fs}C_{mo}C_{fs}G_{mo}G_{fs}C_{mo}C_{fs}C_{ms}G_{fs}C_{ms}C_{fs}C_{ms}\underline{A}_{es}A_{e}$ | 3 |
| 742038 | P-$\underline{T}_{es}C_{fs}C_{mo}G_{fs}G_{mo}C_{fs}C_{mo}C_{fs}C_{mo}G_{fs}G_{mo}C_{fs}C_{ms}C_{fs}C_{ms}G_{fs}G_{ms}C_{fs}C_{ms}\underline{A}_{es}A_{e}$ | 4 |
| 742039 | P-$\underline{T}_{es}C_{fs}C_{mo}C_{fs}G_{mo}G_{fs}C_{mo}C_{fs}C_{mo}C_{fs}G_{mo}G_{fs}C_{mo}C_{fs}C_{ms}C_{fs}C_{ms}G_{fs}G_{ms}C_{fs}C_{ms}\underline{A}_{es}A_{e}$ | 5 |
| 742040 | P-$\underline{T}_{es}C_{fs}C_{mo}C_{fs}C_{mo}G_{fs}G_{mo}C_{fs}C_{mo}C_{fs}C_{mo}G_{fs}G_{mo}C_{fs}C_{ms}C_{fs}C_{ms}G_{fs}G_{ms}\underline{A}_{es}A_{e}$ | 6 |
| 742041 | P-$\underline{T}_{es}G_{fs}C_{mo}C_{fs}C_{mo}C_{fs}G_{mo}G_{fs}C_{mo}C_{fs}C_{mo}C_{fs}G_{mo}G_{fs}C_{ms}C_{fs}C_{ms}C_{fs}G_{ms}\underline{A}_{es}A_{e}$ | 7 |

TABLE 2 ss-siRNAs with a single mismatch to C9orf72 sense transcript at positions 2-19

| Isis No. | Sequence (5' to 3') | SEQ ID NO. |
| --- | --- | --- |
| 742042 | P-$\underline{T}_{es}G_{fs}G_{mo}C_{fs}C_{mo}C_{fs}C_{mo}G_{fs}\underline{A}_{mo}C_{fs}C_{mo}C_{fs}C_{mo}G_{fs}G_{ms}C_{fs}C_{ms}C_{fs}C_{ms}\underline{A}_{es}A_{e}$ | 8 |
| 742043 | P-$\underline{T}_{es}C_{fs}G_{mo}G_{fs}C_{mo}C_{fs}C_{mo}C_{fs}\underline{A}_{mo}G_{fs}C_{mo}C_{fs}C_{mo}C_{fs}G_{ms}C_{fs}C_{ms}C_{fs}C_{ms}\underline{A}_{es}A_{e}$ | 9 |
| 742044 | P-$\underline{T}_{es}C_{fs}C_{mo}G_{fs}G_{mo}C_{fs}C_{mo}C_{fs}\underline{A}_{mo}G_{fs}G_{mo}C_{fs}C_{mo}C_{fs}C_{ms}G_{fs}G_{ms}C_{fs}C_{ms}\underline{A}_{es}A_{e}$ | 10 |
| 742045 | P-$\underline{T}_{es}C_{fs}C_{mo}C_{fs}G_{mo}G_{fs}C_{mo}C_{fs}\underline{A}_{mo}C_{fs}G_{mo}G_{fs}C_{mo}C_{fs}C_{ms}C_{fs}C_{ms}G_{fs}G_{ms}C_{fs}C_{ms}\underline{A}_{es}A_{e}$ | 11 |
| 742046 | P-$\underline{T}_{es}C_{fs}C_{mo}C_{fs}C_{mo}G_{fs}G_{mo}C_{fs}\underline{A}_{mo}C_{fs}C_{mo}G_{fs}G_{mo}C_{fs}C_{ms}C_{fs}C_{ms}G_{fs}G_{ms}\underline{A}_{es}A_{e}$ | 12 |
| 742047 | P-$\underline{T}_{es}G_{fs}C_{mo}C_{fs}C_{mo}C_{fs}G_{mo}G_{fs}\underline{A}_{mo}C_{fs}C_{mo}C_{fs}G_{mo}G_{fs}C_{ms}C_{fs}C_{ms}C_{fs}G_{ms}\underline{A}_{es}A_{e}$ | 13 |

TABLE 3 ss-siRNAs with two mismatches to C9orf72 sense transcript at positions 2-19

| Isis No. | Sequence (5' to 3') | SEQ ID NO. |
| --- | --- | --- |
| 742054 | P-$\underline{T}_{es}G_{fs}G_{mo}C_{fs}C_{mo}C_{fs}C_{mo}G_{fs}\underline{A}_{mo}C_{fs}C_{mo}C_{fs}C_{mo}\underline{A}_{fs}G_{ms}C_{fs}C_{ms}C_{fs}C_{ms}\underline{A}_{es}A_{e}$ | 14 |
| 742055 | P-$\underline{T}_{es}C_{fs}G_{mo}G_{fs}C_{mo}C_{fs}C_{mo}C_{fs}\underline{A}_{mo}G_{fs}C_{mo}C_{fs}C_{mo}\underline{A}_{fs}G_{ms}C_{fs}C_{ms}C_{fs}C_{ms}\underline{A}_{es}A_{e}$ | 15 |
| 742056 | P-$\underline{T}_{es}C_{fs}C_{mo}G_{fs}G_{mo}C_{fs}C_{mo}C_{fs}\underline{A}_{mo}G_{fs}G_{mo}C_{fs}\underline{A}_{fs}C_{ms}G_{fs}G_{ms}C_{fs}C_{ms}\underline{A}_{es}A_{e}$ | 16 |
| 742057 | P-$\underline{T}_{es}C_{fs}C_{mo}C_{fs}G_{mo}G_{fs}C_{mo}C_{fs}\underline{A}_{mo}C_{fs}G_{mo}G_{fs}C_{mo}\underline{A}_{fs}C_{ms}C_{fs}G_{ms}G_{fs}C_{ms}\underline{A}_{es}A_{e}$ | 17 |
| 742058 | P-$\underline{T}_{es}C_{fs}C_{mo}C_{fs}C_{mo}G_{fs}G_{mo}C_{fs}\underline{A}_{mo}C_{fs}C_{mo}G_{fs}G_{mo}\underline{A}_{fs}C_{ms}C_{fs}G_{ms}G_{fs}G_{ms}\underline{A}_{es}A_{e}$ | 18 |
| 742059 | P-$\underline{T}_{es}G_{fs}C_{mo}C_{fs}C_{mo}C_{fs}G_{mo}G_{fs}\underline{A}_{mo}C_{fs}C_{mo}C_{fs}G_{mo}\underline{A}_{fs}G_{ms}C_{fs}C_{ms}C_{fs}C_{ms}\underline{A}_{es}A_{e}$ | 19 |

TABLE 4 ss-siRNAs with three mismatches to C9orf72 sense transcript at positions 2-19

| Isis No. | Sequence (5' to 3') | SEQ ID NO. |
| --- | --- | --- |
| 742048 | P-$\underline{T}_{es}G_{fs}G_{mo}C_{fs}C_{mo}C_{fs}C_{mo}G_{fs}\underline{A}_{mo}\underline{A}_{fs}\underline{A}_{mo}C_{fs}C_{mo}G_{fs}G_{ms}C_{fs}C_{ms}C_{fs}C_{ms}\underline{A}_{es}A_{e}$ | 20 |
| 742049 | P-$\underline{T}_{es}C_{fs}G_{mo}G_{fs}C_{mo}C_{fs}C_{mo}C_{fs}\underline{A}_{mo}\underline{A}_{fs}\underline{A}_{mo}C_{fs}C_{mo}C_{fs}G_{ms}C_{fs}C_{ms}C_{fs}C_{ms}\underline{A}_{es}A_{e}$ | 21 |
| 742050 | P-$\underline{T}_{es}C_{fs}C_{mo}G_{fs}G_{mo}C_{fs}C_{mo}C_{fs}\underline{A}_{mo}\underline{A}_{fs}\underline{A}_{mo}C_{fs}C_{mo}C_{fs}C_{ms}G_{fs}G_{ms}C_{fs}C_{ms}\underline{A}_{es}A_{e}$ | 22 |
| 742051 | P-$\underline{T}_{es}C_{fs}C_{mo}C_{fs}G_{mo}G_{fs}C_{mo}C_{fs}\underline{A}_{mo}\underline{A}_{fs}\underline{A}_{mo}G_{fs}C_{mo}C_{fs}C_{ms}C_{fs}G_{ms}G_{fs}C_{ms}\underline{A}_{es}A_{e}$ | 23 |

TABLE 4-continued ss-siRNAs with three mismatches to C9orf72 sense transcript at positions 2-19

| Isis No. | Sequence (5' to 3') | SEQ ID NO. |
|---|---|---|
| 742052 | P-$\underline{T}_{es}C_{fs}C_{mo}C_{fs}C_{mo}G_{fs}G_{mo}G_{fs}\underline{A}_{mo}\underline{A}_{fs}\underline{A}_{mo}G_{fs}G_{mo}C_{fs}C_{ms}C_{fs}C_{ms}G_{fs}G_{m}\underline{A}_{es}\underline{A}_{e}$ | 24 |
| 742053 | P-$\underline{T}_{es}G_{fs}C_{mo}C_{fs}C_{mo}C_{fs}G_{mo}G_{fs}\underline{A}_{mo}\underline{A}_{fs}\underline{A}_{mo}C_{fs}G_{mo}G_{fs}C_{ms}C_{fs}C_{ms}G_{m}\underline{A}_{es}\underline{A}_{e}$ | 25 |

TABLE 5 ss-siRNAs 100% complementary to C9orf72 antisense transcript at positions 2-19

| Isis No. | Sequence (5' to 3') | SEQ ID NO. |
|---|---|---|
| 742060 | P-$\underline{T}_{es}G_{fs}G_{mo}G_{fs}G_{mo}C_{fs}C_{mo}G_{fs}G_{mo}G_{fs}G_{mo}C_{fs}C_{mo}G_{fs}G_{ms}G_{fs}G_{ms}C_{fs}C_{m}\underline{A}_{es}\underline{A}_{e}$ | 26 |
| 742061 | P-$\underline{T}_{es}C_{fs}G_{mo}G_{fs}G_{mo}C_{fs}C_{mo}G_{fs}G_{mo}G_{fs}G_{mo}C_{fs}C_{ms}G_{fs}G_{ms}G_{fs}C_{m}\underline{A}_{es}\underline{A}_{e}$ | 27 |
| 742062 | P-$\underline{T}_{es}C_{fs}C_{mo}G_{fs}G_{mo}G_{fs}G_{mo}C_{fs}C_{mo}G_{fs}G_{mo}G_{fs}G_{mo}C_{fs}C_{ms}G_{fs}G_{ms}G_{m}\underline{A}_{es}\underline{A}_{e}$ | 28 |
| 742063 | P-$\underline{T}_{es}G_{fs}C_{mo}C_{fs}G_{mo}G_{fs}G_{mo}C_{fs}C_{mo}G_{fs}G_{mo}G_{fs}G_{ms}C_{fs}C_{ms}G_{m}\underline{A}_{es}\underline{A}_{e}$ | 29 |
| 742064 | P-$\underline{T}_{es}G_{fs}G_{mo}C_{fs}C_{mo}G_{fs}G_{mo}G_{fs}G_{mo}C_{fs}C_{mo}G_{fs}G_{ms}G_{fs}C_{ms}C_{fs}G_{m}\underline{A}_{es}\underline{A}_{e}$ | 30 |
| 742065 | P-$\underline{T}_{es}G_{fs}G_{mo}G_{fs}C_{mo}C_{fs}G_{mo}G_{fs}G_{mo}G_{fs}C_{mo}C_{fs}G_{mo}G_{fs}G_{ms}C_{fs}C_{ms}G_{m}\underline{A}_{es}\underline{A}_{e}$ | 31 |

TABLE 6 ss-siRNAs with a single mismatch to C9orf72 antisense transcript at positions 2-19

| Isis No. | Sequence (5' to 3') | SEQ ID NO. |
|---|---|---|
| 742066 | P-$\underline{T}_{es}G_{fs}G_{mo}G_{fs}G_{mo}C_{fs}C_{mo}G_{fs}\underline{A}_{mo}G_{fs}G_{mo}C_{fs}C_{mo}G_{fs}G_{ms}G_{fs}G_{ms}C_{fs}C_{m}\underline{A}_{es}\underline{A}_{e}$ | 32 |
| 742067 | P-$\underline{T}_{es}C_{fs}G_{mo}G_{fs}G_{mo}C_{fs}C_{mo}G_{fs}\underline{A}_{mo}G_{fs}G_{mo}C_{fs}C_{mo}G_{fs}G_{ms}G_{fs}G_{ms}C_{fs}C_{m}\underline{A}_{es}\underline{A}_{e}$ | 33 |
| 742068 | P-$\underline{T}_{es}C_{fs}C_{mo}G_{fs}G_{mo}G_{fs}G_{mo}C_{fs}\underline{A}_{mo}C_{fs}G_{mo}G_{fs}G_{mo}C_{fs}C_{ms}G_{fs}G_{ms}G_{fs}G_{m}\underline{A}_{es}\underline{A}_{e}$ | 34 |
| 742069 | P-$\underline{T}_{es}G_{fs}C_{mo}C_{fs}G_{mo}G_{fs}G_{mo}C_{fs}\underline{A}_{mo}C_{fs}G_{mo}G_{fs}G_{mo}G_{fs}C_{ms}C_{fs}G_{ms}G_{m}\underline{A}_{es}\underline{A}_{e}$ | 35 |
| 742070 | P-$\underline{T}_{es}G_{fs}G_{mo}C_{fs}C_{mo}G_{fs}G_{mo}G_{fs}\underline{A}_{mo}C_{fs}G_{mo}G_{fs}G_{mo}G_{fs}G_{ms}C_{fs}C_{ms}G_{fs}G_{m}\underline{A}_{es}\underline{A}_{e}$ | 36 |
| 742071 | P-$\underline{T}_{es}G_{fs}G_{mo}G_{fs}C_{mo}C_{fs}G_{mo}G_{fs}\underline{A}_{mo}G_{fs}C_{mo}C_{fs}G_{mo}G_{fs}G_{ms}G_{fs}C_{ms}C_{fs}G_{m}\underline{A}_{es}\underline{A}_{e}$ | 37 |

TABLE 7 ss-siRNAs with two mismatches to C9orf72 antisense transcript at positions 2-19

| Isis No. | Sequence (5' to 3') | SEQ ID NO. |
|---|---|---|
| 742078 | P-$\underline{T}_{es}G_{fs}G_{mo}G_{fs}G_{mo}C_{fs}C_{mo}G_{fs}\underline{A}_{mo}G_{fs}G_{mo}C_{fs}C_{mo}\underline{A}_{fs}G_{ms}G_{fs}G_{ms}C_{fs}C_{m}\underline{A}_{es}\underline{A}_{e}$ | 38 |
| 742079 | P-$\underline{T}_{es}C_{fs}G_{mo}G_{fs}G_{mo}C_{fs}C_{mo}G_{fs}\underline{A}_{mo}G_{fs}G_{mo}C_{fs}C_{mo}\underline{A}_{fs}G_{ms}G_{fs}G_{ms}C_{fs}C_{m}\underline{A}_{es}\underline{A}_{e}$ | 39 |
| 742080 | P-$\underline{T}_{es}C_{fs}C_{mo}G_{fs}G_{mo}G_{fs}G_{mo}C_{fs}\underline{A}_{mo}C_{fs}G_{mo}G_{fs}G_{mo}\underline{A}_{fs}C_{ms}G_{fs}G_{ms}G_{fs}G_{m}\underline{A}_{es}\underline{A}_{e}$ | 40 |
| 742081 | P-$\underline{T}_{es}G_{fs}C_{mo}C_{fs}G_{mo}G_{fs}G_{mo}C_{fs}\underline{A}_{mo}C_{fs}G_{mo}G_{fs}G_{mo}\underline{A}_{fs}C_{ms}C_{fs}G_{ms}G_{fs}G_{m}\underline{A}_{es}\underline{A}_{e}$ | 41 |
| 742082 | P-$\underline{T}_{es}G_{fs}G_{mo}C_{fs}C_{mo}G_{fs}G_{mo}G_{fs}\underline{A}_{mo}C_{fs}G_{mo}G_{fs}G_{mo}\underline{A}_{fs}C_{ms}C_{fs}G_{ms}G_{fs}G_{m}\underline{A}_{es}\underline{A}_{e}$ | 42 |
| 742083 | P-$\underline{T}_{es}G_{fs}G_{mo}G_{fs}C_{mo}C_{fs}G_{mo}G_{fs}\underline{A}_{mo}G_{fs}C_{mo}C_{fs}G_{mo}\underline{A}_{fs}G_{ms}G_{fs}C_{ms}C_{fs}G_{m}\underline{A}_{es}\underline{A}_{e}$ | 43 |

TABLE 8 ss-siRNAs with three mismatches to C9orf72 antisense transcript at positions 2-19

| Isis No. | Sequence (5' to 3') | SEQ ID NO. |
|---|---|---|
| 742072 | P-$T_{es}G_{fs}G_{mo}G_{fs}G_{mo}C_{fs}C_{mo}G_{fs}\underline{A}_{mo}\underline{A}_{fs}\underline{A}_{mo}C_{fs}C_{mo}G_{fs}G_{ms}G_{fs}G_{ms}C_{fs}C_{m}\underline{A}_{es}\underline{A}_{e}$ | 44 |
| 742073 | P-$T_{es}C_{fs}G_{mo}G_{fs}G_{mo}G_{fs}C_{mo}C_{fs}\underline{A}_{mo}\underline{A}_{fs}\underline{A}_{mo}G_{fs}C_{mo}C_{fs}G_{ms}G_{fs}G_{ms}C_{fs}C_{m}\underline{A}_{es}\underline{A}_{e}$ | 45 |
| 742074 | P-$T_{es}C_{fs}C_{mo}G_{fs}G_{mo}G_{fs}G_{mo}C_{fs}\underline{A}_{mo}\underline{A}_{fs}\underline{A}_{mo}G_{fs}G_{mo}C_{fs}C_{ms}G_{fs}G_{ms}G_{fs}G_{m}\underline{A}_{es}\underline{A}_{e}$ | 46 |
| 742075 | P-$T_{es}G_{fs}C_{mo}C_{fs}G_{mo}G_{fs}G_{mo}G_{fs}\underline{A}_{mo}\underline{A}_{fs}\underline{A}_{mo}G_{fs}G_{mo}G_{fs}C_{ms}C_{fs}G_{ms}G_{fs}G_{m}\underline{A}_{es}\underline{A}_{e}$ | 47 |
| 742076 | P-$T_{es}G_{fs}G_{mo}C_{fs}C_{mo}G_{fs}G_{mo}G_{fs}\underline{A}_{mo}\underline{A}_{fs}\underline{A}_{mo}G_{fs}G_{mo}G_{fs}G_{ms}C_{fs}C_{ms}G_{fs}G_{m}\underline{A}_{es}\underline{A}_{e}$ | 48 |
| 742077 | P-$T_{es}G_{fs}G_{mo}G_{fs}C_{mo}C_{fs}G_{mo}G_{fs}\underline{A}_{mo}\underline{A}_{fs}\underline{A}_{mo}C_{fs}G_{mo}G_{fs}G_{ms}G_{fs}C_{ms}C_{fs}G_{m}\underline{A}_{es}\underline{A}_{e}$ | 49 |

Subscripts: "s" indicates a phosphorothioate internucleoside linkage; "o" indicates an unmodified, phosphate internucleoside linkage; "f" indicates a 2'-fluoro modified nucleoside; "m" indicates a 2'-O-methyl modified nucleoside; and "e" indicates a 2'-O-methoxyethyl (MOE) modified nucleoside. "P" at the 5'-end indicates a terminal phosphate group at the 5'-position.

Example 2: Inhibitory Effects of Modified ss-siRNAs on C9orf72 Foci In Vitro

Modified oligonucleotides described in Example 1 were tested for their effects on C9orf72 foci in ALS/FTD patient fibroblast cell lines. The fibroblast cells were plated at a density of 10,000 cells per well into Lab-Tek 8-well chambered cover glass slides. One day later, Isis No. 742048, 742054, 742072, or 742078 was added, or a control. The "CM" negative control is an oligonucleotide with a sequence that is not complementary to a C9orf72 transcript. The "siRNA" positive control is a siRNA that is complementary to a C9orf72 transcript. Two days after oligonucleotide treatment, cells were fixed with 4% formaldehyde in 1×PBS and permeabilized in 70% ethanol at 4° C. overnight. Cells were washed with Wash Buffer (10% formamide in 2×SSC) for 5 minutes, and then incubated with pre-hybridization buffer (40% formamide in 2×SSC) at 60° C. for 20 minutes. A $(CCCCGG)_4$-Cy3 DNA probe or a $(GGGGCC)_{3.3}$-Cy3 probe in Hybridization Buffer (100 mg/mL dextran sulfate and 40% formamide in 2×SSC) was added. The slide was placed in a humidified chamber and incubated in the dark at 37° C. overnight. The next day, cells were washed twice with wash buffer at 37° C., then stained with mounting media and DAPI (Vector Labs, H-1500).

Cells were imaged at 60× magnification using a Widefield Deltavision microscope. Images were processed by blind deconvolution with AutoQuant X3 and ImageJ. For quantification, at least 20 pictures were taken from randomly chosen microscopic fields, containing 100-300 cells for each treatment. The average percentage of the total number of cells containing RNA foci and the number of foci per 100 cells was calculated for each oligonucleotide treatment. The results, shown in FIGS. 1A-D, indicate that the modified oligonucleotides targeting the C9orf72 sense transcript decreased the number of C9orf72 sense foci, and the modified oligonucleotides targeting the C9orf72 antisense transcript decreased the number of C9orf72 antisense foci. Furthermore, most of the modified oligonucleotides decreased C9orf72 foci to a greater extent than the "siRNA" positive control.

Example 3: Inhibitory Effect of Modified ss-siRNAs on C9orf72 Expression In Vivo The modified ss-siRNAs targeting the hexanucleotide repeat region of C9orf72, listed below, are evaluated for their ability to inhibit C9orf72 expression in mice. Transgenic mice are injected subcutaneously with one of the modified ss-siRNAs, listed below, or with saline as a control. Each treatment group will include 4 animals. Each mouse is treated with one of the following dosing regimens: (1) Dose of 10 mg/kg administered as a single dose of 10 mg/kg; (2) Dose of 25 mg/kg administered as a single dose of 25 mg/kg; (3) Dose of 100 mg/kg administered as a series of doses of 25 mg/kg given twice a day for two days (for a total of 100 mg/kg); (4) Dose of 300 mg/kg administered as a series of doses of 25 mg/kg given twice a day for six days (for a total of 300 mg/kg).

Seventy-two hours after the administration of the last dose, the mice are sacrificed and tissue is collected for analysis. C9orf72 mRNA levels in liver are determined using real-time PCR and according to standard protocols and C9orf72 mRNA levels are determined relative to total RNA (using Cyclophilin), prior to normalization to PBS-treated control. C9orf72 protein levels are measured using standard Western blot analysis (immunoblot analysis). C9orf72 foci were also measured, as described in Example 2, in sections of the collected tissues.

TABLE 9 ss-siRNAs 100% complementary to C9orf72 sense transcript at positions 2-19

| Isis No. | Sequence (5' to 3') | SEQ ID NO. |
|---|---|---|
| 748438 | Pv-$T_{es}G_{fs}G_{mo}C_{fs}C_{mo}C_{fs}C_{mo}G_{fs}G_{mo}C_{fs}C_{mo}C_{fs}C_{mo}G_{fs}G_{ms}C_{fs}C_{ms}C_{fs}C_{ms}\underline{A}_{es}\underline{A}_{e}$ | 2 |
| 748439 | Pv-$T_{es}C_{fs}G_{mo}G_{fs}C_{mo}C_{fs}C_{mo}C_{fs}G_{mo}G_{fs}C_{mo}C_{fs}C_{mo}C_{fs}G_{ms}G_{fs}C_{ms}C_{fs}C_{ms}\underline{A}_{es}\underline{A}_{e}$ | 3 |
| 748440 | Pv-$T_{es}C_{fs}C_{mo}G_{fs}G_{mo}C_{fs}C_{mo}C_{fs}C_{mo}G_{fs}G_{mo}C_{fs}C_{mo}C_{fs}C_{ms}G_{fs}G_{ms}C_{fs}C_{ms}\underline{A}_{es}\underline{A}_{e}$ | 4 |
| 748441 | Pv-$T_{es}C_{fs}C_{mo}C_{fs}G_{mo}G_{fs}C_{mo}C_{fs}C_{mo}C_{fs}G_{mo}G_{fs}C_{mo}C_{fs}C_{ms}C_{fs}G_{ms}G_{fs}C_{ms}\underline{A}_{es}\underline{A}_{e}$ | 5 |

TABLE 9-continued ss-siRNAs 100% complementary to C9orf72 sense transcript at positions 2-19

| Isis No. | Sequence (5' to 3') | SEQ ID NO. |
|---|---|---|
| 748442 | Pv-$\underline{T}_{es}C_{fs}C_{mo}C_{fs}C_{mo}G_{fs}G_{mo}C_{fs}C_{mo}C_{fs}C_{mo}G_{fs}G_{mo}C_{fs}C_{ms}C_{fs}C_{ms}G_{fs}G_{ms}\underline{A}_{es}\underline{A}_{e}$ | 6 |
| 748443 | Pv-$\underline{T}_{es}C_{fs}G_{mo}C_{fs}C_{mo}C_{fs}G_{mo}G_{fs}C_{mo}C_{fs}C_{mo}C_{fs}G_{mo}G_{fs}C_{ms}C_{fs}C_{ms}C_{fs}G_{ms}\underline{A}_{es}\underline{A}_{e}$ | 7 |

TABLE 10 ss-siRNAs with a single mismatch to C9orf72 sense transcript at positions 2-19

| Isis No. | Sequence (5' to 3') | SEQ ID NO. |
|---|---|---|
| 748444 | Pv-$\underline{T}_{es}G_{fs}G_{mo}C_{fs}C_{mo}C_{fs}C_{mo}G_{fs}\underline{A}_{mo}C_{fs}C_{mo}C_{fs}C_{mo}G_{fs}G_{ms}C_{fs}C_{ms}C_{fs}C_{ms}\underline{A}_{es}\underline{A}_{e}$ | 8 |
| 748445 | Pv-$\underline{T}_{es}C_{fs}G_{mo}G_{fs}C_{mo}C_{fs}C_{mo}C_{fs}\underline{A}_{mo}G_{fs}C_{mo}C_{fs}C_{mo}C_{fs}G_{ms}G_{fs}C_{ms}C_{fs}C_{ms}\underline{A}_{es}\underline{A}_{e}$ | 9 |
| 748446 | Pv-$\underline{T}_{es}C_{fs}C_{mo}G_{fs}G_{mo}C_{fs}C_{mo}C_{fs}\underline{A}_{mo}G_{fs}G_{mo}C_{fs}C_{mo}C_{fs}C_{ms}G_{fs}G_{ms}C_{fs}C_{ms}\underline{A}_{es}\underline{A}_{e}$ | 10 |
| 748447 | Pv-$\underline{T}_{es}C_{fs}C_{mo}C_{fs}G_{mo}G_{fs}C_{mo}C_{fs}\underline{A}_{mo}C_{fs}G_{mo}G_{fs}C_{mo}C_{fs}C_{ms}C_{fs}C_{ms}G_{fs}G_{ms}\underline{A}_{es}\underline{A}_{e}$ | 11 |
| 748448 | Pv-$\underline{T}_{es}C_{fs}C_{mo}C_{fs}C_{mo}G_{fs}G_{mo}C_{fs}\underline{A}_{mo}C_{fs}C_{mo}G_{fs}G_{mo}C_{fs}C_{ms}C_{fs}C_{ms}G_{fs}G_{ms}\underline{A}_{es}\underline{A}_{e}$ | 12 |
| 748449 | Pv-$\underline{T}_{es}G_{fs}C_{mo}C_{fs}C_{mo}C_{fs}G_{mo}G_{fs}\underline{A}_{mo}C_{fs}C_{mo}C_{fs}G_{mo}G_{fs}C_{ms}C_{fs}C_{ms}C_{fs}G_{ms}\underline{A}_{es}\underline{A}_{e}$ | 13 |

TABLE 11 ss-siRNAs with two mismatches to C9orf72 sense transcript at positions 2-19

| Isis No. | Sequence (5' to 3') | SEQ ID NO. |
|---|---|---|
| 748456 | Pv-$\underline{T}_{es}G_{fs}G_{mo}C_{fs}C_{mo}C_{fs}C_{mo}G_{fs}\underline{A}_{mo}C_{fs}C_{mo}C_{fs}C_{mo}\underline{A}_{fs}G_{ms}C_{fs}C_{ms}C_{fs}C_{ms}\underline{A}_{es}\underline{A}_{e}$ | 14 |
| 748457 | Pv-$\underline{T}_{es}C_{fs}G_{mo}G_{fs}C_{mo}C_{fs}C_{mo}C_{fs}\underline{A}_{mo}G_{fs}C_{mo}C_{fs}C_{mo}\underline{A}_{fs}G_{ms}C_{fs}C_{ms}C_{fs}C_{ms}\underline{A}_{es}\underline{A}_{e}$ | 15 |
| 748458 | Pv-$\underline{T}_{es}C_{fs}C_{mo}G_{fs}G_{mo}G_{fs}C_{mo}C_{fs}\underline{A}_{mo}C_{fs}G_{mo}G_{fs}G_{mo}C_{fs}C_{ms}C_{fs}C_{ms}G_{fs}G_{ms}\underline{A}_{es}\underline{A}_{e}$ | 17 |
| 748459 | Pv-$\underline{T}_{es}C_{fs}C_{mo}C_{fs}C_{mo}G_{fs}G_{mo}C_{fs}\underline{A}_{mo}C_{fs}C_{mo}G_{fs}G_{mo}C_{fs}\underline{A}_{ms}C_{fs}C_{ms}G_{fs}G_{ms}\underline{A}_{es}\underline{A}_{e}$ | 18 |
| 748460 | Pv-$\underline{T}_{es}C_{fs}C_{mo}C_{fs}C_{mo}C_{fs}G_{mo}G_{fs}\underline{A}_{mo}C_{fs}C_{mo}C_{fs}G_{mo}\underline{A}_{fs}C_{ms}C_{fs}C_{ms}C_{fs}G_{ms}\underline{A}_{es}\underline{A}_{e}$ | 19 |
| n/a | Pv-$\underline{T}_{es}C_{fs}C_{mo}G_{fs}G_{mo}C_{fs}C_{mo}C_{fs}\underline{A}_{mo}G_{fs}G_{mo}C_{fs}C_{mo}\underline{A}_{fs}C_{ms}G_{fs}G_{ms}C_{fs}C_{ms}\underline{A}_{es}\underline{A}_{e}$ | 19 |

TABLE 12 ss-siRNAs with three mismatches to C9orf72 sense transcript at positions 2-19

| Isis No. | Sequence (5' to 3') | SEQ ID NO. |
|---|---|---|
| 748450 | Pv-$\underline{T}_{es}G_{fs}G_{mo}C_{fs}C_{mo}C_{fs}C_{mo}G_{fs}\underline{A}_{mo}\underline{A}_{fs}\underline{A}_{mo}C_{fs}C_{mo}C_{fs}G_{ms}C_{fs}C_{ms}C_{fs}C_{ms}\underline{A}_{es}\underline{A}_{e}$ | 20 |
| 748451 | Pv-$\underline{T}_{es}C_{fs}G_{mo}G_{fs}C_{mo}C_{fs}C_{mo}C_{fs}\underline{A}_{mo}\underline{A}_{fs}\underline{A}_{mo}C_{fs}C_{mo}C_{fs}G_{ms}G_{fs}C_{ms}C_{fs}C_{ms}\underline{A}_{es}\underline{A}_{e}$ | 21 |
| 748452 | Pv-$\underline{T}_{es}C_{fs}C_{mo}G_{fs}G_{mo}C_{fs}C_{mo}C_{fs}\underline{A}_{mo}\underline{A}_{fs}\underline{A}_{mo}C_{fs}C_{mo}C_{fs}C_{ms}G_{fs}G_{ms}C_{fs}C_{ms}\underline{A}_{es}\underline{A}_{e}$ | 22 |
| 748453 | Pv-$\underline{T}_{es}C_{fs}C_{mo}C_{fs}G_{mo}G_{fs}C_{mo}C_{fs}\underline{A}_{mo}\underline{A}_{fs}\underline{A}_{mo}G_{fs}C_{mo}C_{fs}C_{ms}C_{fs}C_{ms}G_{fs}G_{ms}\underline{A}_{es}\underline{A}_{e}$ | 23 |
| 748454 | Pv-$\underline{T}_{es}C_{fs}C_{mo}C_{fs}C_{mo}G_{fs}G_{mo}C_{fs}\underline{A}_{mo}\underline{A}_{fs}\underline{A}_{mo}G_{fs}G_{mo}C_{fs}C_{ms}C_{fs}C_{ms}G_{fs}G_{ms}\underline{A}_{es}\underline{A}_{e}$ | 24 |
| 748455 | Pv-$\underline{T}_{es}G_{fs}C_{mo}C_{fs}C_{mo}C_{fs}G_{mo}G_{fs}\underline{A}_{mo}\underline{A}_{fs}\underline{A}_{mo}C_{fs}G_{mo}G_{fs}C_{ms}C_{fs}C_{ms}C_{fs}G_{ms}\underline{A}_{es}\underline{A}_{e}$ | 25 |

TABLE 13 ss-siRNAs 100% complementary to C9orf72 antisense transcript at positions 2-19

| Isis No. | Sequence (5' to 3') | SEQ ID NO. |
|---|---|---|
| 748461 | Pv-$\underline{T}_{es}G_{fs}G_{mo}G_{fs}G_{mo}C_{fs}C_{mo}G_{fs}G_{mo}G_{fs}G_{mo}C_{fs}C_{mo}G_{fs}G_{ms}G_{fs}G_{ms}C_{fs}C_{ms}\underline{A}_{es}\underline{A}_{e}$ | 26 |
| 748462 | Pv-$\underline{T}_{es}C_{fs}G_{mo}G_{fs}G_{mo}G_{fs}C_{mo}C_{fs}G_{mo}G_{fs}G_{mo}G_{fs}C_{mo}C_{fs}G_{ms}G_{fs}G_{ms}G_{fs}C_{ms}\underline{A}_{es}\underline{A}_{e}$ | 27 |
| 748463 | Pv-$\underline{T}_{es}C_{fs}C_{mo}G_{fs}G_{mo}G_{fs}G_{mo}C_{fs}C_{mo}G_{fs}G_{mo}G_{fs}G_{mo}C_{fs}C_{ms}G_{fs}G_{ms}G_{fs}G_{ms}\underline{A}_{es}\underline{A}_{e}$ | 28 |
| 748464 | Pv-$\underline{T}_{es}C_{fs}C_{mo}C_{fs}G_{mo}G_{fs}G_{mo}G_{fs}C_{mo}C_{fs}G_{mo}G_{fs}G_{mo}G_{fs}C_{ms}C_{fs}G_{ms}G_{fs}G_{ms}\underline{A}_{es}\underline{A}_{e}$ | 29 |
| 748465 | Pv-$\underline{T}_{es}G_{fs}G_{mo}C_{fs}C_{mo}C_{fs}G_{mo}G_{fs}G_{mo}G_{fs}C_{mo}C_{fs}G_{mo}G_{fs}G_{ms}G_{fs}C_{ms}C_{fs}G_{ms}\underline{A}_{es}\underline{A}_{e}$ | 30 |
| 748466 | Pv-$\underline{T}_{es}G_{fs}G_{mo}G_{fs}C_{mo}C_{fs}C_{mo}G_{fs}G_{mo}G_{fs}G_{mo}C_{fs}C_{mo}G_{fs}G_{ms}G_{fs}C_{ms}C_{fs}G_{ms}\underline{A}_{es}\underline{A}_{e}$ | 31 |

TABLE 14 ss-siRNAs with a single mismatch to C9orf72 antisense transcript at positions 2-19

| Isis No. | Sequence (5' to 3') | SEQ ID NO. |
|---|---|---|
| 748467 | Pv-$\underline{T}_{es}G_{fs}G_{mo}G_{fs}G_{mo}C_{fs}C_{mo}G_{fs}\underline{A}_{mo}G_{fs}G_{mo}C_{fs}C_{mo}G_{fs}G_{ms}G_{fs}G_{ms}C_{fs}C_{ms}\underline{A}_{es}\underline{A}_{e}$ | 32 |
| 748468 | Pv-$\underline{T}_{es}C_{fs}G_{mo}G_{fs}G_{mo}G_{fs}C_{mo}C_{fs}\underline{A}_{mo}G_{fs}G_{mo}G_{fs}C_{mo}C_{fs}G_{ms}G_{fs}G_{ms}G_{fs}C_{ms}\underline{A}_{es}\underline{A}_{e}$ | 33 |
| 748469 | Pv-$\underline{T}_{es}C_{fs}C_{mo}G_{fs}G_{mo}G_{fs}G_{mo}C_{fs}\underline{A}_{mo}G_{fs}G_{mo}G_{fs}G_{mo}C_{fs}C_{ms}G_{fs}G_{ms}G_{fs}G_{ms}\underline{A}_{es}\underline{A}_{e}$ | 34 |
| 748470 | Pv-$\underline{T}_{es}C_{fs}C_{mo}C_{fs}G_{mo}G_{fs}G_{mo}G_{fs}\underline{A}_{mo}C_{fs}G_{mo}G_{fs}G_{mo}G_{fs}C_{ms}C_{fs}G_{ms}G_{fs}G_{ms}\underline{A}_{es}\underline{A}_{e}$ | 35 |
| 748471 | Pv-$\underline{T}_{es}G_{fs}G_{mo}C_{fs}C_{mo}C_{fs}G_{mo}G_{fs}\underline{A}_{mo}C_{fs}C_{mo}G_{fs}G_{mo}G_{fs}G_{ms}C_{fs}C_{ms}G_{fs}G_{ms}\underline{A}_{es}\underline{A}_{e}$ | 36 |
| 748472 | Pv-$\underline{T}_{es}G_{fs}G_{mo}G_{fs}C_{mo}C_{fs}C_{mo}G_{fs}\underline{A}_{mo}C_{fs}C_{mo}G_{fs}G_{mo}G_{fs}G_{ms}C_{fs}C_{ms}G_{fs}G_{ms}\underline{A}_{es}\underline{A}_{e}$ | 37 |

TABLE 15 ss-siRNAs with two mismatches to C9orf72 antisense transcript at positions 2-19

| Isis No. | Sequence (5' to 3') | SEQ ID NO. |
|---|---|---|
| 748479 | Pv-$\underline{T}_{es}G_{fs}G_{mo}G_{fs}G_{mo}C_{fs}C_{mo}G_{fs}\underline{A}_{mo}G_{fs}G_{mo}C_{fs}C_{mo}\underline{A}_{fs}G_{ms}G_{fs}G_{ms}C_{fs}C_{ms}\underline{A}_{es}\underline{A}_{e}$ | 38 |
| 748480 | Pv-$\underline{T}_{es}C_{fs}G_{mo}G_{fs}G_{mo}G_{fs}C_{mo}C_{fs}\underline{A}_{mo}G_{fs}G_{mo}G_{fs}C_{mo}\underline{A}_{fs}G_{ms}G_{fs}G_{ms}G_{fs}C_{ms}\underline{A}_{es}\underline{A}_{e}$ | 39 |
| 748481 | Pv-$\underline{T}_{es}C_{fs}C_{mo}G_{fs}G_{mo}G_{fs}G_{mo}C_{fs}\underline{A}_{mo}G_{fs}G_{mo}G_{fs}G_{mo}\underline{A}_{fs}C_{ms}G_{fs}G_{ms}G_{fs}G_{ms}\underline{A}_{es}\underline{A}_{e}$ | 40 |
| 748482 | Pv-$\underline{T}_{es}C_{fs}C_{mo}C_{fs}G_{mo}G_{fs}G_{mo}G_{fs}\underline{A}_{mo}C_{fs}G_{mo}G_{fs}G_{mo}\underline{A}_{fs}C_{ms}C_{fs}G_{ms}G_{fs}G_{ms}\underline{A}_{es}\underline{A}_{e}$ | 41 |
| 748483 | Pv-$\underline{T}_{es}G_{fs}G_{mo}C_{fs}C_{mo}C_{fs}G_{mo}G_{fs}\underline{A}_{mo}C_{fs}C_{mo}G_{fs}G_{mo}\underline{A}_{fs}G_{ms}C_{fs}C_{ms}G_{fs}G_{ms}\underline{A}_{es}\underline{A}_{e}$ | 42 |
| 748484 | Pv-$\underline{T}_{es}G_{fs}G_{mo}G_{fs}C_{mo}C_{fs}C_{mo}G_{fs}\underline{A}_{mo}C_{fs}C_{mo}G_{fs}G_{mo}\underline{A}_{fs}G_{ms}C_{fs}C_{ms}G_{fs}G_{ms}\underline{A}_{es}\underline{A}_{e}$ | 43 |

TABLE 16 ss-siRNAs with three mismatches to C9orf72 antisense transcript at positions 2-19

| Isis No. | Sequence (5' to 3') | SEQ ID NO. |
|---|---|---|
| 748473 | Pv-$\underline{T}_{es}G_{fs}G_{mo}G_{fs}G_{mo}C_{fs}C_{mo}G_{fs}\underline{A}_{mo}\underline{A}_{fs}\underline{A}_{mo}C_{fs}C_{mo}G_{fs}G_{ms}G_{fs}G_{ms}C_{fs}C_{ms}\underline{A}_{es}\underline{A}_{e}$ | 44 |
| 748474 | Pv-$\underline{T}_{es}C_{fs}G_{mo}G_{fs}G_{mo}G_{fs}C_{mo}C_{fs}\underline{A}_{mo}\underline{A}_{fs}\underline{A}_{mo}G_{fs}C_{mo}C_{fs}G_{ms}G_{fs}G_{ms}G_{fs}C_{ms}\underline{A}_{es}\underline{A}_{e}$ | 45 |
| 748475 | Pv-$\underline{T}_{es}C_{fs}C_{mo}G_{fs}G_{mo}G_{fs}G_{mo}C_{fs}\underline{A}_{mo}\underline{A}_{fs}\underline{A}_{mo}G_{fs}G_{mo}C_{fs}C_{ms}G_{fs}G_{ms}G_{fs}G_{ms}\underline{A}_{es}\underline{A}_{e}$ | 46 |
| 748476 | Pv-$\underline{T}_{es}C_{fs}C_{mo}C_{fs}G_{mo}G_{fs}G_{mo}G_{fs}\underline{A}_{mo}\underline{A}_{fs}\underline{A}_{mo}G_{fs}G_{mo}C_{fs}C_{fs}G_{ms}G_{fs}G_{ms}\underline{A}_{es}\underline{A}_{e}$ | 47 |

TABLE 16-continued ss-siRNAs with three mismatches to C9orf72 antisense transcript at positions 2-19

| Isis No. | Sequence (5' to 3') | SEQ ID NO. |
|---|---|---|
| 748477 | Pv-$\underline{T}_{es}G_{fs}G_{mo}C_{fs}C_{mo}G_{fs}G_{mo}G_{fs}\underline{A}_{mo}\underline{A}_{fs}\underline{A}_{no}G_{fs}G_{mo}G_{fs}G_{ms}C_{fs}C_{ms}G_{fs}G_{ms}\underline{A}_{es}\underline{A}_{e}$ | 48 |
| 748478 | Pv-$\underline{T}_{es}G_{fs}G_{mo}G_{fs}C_{mo}C_{fs}G_{mo}G_{fs}\underline{A}_{mo}\underline{A}_{fs}\underline{A}_{no}C_{fs}G_{mo}G_{fs}G_{ms}G_{fs}C_{ms}C_{fs}G_{ms}\underline{A}_{es}\underline{A}_{e}$ | 49 |

Subscripts: "s" indicates a phosphorothioate internucleoside linkage; "o" indicates an unmodified, phosphate internucleoside linkage; "f" indicates a 2'-fluoro modified nucleoside; "m" indicates a 2'-O-methyl modified nucleoside; and "e" indicates a 2'-O-methoxyethyl (MOE) modified nucleoside. "Pv" at the 5'-end indicates a 5'-(E)-vinylphosphonate group, (PO(OH)$_2$(CH=CH—).

Example 4: Inhibitory Effects of Modified ss-siRNAs Complementary to C9orf72 Sense Transcript on C9orf72 Sense Foci In Vitro Modified oligonucleotides described in Example 1 were tested for their effects on C9orf72 foci in ALS/FTD patient fibroblast cell lines.

qPCR Analysis

The fibroblast cells were plated at a density of 80,000 cells per well of a 6-well plague 48 hours before transfection with a cationic lipid for qPCR analysis. Cells were typically harvested 2 days after transfection. Modified oligonucleotides (listed in Table 18) or controls (described in Table 17) were added.

C9orf72 expression was analyzed by quantitative PCR on a 7500 real-time PCR system (Applied Biosystems) using iTaq SYBR Green Supermix (Bio-Rad). Data was normalized relative to levels of GAPDH mRNA. Primers specific for C9orf72 mRNA are as follows: all three variants (Forward 5'-AGAAGGCACAGAGAGAATGGAA-3' (SEQ ID NO: 55); Reverse 5'-TCATCATCATTGAGTACTGTATCAGC-3' (SEQ ID NO: 56); C9orf72 intron 1 (Forward 5'-ACGCCTGCACAATTTCAGCCCAA-3' (SEQ ID NO: 57); Reverse 5'-CAAGTCTGTGTCATCTCGGAGCTG-3' (SEQ ID NO: 58); and GAPDH Forward 5'-GTCATCAATGGAAATCCCATCAC-3' (SEQ ID NO: 59); Reverse 5'-TTCTCCATGGTGGTGAAGAC-3' (SEQ ID NO: 60).

RNA RISH and Imaging

RNA fluorescent in situ hybridization (FISH) was performed following a Biosearch protocol with minor modification. Fibroblast cells were plated at a density of 10,000/well into Lab-Tek 8-well chambered cover glass slides. After one day, siRNA/lipid complex were added at 50 nM final concentration. 48 hours after transfection, cells were fixed with 4% formaldehyde in 1×PBS and permeabilized in 70% ethanol at 4° C. overnight. Cells were washed with Wash Buffer (10% formamide in 2×SSC) for 5 minutes, and then incubated with pre-hybridization buffer (40% formamide in 2×SSC) at 60° C. for 20 minutes. A (CCCCGG)$_4$-Cy3 DNA probe or a (GGGGCC)$_{3.3}$-Cy3 probe in Hybridization Buffer (100 mg/mL dextran sulfate and 40% formamide in 2×SSC) was added. The slide was placed in a humidified chamber and incubated in the dark at 37° C. overnight. The next day, cells were washed twice with wash buffer at 37° C., then stained with mounting media and DAPI (Vector Labs, H-1500).

TABLE 17

Control oligonucleotides

| Identifier | Sequence (5'-3') | Target description | SEQ ID NO |
|---|---|---|---|
| cs1 | Pv-$T_{es}C_{fs}U_{mo}G_{fs}C_{mo}U_{fs}G_{mo}C_{fs}A_{mo}A_{fs}A_{mo}U_{fs}G_{mo}C_{s}U_{ms}G_{fs}C_{ms}U_{fs}G_{ms}A_{es}A_{e}$ | CAG | 50 |
| cs2 | Pv-$N_{es}N_{fs}N_{mo}N_{fs}N_{mo}N_{fs}N_{mo}N_{fs}N_{mo}N_{fs}N_{mo}N_{fs}N_{mo}N_{fs}N_{ms}N_{fs}N_{ms}N_{fs}N_{ms}N_{es}N_{e}$ | Unrelated target | 51 |
| cs3 | Pv-$T_{es}A_{fs}A_{mo}C_{fs}U_{mo}U_{fs}C_{mo}A_{fs}G_{mo}G_{fs}G_{mo}U_{fs}C_{mo}A_{s}G_{ms}C_{fs}U_{ms}U_{fs}G_{ms}A_{es}A_{e}$ | EGFP | 52 |

Duplex RNA (antisense strand, 5'-3')

| R3 | CGGCCCCGAAACCGGCCCCdTdT | Repeat | 53 |
| C1 | GCUAUACCAGCGUCGUCAUdTdT | Control-Repeat | 54 |

Subscripts:
"s" indicates a phosphorothioate internucleoside linkage;
"o" indicates an unmodified, phosphate internucleoside linkage;
"f" indicates a 2'-fluoro modified nucleoside;
"m" indicates a 2'-O-methyl modified nucleoside; and "e" indicates a 2'-O-methoxyethyl (MOE) modified nucleoside.
"Pv" at the 5'-end indicates a 5'-(E)-vinylphosphonate group, (PO(OH)$_2$(CH=CH—).
"N" indicates an undisclosed base.
Control "cs2" is not complementary to human C9orf72 and targets an unrelated gene.
All of the mismatches, whether they are inside or outside of the complementary region, are underlined.
"d" in the duplex RNA controls indicates a 2'-deoxynucleoside.

Cells were imaged at 60× magnification using a Widefield Deltavision microscope. Images were processed by blind deconvolution with AutoQuant X3. Visualization of RNA foci were made using ImageJ. For quantification, at least 20 pictures were taken from randomly chosen microscopic fields, containing 100-300 cells for each treatment. Counting foci was performed by different investigators. All data were generated by at least three independent experiments.

The results, provided in Table 18 and FIGS. 2A-B, indicate that the modified oligonucleotides targeting the C9orf72 sense transcript decreased the percent total cells with C9orf72 sense foci and the number of C9orf72 sense foci per 100 cells as compared to controls.

TABLE 18 ss-siRNAs complementary to C9orf72 sense transcript reduce sense foci in ALS/FTD patient fibroblast cells

| Identifier | # of Mismatches or control description | % Total cells with foci | # Foci per 100 cells |
|---|---|---|---|
| 742036 | 0 | 1.1 | 1.1 |
| 742037 | 0 | 1.8 | 1.5 |
| 742038 | 0 | 6.5 | 7.1 |
| 742039 | 0 | 0.8 | 1.9 |
| 742040 | 0 | 2.0 | 2.0 |
| 742041 | 0 | 0.8 | 2.5 |
| 742042 | 1 | 12 | 16 |
| 742048 | 3 | 7.5 | 9.6 |
| 742049 | 3 | 15 | 30 |
| 742050 | 3 | 13 | 14 |
| 742051 | 3 | 12 | 12 |
| 742054 | 2 | 13 | 19 |
| cs1 | Control - CAG repeat | 41 | 112 |
| cs2 | Control - Unrelated target | 34 | 75 |
| cs3 | Control - EGFP | 42 | 94 |
| R3 | Control - Repeat | 13 | 28 |
| C1 | Control - No target | 46 | 120 |

Example 5: Inhibitory Effects of Modified ss-siRNAs Complementary to C9orf72 Antisense Transcript on C9orf72 Antisense Foci In Vitro Modified oligonucleotides described in Example 1 were tested for their effects on C9orf72 antisense foci in ALS/FTD patient fibroblast cell lines. qPCR, RNA FISH, and imaging were conducted as described in Example 4. Controls are described in Example 4. The results, provided in Table 19 and FIGS. 3A-B, indicate that the modified oligonucleotides targeting the C9orf72 antisense transcript decreased the percent total cells with C9orf72 antisense foci and the number of C9orf72 antisense foci per 100 cells as compared to controls.

TABLE 19 ss-siRNAs complementary to C9orf72 antisense transcript reduce antisense foci in ALS/FTD patient fibroblast cells

| Identifier | # of Mismatches or control description | % Total cells with foci | # Foci per 100 cells |
|---|---|---|---|
| 742060 | 0 | 16 | 33 |
| 742061 | 0 | 19 | 26 |
| 742066 | 1 | 11 | 16 |
| 742072 | 3 | 17 | 34 |
| 742073 | 3 | 33 | 65 |
| 742074 | 3 | 34 | 88 |
| 742075 | 3 | 28 | 65 |
| 742078 | 2 | 15 | 25 |
| cs2 | Control - Unrelated target | 53 | 207 |
| cs3 | Control - EGFP | 51 | 181 |

Example 6: Defects of Modified ss-siRNA Lacking a 5'-Phosphate on C9orf72 Foci In Vitro Isis 918924 and 918925, each lacking a 5'-phosphate, and complementary to the hexanucleotide repeat region of human C9orf72 sense transcript were tested in ALS/FTD patient fibroblast cell lines. qPCR, RNA FISH, and imaging were conducted as described in Example 4. Control "cs3" is described in Example 4. Isis 918924 and 918925 are analogs of 742036 and 742048 (respectively). Isis 918924 and 918925 are described in Table 20.

Isis 918924 and 918925 were tested in ALS/FTD patient fibroblast cell lines to determine whether multiple RNAi mechanisms contribute to blocking C9orf72 foci. A 5'-phosphate is required for an ss-siRNA containing a 5'-terminal methoxyethyl base to function through an RNA mechanism. Therefore, if Isis 918924 and 918925 are effective in reducing foci, then they are working through a non-RNAi mechanism. The results, provided in Table 20 and FIG. 4A indicate that Isis 918924 was as potent as analogous Isis 742036, demonstrating that GGGGCC ss-siRNAs can act through a non-RNAi mechanism. Table 20 and FIG. 4B indicate that Isis 918925 was less active than analogous Isis 742048. Isis 918925 may be less active because when mismatches are present, they destablisze interactions with the target. This destabilization may prevent efficient recognition in the absences of assistance by RNAi factors. The ability of a mismatched single strand to use RNAi factors like argonaute may be indispensable for maximal activity.

TABLE 20

Effect of ss-siRNAs lacking a 5'-phosphate on C9orf72 sense foci

| Identfier | Sequence (5'-3') | # of Mismatches or control description | % Total cells with foci | # Foci per 100 cells | SEQ ID NO |
|---|---|---|---|---|---|
| 742036 | Pv-$T_{es}G_{fs}G_{mo}C_{fs}C_{mo}C_{fs}C_{mo}G_{fs}G_{mo}C_{fs}C_{mo}C_{fs}C_{mo}G_{fs}G_{ms}$ $C_{fs}C_{ms}C_{fs}C_{ms}A_{es}A_{e}$ | 0 | 4.8 | 6.5 | 2 |
| 742048 | Pv-$T_{es}G_{fs}G_{mo}C_{fs}C_{mo}C_{fs}C_{mo}G_{fs}G_{mo}\underline{A}_{fs}\underline{A}_{mo}\underline{A}_{no}C_{fs}C_{mo}G_{fs}G_{ms}$ $C_{fs}C_{ms}C_{fs}C_{ms}A_{es}A_{e}$ | 3 | 6.1 | 9.1 | 20 |
| 918924 | $T_{es}G_{fs}G_{mo}C_{fs}C_{mo}C_{fs}C_{mo}G_{fs}G_{mo}C_{fs}C_{mo}C_{fs}C_{mo}G_{fs}G_{ms}$ $C_{fs}C_{ms}C_{fs}C_{ms}A_{es}A_{e}$ | 0 | 4.1 | 5.8 | 2 |

TABLE 20-continued

Effect of ss-siRNAs lacking a 5'-phosphate on C9orf72 sense foci

| Identfier | Sequence (5'-3') | # of Mismatches or control description | % Total cells with foci | # Foci per 100 cells | SEQ ID NO |
|---|---|---|---|---|---|
| 918925 | $T_{es}G_{fs}G_{mo}C_{fs}C_{mo}C_{fs}C_{mo}G_{fs}A_{mo}A_{fs}A_{mo}C_{fs}C_{mo}G_{fs}G_{ms}$ $C_{fs}C_{ms}C_{fs}C_{ms}A_{es}A_e$ | 3 | 30 | 58 | 20 |
| cs3 | $Pv\text{-}T_{es}A_{fs}A_{mo}C_{fs}U_{mo}U_{fs}C_{mo}A_{fs}G_{mo}G_{fs}G_{mo}U_{fs}C_{mo}A_sG_{ms}$ $C_{fs}U_{ms}U_{fs}G_{ms}A_{es}A_e$ | Control-EGFP | 42 | 106 | 52 |

Subscripts:
"s" indicates a phosphorothioate internucleoside linkage;
"o" indicates an unmodified, phosphate internucleoside linkage;
"f" indicates a 2'-fluoro modified nucleoside; "m" indicates a 2'-O-methyl modified nucleoside; and
"e" indicates a 2'-O-methoxyethyl (MOE) modified nucleoside.
"Pv" at the 5'-end indicates a 5'-(E)-vinylphosphonate group, $(PO(OH)_2(CH=CH-)$.
All of the mismatches, whether they are inside or outside of the complementary region, are underlined.

What is claimed is:

1. A compound comprising a modified oligonucleotide and a terminal group at the 5'-end of the modified oligonucleotide, wherein the modified oligonucleotide consists of 21 to 30 linked nucleosides and comprises a nucleobase sequence selected from among: SEQ ID NO: 2, 3, 4, 5, 6, 7, 8, 9, 10, 11, 12, 13, 14, 15, 16, 17, 18, 19, 20, 21, 22, 23, 24, and 25;

and wherein the terminal group comprises a phosphorus moiety.

2. The compound of claim 1, wherein the 5'-terminal nucleoside and terminal group of the compound has Formula I:

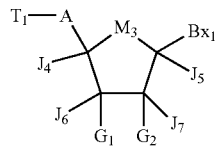

wherein:

$T_1$ is a phosphorus moiety;

A has a formula selected from among:

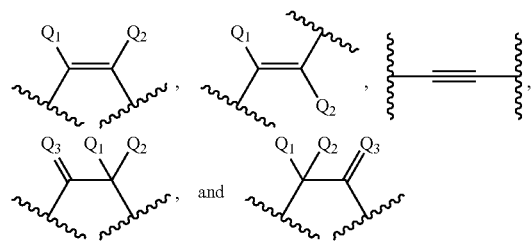

$Q_1$ and $Q_2$ are each independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl, and $N(R_3)$ $(R_4)$;

$Q_3$ is selected from among: O, S, $N(R_5)$, and $C(R_6)(R_7)$;

each $R_3$, $R_4$ $R_5$, $R_6$ and $R_7$ is independently selected from among: H, $C_1$-$C_6$ alkyl, substituted $C_1$-$C_6$ alkyl, and $C_1$-$C_6$ alkoxy;

$M_3$ is selected from among: O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$, and $OC(R_{15})(Bx_2)$;

$R_{14}$ is selected from among: H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

$R_{15}$, $R_{16}$, $R_{17}$ and $R_{18}$ are each independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

if $Bx_2$ is present, then $Bx_2$ is a nucleobase and $Bx_1$ is selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

if $Bx_2$ is not present, then $Bx_1$ is a nucleobase;

either each of $J_4$, $J_5$, $J_6$ and $J_7$ is independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

or $J_4$ forms a bridge with one of $J_5$ or $J_7$ wherein the bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;

each $R_{19}$, $R_{20}$ and $R_{21}$ is independently selected from among: H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl;

one of $G_1$ and $G_2$ is selected from among: H, OH, halogen, and O—[C($R_8$)($R_9$)]$_n$—[(C=O)$_m$—$X_1$]$_j$—Z; and the other of $G_1$ and $G_2$ is: O-$T_2$;

$T_2$ is an internucleoside linking group linking the 5'-terminal nucleoside of Formula I to the remainder of the oligonucleotide;

each $R_8$ and $R_9$ is independently selected from among: H, halogen, $C_1$-$C_6$ alkyl, and substituted $C_1$-$C_6$ alkyl;

$X_1$ is O, S or N($E_1$);

Z is selected from among: H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, and N($F_2$)($F_3$);

$E_1$, $E_2$ and $E_3$ are each independently selected from among: H, $C_1$-$C_6$ alkyl, and substituted $C_1$-$C_6$ alkyl;

n is from 1 to 6;

m is 0 or 1;

j is 0 or 1;

provided that, if j is 1, then Z is other than halogen or N($E_2$)($E_3$);

each substituted group comprises one or more optionally protected substituent groups independently selected from among: a halogen, $OJ_1$, N($J_1$)($J_2$), =$NJ_1$, $SJ_1$, $N_3$, CN, OC(=$X_2$)$J_1$, OC(=$X_2$)N($J_1$)($J_2$), and C(=$X_2$)N($J_1$)($J_2$);

$X_2$ is O, S or $NJ_3$; and each $J_1$, $J_2$ and $J_3$ is independently selected from among: H and $C_1$-$C_6$ alkyl.

3. The compound of claim 2, wherein $M_3$ is selected from among: O, CH=CH, $OCH_2$, and OC(H)(Bx$_2$).

4. The compound of claim 2, wherein each of $J_4$, $J_5$, $J_6$ and $J_7$ is H.

5. The compound of claim 2, wherein $J_4$ forms a bridge with either $J_5$ or $J_7$.

6. The compound of claim 2, wherein A has the formula:

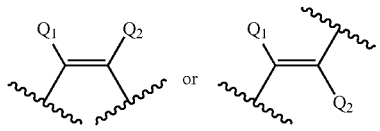

wherein:

$Q_1$ and $Q_2$ are each independently selected from among: H, halogen, $C_1$-$C_6$ alkyl, substituted $C_1$-$C_6$ alkyl, $C_1$-$C_6$ alkoxy, and substituted $C_1$-$C_6$ alkoxy.

7. The compound of claim 6, wherein each of $Q_1$ and $Q_2$ is H.

8. The compound of claim 6, wherein $Q_1$ and $Q_2$ are each independently selected from among: H and a halogen.

9. The compound of claim 6, wherein one of $Q_1$ and $Q_2$ is H and the other of $Q_1$ and $Q_2$ is F, $CH_3$, or $OCH_3$.

10. The compound of claim 2, wherein $T_1$ has the formula:

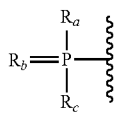

wherein:

$R_a$ and $R_c$ are each independently selected from among: hydroxyl, protected hydroxyl, thiol, protected thiol, $C_1$-$C_6$ alkyl, substituted $C_1$-$C_6$ alkyl, $C_1$-$C_6$ alkoxy, substituted $C_1$-$C_6$ alkoxy, amino, protected amino, or substituted amino; and $R_b$ is O or S.

11. The compound of claim 10, wherein $R_b$ is O and $R_a$ and $R_c$ are each, independently selected from among: OH, $OCH_3$, $OCH_2CH_3$, and $OCH(CH_3)_2$.

12. The compound of claim 2, wherein one of $G_1$ and $G_2$ is selected from among: a halogen, $OCH_3$, $OCH_2F$, $OCHF_2$, $OCF_3$, $OCH_2CH_3$, O(CH$_2$)$_2$F, $OCH_2CHF_2$, $OCH_2CF_3$, $OCH_2$—CH=CH$_2$, O(CH$_2$)$_2$—OCH$_3$, O(CH$_2$)$_2$—SCH$_3$, O(CH$_2$)$_2$—OCF$_3$, O(CH$_2$)$_3$—N($R_{10}$)($R_{11}$), O(CH$_2$)$_2$—ON($R_{10}$)($R_{11}$), O(CH$_2$)$_2$—O(CH$_2$)$_2$—N($R_{10}$)($R_{11}$), OCH$_2$C(=O)—N($R_{10}$)($R_{11}$), OCH$_2$C(=O)—N($R_{12}$)—(CH$_2$)$_2$—N($R_{10}$)($R_{11}$), and O(CH$_2$)$_2$—N($R_{12}$)—C(=N$R_{13}$)[N($R_{10}$)($R_{11}$)]; wherein $R_{10}$, $R_{11}$, $R_{12}$ and $R_{13}$ are each, independently, H or $C_1$-$C_6$ alkyl.

13. The compound of claim 2, wherein one of $G_1$ and $G_2$ is selected from among: a halogen, $OCH_3$, $OCF_3$, $OCH_2CH_3$, $OCH_2CF_3$, $OCH_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

14. The compound of claim 2, wherein one of $G_1$ and $G_2$ is selected from among: F, $OCH_3$, and O(CH$_2$)$_2$—OCH$_3$.

15. The compound of claim 14, wherein one of $G_1$ and $G_2$ is O(CH$_2$)$_2$—OCH$_3$.

16. The compound of claim 2, wherein the 5'-terminal nucleoside and terminal group of the compound has Formula III:

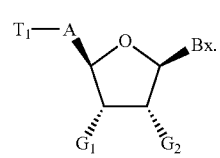

17. The compound of claim 16, wherein A has the formula:

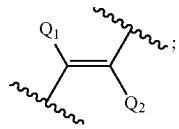

wherein $Q_1$ and $Q_2$ are each independently selected from among: H, a halogen, $C_1$-$C_6$ alkyl, substituted $C_1$-$C_6$ alkyl, $C_1$-$C_6$ alkoxy, and substituted $C_1$-$C_6$ alkoxy.

18. The compound of claim 17, wherein $Q_1$ and $Q_2$ are each independently selected from among: H, F, $CH_3$, and $OCH_3$.

19. The compound of claim 2, wherein the 5'-terminal nucleoside and the terminal group has Formula V:

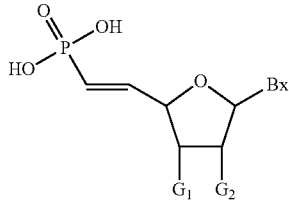

wherein:
Bx is selected from among: uracil, thymine, cytosine, 5-methyl cytosine, adenine, and guanine;
one of $G_1$ and $G_2$ is selected from among: a halogen, $OCH_3$, $OCF_3$, $OCH_2CH_3$, $OCH_2CF_3$, $OCH_2$—$CH=CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$, and $OCH_2$—$N(H)$—$C(=NH)NH_2$;
and the other of $G_1$ and $G_2$ is O—$T_2$, wherein $T_2$ is a phosphorothioate internucleoside linking group linking the compound of Formula V to the remainder of the oligonucleotide.

20. The compound of claim 1, wherein the modified oligonucleotide comprises at least two modified sugar moieties.

21. The compound of claim 20, wherein the modified oligonucleotide is fully modified.

22. The compound of claim 20, wherein each modified sugar moiety is independently selected from among: 2'-F, 2'-MOE, 2'-OMe, LNA, F-HNA, and cEt.

23. The compound of claim 1, wherein the modified oligonucleotide comprises at least one region having sugar motif:
-[(A)$_x$-(B)$_y$-(A)$_z$]$_q$
wherein
A is a modified nucleoside of a first type,
B is a modified nucleoside of a second type;
each x and each y is independently 1 or 2;
z is 0 or 1; and
q is 3-15.

24. The compound of claim 1, wherein the modified oligonucleotide comprises 1-4 3'-terminal nucleosides, each comprising the same modified sugar moiety, wherein the modified sugar moiety of the 1-4 3'-terminal nucleosides is different from the modified sugar moiety of the immediately adjacent nucleoside.

25. The compound of claim 24, wherein the 3'-terminal nucleosides are each 2'-MOE nucleosides.

26. The compound of claim 24, comprising two 3'-terminal nucleosides.

27. The compound of claim 1, wherein the modified oligonucleotide comprises at least one modified internucleoside linkage.

28. The compound of claim 27, wherein each internucleoside linkage of the modified oligonucleotide is selected from a phosphorothioate internucleoside linkage and an unmodified, phosphate internucleoside linkage.

29. The compound of claim 1, wherein the compound comprises a second modified oligonucleotide comprising a nucleobase sequence selected from among: SEQ ID NO: 26, 27, 28, 29, 30, 31, 32, 33, 34, 35, 36, 37, 38, 39, 40, 41, 42, 43, 44, 45, 46, 47, 48, and 49, such that the modified oligonucleotide and the second modified oligonucleotide form a duplex oligonucleotide.

30. The compound of claim 1, wherein the phosphorus moiety is an unmodified phosphate.

31. The compound of claim 1, wherein the phosphorus moiety is a 5'-(E)-vinylphosphonate group having the formula:

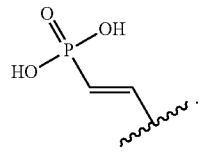

32. The compound of claim 1, wherein the compound is an oligomeric compound.

33. The compound of claim 32, wherein the oligomeric compound is paired with a second oligomeric compound to form a duplex.

34. The compound of claim 1, wherein the compound is single-stranded.

35. A method of reducing C9orf72 foci comprising contacting a cell with the compound of claim 1.

* * * * *

SEQUENCE LISTING

<160> NUMBER OF SEQ ID NOS: 60

<210> SEQ ID NO 1
<211> LENGTH: 30001
<212> TYPE: DNA
<213> ORGANISM: Homo sapiens

<400> SEQUENCE: 1

```
caaagaaaag ggggaggttt tgttaaaaaa gagaaatgtt acatagtgct ctttgagaaa      60
attcattggc actattaagg atctgaggag ctggtgagtt tcaactggtg agtgatggtg     120
gtagataaaa ttagagctgc agcaggtcat tttagcaact attagataaa actggtctca     180
ggtcacaacg ggcagttgca gcagctggac ttggagagaa ttacactgtg ggagcagtgt     240
catttgtcct aagtgctttt ctacccccta ccccactat tttagttggg tataaaaaga      300
atgacccaat ttgtatgatc aactttcaca aagcatagaa cagtaggaaa agggtctgtt     360
tctgcagaag gtgtagacgt tgagagccat tttgtgtatt tattcctccc tttcttcctc     420
ggtgaatgat taaaacgttc tgtgtgattt ttagtgatga aaaagattaa atgctactca     480
ctgtagtaag tgccatctca cacttgcaga tcaaaaggca cacagtttaa aaaacctttg     540
ttttttttaca catctgagtg gtgtaaatgc tactcatctg tagtaagtgg aatctataca     600
cctgcagacc aaaagacgca aggtttcaaa aatctttgtg ttttttacac atcaaacaga     660
atggtacgtt tttcaaaagt taaaaaaaaa caactcatcc acatattgca actagcaaaa     720
atgacattcc ccagtgtgaa aatcatgctt gagagaattc ttacatgtaa aggcaaaatt     780
gcgatgactt tgcaggggac cgtgggattc ccgcccgcag tgccggagct gtcccctacc     840
agggtttgca gtggagtttt gaatgcactt aacagtgtct tacggtaaaa acaaaatttc     900
atccaccaat tatgtgttga gcgcccactg cctaccaagc acaaacaaaa ccattcaaaa     960
ccacgaaatc gtcttcactt tctccagatc cagcagcctc ccctattaag gttcgcacac    1020
gctattgcgc caacgctcct ccagagcggg tcttaagata aagaacagg acaagttgcc     1080
ccgccccatt tcgctagcct cgtgagaaaa cgtcatcgca catagaaaac agacagacgt    1140
aacctacggt gtcccgctag gaaagagagg tgcgtcaaac agcgacaagt tccgcccacg    1200
taaaagatga cgcttggtgt gtcagccgtc cctgctgccc ggttgcttct cttttggggg    1260
cggggtctag caagagcagg tgtgggttta ggaggtgtgt gttttttgttt ttcccaccct    1320
```

```
ctctccccac tacttgctct cacagtactc gctgagggtg aacaagaaaa gacctgataa    1380
agattaacca gaagaaaaca aggagggaaa caaccgcagc ctgtagcaag ctctggaact    1440
caggagtcgc gcgctagggg ccggggccgg ggccggggcg tggtcggggc gggcccgggg    1500
gcgggcccgg ggcggggctg cggttgcggt gcctgcgccc gcggcggcgg aggcgcaggc    1560
ggtggcgagt gggtgagtga ggaggcggca tcctggcggg tggctgtttg gggttcggct    1620
gccgggaaga ggcgcgggta gaagcggggg ctctcctcag agctcgacgc attttttactt    1680 tccctctcat ttctctgacc gaagctgggt gtcgggcttt cgcctctagc gactggtgga    1740
attgcctgca tccgggcccc gggcttcccg cggcggcgg cggcggcggc ggcgcaggga    1800
caagggatgg ggatctggcc tcttccttgc tttcccgccc tcagtacccg agctgtctcc    1860
ttcccgggga cccgctggga gcgctgccgc tgcgggctcg agaaaaggga gcctcgggta    1920
ctgagaggcc tcgcctgggg gaaggccgga gggtgggcgg cgcgcggctt ctgcggacca    1980
agtcggggtt cgctaggaac ccgagacggt ccctgccggc gaggagatca tgcgggatga    2040
gatgggggtg tggagacgcc tgcacaattt cagcccaagc ttctagagag tggtgatgac    2100
ttgcatatga gggcagcaat gcaagtcggt gtgctcccca ttctgtggga catgacctgg    2160
ttgcttcaca gctccgagat gacacagact tgcttaaagg aagtgactat tgtgacttgg    2220
gcatcacttg actgatggta atcagttgtc taaagaagtg cacagattac atgtccgtgt    2280
gctcattggg tctatctggc gcgttgaac accaccaggc tttgtattca gaaacaggag    2340
ggaggtcctg cactttccca ggaggggtgg ccctttcaga tgcaatcgag attgttaggc    2400
tctgggagag tagttgcctg gttgtggcag ttggtaaatt tctattcaaa cagttgccat    2460
gcaccagttg ttcacaacaa gggtacgtaa tctgtctggc attacttcta cttttgtaca    2520
aaggatcaaa aaaaaaaag atactgttaa gatatgattt ttctcagact ttgggaaact    2580
tttaacataa tctgtgaata tcacagaaac aagactatca tatagggat attaataacc    2640 tggagtcaga atacttgaaa tacgtgtca tttgacacgg gcattgttgt caccacctct    2700
gccaaggcct gccactttag gaaaaccctg aatcagttgg aaactgctac atgctgatag    2760
tacatctgaa acaagaacga gagtaattac cacattccag attgttcact aagccagcat    2820
ttacctgctc caggaaaaaa ttacaagcac cttatgaagt tgataaaata ttttgtttgg    2880
ctatgttggc actccacaat ttgctttcag agaaacaaag taaaccaagg aggacttctg    2940
tttttcaagt ctgccctcgg gttctattct acgttaatta gatagttccc aggaggacta    3000
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctctttgggc tgggagaaaa taaacagcat ggttacaagt    3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttgggaggct gaggcaggag ggtcatttga gcccaagagt ttgaagttac cgagagctat    3480
gatcctgcca gtgcattcca gcctggatga caaaacgaga ccctgtctct aaaaaacaag    3540
aagtgagggc tttatgattg tagaattttc actacaatag cagtggacca accacctttc    3600
taaataccaa tcagggaaga gatggttgat tttttaacag acgtttaaag aaaaagcaaa    3660 acctcaaaact tagcactcta ctaacagttt tagcagatgt taattaatgt aatcatgtct    3720
```

```
gcatgtatgg gattatttcc agaaagtgta ttgggaaacc tctcatgaac cctgtgagca    3780
agccaccgtc tcactcaatt tgaatcttgg cttccctcaa aagactggct aatgtttggt    3840
aactctctgg agtagacagc actacatgta cgtaagatag gtacataaac aactattggt    3900
tttgagctga ttttttttcag ctgcatttgc atgtatggat ttttctcacc aaagacgatg    3960
acttcaagta ttagtaaaat aattgtacag ctctcctgat tatacttctc tgtgacattt    4020
catttcccag gctatttctt ttggtaggat ttaaaactaa gcaattcagt atgatctttg    4080
tccttcattt tctttcttat tcttttttgtt tgtttgtttg tttgttttttt tcttgaggca    4140 gagtctctct ctgtcgccca ggctggagtg cagtggcgcc atctcagctc attgcaacct    4200
ctgccacctc cgggttcaag agattctcct gcctcagcct cccgagtagc tgggattaca    4260
ggtgtccacc accacacccg ctaattttt tgtattttta gtagaggtgg ggtttcacca    4320
tgttggccag gctggtcttg agctcctgac ctcaggtgat ccacctgcct cggcctacca    4380
aagagctggg ataacaggtg tgacccacca tgcccggccc attttttttt tcttattctg    4440
ttaggagtga gagtgtaact agcagtataa tagttcaatt ttcacaacgt ggtaaaagtt    4500
tccctataat tcaatcagat tttgctccag ggttcagttc tgttttagga aatacttttta    4560 ttttcagttt aatgatgaaa tattagagtt gtaatattgc ctttatgatt atccacctttt    4620 ttaacctaaa agaatgaaag aaaaatatgt ttgcaatata attttatggt tgtatgttaa    4680
cttaattcat tatgttggcc tccagtttgc tgttgttagt tatgacagca gtagtgtcat    4740
taccatttca attcagatta cattcctata tttgatcatt gtaaactgac tgcttacatt    4800
gtattaaaaa cagtggatat tttaaagaag ctgtacggct tatatctagt gctgtctctt    4860
aagactatta aattgataca acatatttaa aagtaaatat tacctaaatg aattttttgaa    4920 attacaaata cacgtgttaa aactgtcgtt gtgttcaacc atttctgtac atacttagag    4980
ttaactgttt tgccaggctc tgtatgccta ctcataatat gataaaagca ctcatctaat    5040
gctctgtaaa tagaagtcag tgcttttccat cagactgaac tctcttgaca agatgtggat    5100
gaaattcttt aagtaaaatt gtttactttg tcatacattt acagatcaaa tgttagctcc    5160
caaagcaatc atatggcaaa gataggtata tcatagtttg cctattagct gctttgtatt    5220
gctattatta taaatagact tcacagtttt agacttgctt aggtgaaatt gcaattcttt    5280
ttactttcag tcttagataa caagtcttca attatagtac aatcacacat tgcttaggaa    5340
tgcatcatta ggcgattttg tcattatgca aacatcatag agtgtactta cacaaaccta    5400
gatagtatag cctttatgta cctaggccgt atggtatagt ctgttgctcc taggccacaa    5460
acctgtacaa ctgttactgt actgaatact atagacagtt gtaacacagt ggtaaatatt    5520
tatctaaata tatgcaaaca gagaaaaggt acagtaaaag tatggtataa aagataatgg    5580
tatacctgtg taggccactt accacgaatg gagcttgcag gactagaagt tgctctgggt    5640
gagtcagtga gtgagtggtg aattaatgtg aaggcctaga acactgtaca ccactgtaga    5700
ctataaacac agtacgctga agctacacca aatttatctt aacagttttt cttcaataaa    5760
aaattataac ttttaacctt tgtaaacttt ttaattttttt aacttttaaa atacttagct    5820
tgaaacacaa atacattgta tagctataca aaaatatttt ttctttgtat ccttattcta    5880
gaagcttttt tctatttttct attttaaatt tttttttta cttgttagtc gttttttgtta    5940 aaaactaaaa cacacacact ttcacctagg catagacagg attaggatca tcagtatcac    6000
tcccttccac ctcactgcct tccacctcca catcttgtcc cactggaagg tttttagggg    6060
```

-continued

```
caataacaca catgtagctg tcacctatga taacagtgct ttctgttgaa tacctcctga      6120
aggacttgcc tgaggctgtt ttacatttaa cttaaaaaaa aaaaagtag aaggagtgca       6180 ctctaaaata acaataaaag gcatagtata gtgaatacat aaaccagcaa tgtagtagtt     6240
tattatcaag tgttgtacac tgtaataatt gtatgtgcta tactttaaat aacttgcaaa     6300
atagtactaa gaccttatga tggttacagt gtcactaagg caatagcata ttttcaggtc     6360
cattgtaatc taatgggact accatcatat atgcagtcta ccattgactg aaacgttaca     6420
tggcacataa ctgtatttgc aagaatgatt tgttttacat taatatcaca taggatgtac     6480 cttttttagag tggtatgttt atgtggatta agatgtacaa gttgagcaag gggaccaaga    6540
gccctgggtt ctgtcttgga tgtgagcgtt tatgttcttc tcctcatgtc tgttttctca     6600
ttaaattcaa aggcttgaac gggcccatat tagcccttct gttttctacg tgttctaaat    6660
aactaaagct tttaaattct agccatttag tgtagaactc tctttgcagt gatgaaatgc    6720
tgtattggtt tcttggctag catattaaat attttatct ttgtcttgat acttcaatgt     6780
cgttttaaac atcaggatcg ggcttcagta ttctcataac cagagagttc actgaggata    6840
caggactgtt tgcccatttt ttgttatggc tccagacttg tggtatttcc atgtcttttt    6900 ttttttttt tttttgacc ttttagcggc tttaaagtat ttctgttgtt aggtgttgta      6960
ttacttttct aagattactt aacaaagcac cacaaactga gtggctttaa acaacagcaa    7020
tttattctct cacaattcta gaagctagaa gtccgaaatc aaagtgttga caggggcatg    7080
atcttcaaga gagaagactc tttccttgcc tcttcctggc ttctggtggt taccagcaat    7140
cctgagtgtt cctttcttgc cttgtagttt caacaatcca gtatctgcct tttgtcttca    7200
catggctgtc taccatttgt ctctgtgtct ccaaatctct ctccttataa acacagcagt    7260
tattggatta ggccccactc taatccagta tgacccatt ttaacatgat tacacttatt     7320
tctagataag gtcacattca cgtacaccaa gggttaggaa ttgaacatat cttttttgggg   7380 gacacaattc aacccacaag tgtcagtctc tagctgagcc tttcccttcc tgttttctc     7440 cttttagtt gctatgggtt aggggccaaa tctccagtca tactagaatt gcacatggac    7500
tggatatttg ggaatactgc gggtctattc tatgagcttt agtatgtaac atttaatatc    7560
agtgtaaaga agcccttttt taagttatt ctttgaattt ctaaatgtat gccctgaata    7620
taagtaacaa gttaccatgt cttgtaaaat gatcatatca acaaacattt aatgtgcacc    7680
tactgtgcta gttgaatgtc tttatcctga taggagataa caggattcca catctttgac    7740
ttaagaggac aaaccaaata tgtctaaatc atttgggggtt ttgatggata tctttaaatt   7800
gctgaaccta atcattggtt tcatatgtca ttgtttagat atctccggag catttggata   7860
atgtgacagt tggaatgcag tgatgtcgac tcttttgccca ccgccatctc cagctgttgc   7920
caagacagag attgctttaa gtggcaaatc accttttatta gcagctactt ttgcttactg   7980
ggacaatatt cttggtccta gagtaaggca catttgggct ccaaagacag aacaggtact    8040
tctcagtgat ggagaaataa cttttcttgc caaccacact ctaaatggag aaatccttcg    8100
aaatgcagag agtggtgcta tagatgtaaa gttttttgtc ttgtctgaaa agggagtgat    8160
tattgtttca ttaatctttg atggaaactg gaatggggat cgcagcacat atggactatc   8220
aattatactt ccacagacag aacttagttt ctacctccca cttcatagag tgtgtgttga   8280
tagattaaca catataatcc ggaaaggaag aatatggatg cataaggtaa gtgattttc    8340 agcttattaa tcatgttaac ctatctgttg aaagcttatt ttctggtaca tataaatctt   8400 attttttaa ttatatgcag tgaacatcaa acaataaatg ttatttattt tgcatttacc    8460
```

```
ctattagata caaatacatc tggtctgata cctgtcatct tcatattaac tgtggaaggt    8520
acgaaatggt agctccacat tatagatgaa aagctaaagc ttagacaaat aaagaaactt    8580
ttagaccctg gattcttctt gggagccttt gactctaata cctttgtttt cctttcatt     8640 gcacaattct gtcttttgct tactactatg tgtaagtata acagttcaaa gtaatagttt    8700
cataagctgt tggtcatgta gcctttggtc tctttaacct ctttgccaag ttcccaggtt    8760
cataaaatga ggaggttgaa tggaatggtt cccaagagaa ttcctttaa tcttacagaa     8820 attattgttt tcctaaatcc tgtagttgaa tatataatgc tatttacatt tcagtatagt    8880
tttgatgtat ctaaagaaca cattgaattc tccttcctgt gttccagttt gatactaacc    8940
tgaaagtcca ttaagcatta ccagttttaa aaggcttttg cccaatagta aggaaaaata    9000
atatctttta aaagaataat tttttactat gtttgcaggc ttacttcctt ttttctcaca    9060
ttatgaaact cttaaaatca ggagaatctt ttaaacaaca tcataatgtt taatttgaaa    9120
agtgcaagtc attcttttcc ttttttgaaac tatgcagatg ttacattgac tgttttctgt   9180
gaagttatct ttttttcact gcagaataaa ggttgttttg attttatttt gtattgttta    9240
tgagaacatg catttgttgg gttaatttcc taccccgcc cccattttt ccctaaagta      9300 gaaagtattt ttcttgtgaa ctaaattact acacaagaac atgtctattg aaaaataagc    9360
aagtatcaaa atgttgtggg ttgttttttt aaataaattt tctcttgctc aggaaagaca    9420
agaaaatgtc cagaagatta tcttagaagg cacagagaga atggaagatc aggtatatgc    9480
aaattgcata ctgtcaaatg ttttttctcac agcatgtatc tgtataaggt tgatggctac   9540
atttgtcaag gccttggaga catacgaata agcctttaat ggagctttta tggaggtgta    9600
cagaataaac tggaggaaga tttccatatc ttaaacccaa agagttaaat cagtaaacaa    9660
aggaaaatag taattgcatc tacaaattaa tatttgctcc ctttttttt ctgtttgccc     9720 agaataaatt ttggataact tgttcatagt aaaaataaaa aaaattgtct ctgatatgtt    9780 cttttaaggta ctacttctcg aaccttccc tagaagtagc tgtaacagaa ggagagcata    9840 tgtaccctg aggtatctgt ctggggtgta ggcccaggtc cacacaatat ttcttctaag     9900
tcttatgttg tatcgttaag actcatgcaa tttacatttt attccataac tattttagta    9960
ttaaaatttg tcagtgatat ttcttaccct ctcctctagg aaaatgtgcc atgtttatcc   10020
cttggctttg aatgcccctc aggaacagac actaagagtt tgagaagcat ggttacaagg   10080
gtgtggcttc ccctgcggaa actaagtaca gactatttca ctgtaaagca gagaagttct   10140
tttgaaggag aatctccagt gaagaaagag ttcttcactt ttacttccat ttcctcttgt   10200
gggtgaccct caatgctcct tgtaaaactc caatatttta aacatggctg ttttgccttt   10260
ctttgcttct ttttagcatg aatgagacag atgatacttt aaaaagtaa ttaaaaaaa    10320 aaacttgtga aaatacatgg ccataataca gaacccaata caatgatctc ctttaccaaa   10380
ttgttatgtt tgtactttg tagatagctt tccaattcag agacagttat tctgtgtaaa    10440
ggtctgactt aacaagaaaa gatttcccctt tacccaaaga atcccagtcc ttatttgctg  10500
gtcaataagc agggtcccca ggaatggggt aactttcagc accctctaac ccactagtta   10560
ttagtagact aattaagtaa acttatcgca agttgaggaa acttagaacc aactaaaatt   10620
ctgcttttac tgggattttg ttttttcaaa ccagaaacct ttacttaagt tgactactat   10680
taatgaattt tggtctctct tttaagtgct cttcttaaaa atgttatctt actgctgaga   10740
agttcaagtt tgggaagtac aaggaggaat agaaacttaa gagattttct tttagagcct   10800
```

```
cttctgtatt tagccctgta ggattttttt tttttttttt tttttggtg ttgttgagct    10860 tcagtgaggc tattcattca cttatactga taatgtctga gatactgtga atgaaatact    10920
atgtatgctt aaacctaaga ggaaatattt tcccaaaatt attcttcccg aaaaggagga    10980
gttgcctttt gattgagttc ttgcaaatct cacaacgact ttattttgaa caatactgtt    11040
tggggatgat gcattagttt gaaacaactt cagttgtagc tgtcatctga taaaattgct    11100
tcacagggaa ggaaatttaa cacggatcta gtcattattc ttgttagatt gaatgtgtga    11160
attgtaattg taaacaggca tgataattat tactttaaaa actaaaaaca gtgaatagtt    11220
agttgtggag gttactaaag gatggttttt ttttaaataa aactttcagc attatgcaaa    11280
tgggcatatg gcttaggata aaacttccag aagtagcatc acatttaaat tctcaagcaa    11340
cttaataata tggggctctg aaaaactggt taaggttact ccaaaaatgg ccctgggtct    11400
gacaaagatt ctaacttaaa gatgcttatg aagactttga gtaaaatcat ttcataaaat    11460
aagtgaggaa aaacaactag tattaaattc atcttaaata atgtatgatt taaaaaatat    11520
gtttagctaa aaatgcatag tcatttgaca atttcattta tatctcaaaa aatttactta    11580
accaagttgg tcacaaaact gatgagactg gtggtggtag tgaataaatg agggaccatc    11640
catatttgag acactttaca tttgtgatgt gttatactga attttcagtt tgattctata    11700
gactacaaat ttcaaaatta caatttcaag atgtaataag tagtaatatc ttgaaatagc    11760
tctaaaggga atttttctgt tttattgatt cttaaaatat atgtgctgat tttgatttgc    11820
atttgggtag attatacttt tatgagtatg gaggttaggt attgattcaa gttttcctta    11880
cctatttggt aaggatttca aagtcttttt gtgcttggtt ttcctcattt ttaaatatga    11940
aatatattga tgacctttaa caaattttt ttatctcaaa ttttaaagga gatcttttct    12000
aaaagaggca tgatgactta atcattgcat gtaacagtaa acgataaacc aatgattcca    12060
tactctctaa agaataaaag tgagctttag ggccgggcat ggtcagaaat ttgacaccaa    12120
cctggccaac atggcgaaac cccgtctcta ctaaaaatac aaaaatcagc cgggcatggt    12180
ggcggcacct atagtcccag ctacttggga ggatgagaca ggagagtcac ttgaacctgg    12240
gaggagaggt tgcagtgagc tgagatcacg ccattgcact ccagcctgag caatgaaagc    12300
aaaactccat ctcaaaaaaa aaaaagaaa agaaagaata aaagtgagct ttggattgca    12360
tataaatcct ttagacatgt agtagacttg tttgatactg tgtttgaaca aattacgaag    12420
tattttcatc aaagaatgtt attgtttgat gttatttta ttttttattg cccagcttct    12480
ctcatattac gtgattttct tcacttcatg tcactttatt gtgcagggtc agagtattat    12540
tccaatgctt actggagaag tgattcctgt aatggaactg ctttcatcta tgaaatcaca    12600
cagtgttcct gaagaaatag atgtaagttt aaatgagagc aattatacac tttatgagtt    12660 ttttgggggtt atagtattat tatgtatatt attaatattc taattttaat agtaaggact    12720
ttgtcataca tactattcac atacagtatt agccacttta gcaaataagc acacacaaaa    12780
tcctggattt tatggcaaaa cagaggcatt tttgatcagt gatgacaaaa ttaaattcat    12840
tttgtttatt tcattacttt tataattcct aaaagtggga ggatcccagc tcttatagga    12900
gcaattaata tttaatgtag tgtcttttga aacaaaactg tgtgccaaag tagtaaccat    12960
taatggaagt ttacttgtag tcacaaattt agtttcctta atcatttgtt gaggacgttt    13020
tgaatcacac actatgagtg ttaagagata cctttaggaa actattcttg ttgttttctg    13080
attttgtcat ttaggttagt ctcctgattc tgacagctca gaagaggaag ttgttcttgt    13140
aaaaattgtt taacctgctt gaccagcttt cacatttgtt cttctgaagt ttatggtagt    13200
```

```
gcacagagat tgttttttgg ggagtcttga ttctcggaaa tgaaggcagt gtgttatatt   13260
gaatccagac ttccgaaaac ttgtatatta aaagtgttat ttcaacacta tgttacagcc   13320
agactaattt tttttatttt tgatgcattt tagatagctg atacagtact caatgatgat   13380
gatattggtg acagctgtca tgaaggcttt cttctcaagt aagaattttt cttttcataa   13440
aagctggatg aagcagatac catcttatgc tcacctatga caagatttgg aagaaagaaa   13500
ataacagact gtctacttag attgttctag ggacattacg tatttgaact gttgcttaaa   13560
tttgtgttat ttttcactca ttatatttct atatatattt ggtgttattc catttgctat   13620
ttaaagaaac cgagtttcca tcccagacaa gaaatcatgg ccccttgctt gattctggtt   13680
tcttgtttta cttctcatta aagctaacag aatcctttca tattaagttg tactgtagat   13740
gaacttaagt tatttaggcg tagaacaaaa ttattcatat ttatactgat cttttttccat  13800 ccagcagtgg agtttagtac ttaagagttt gtgcccttaa accagactcc ctggattaat   13860
gctgtgtacc cgtgggcaag gtgcctgaat tctctataca cctatttcct catctgtaaa   13920
atggcaataa tagtaatagt acctaatgtg tagggttgtt ataagcattg agtaagataa   13980
ataatataaa gcacttagaa cagtgcctgg aacataaaaa cacttaataa tagctcatag   14040
ctaacatttc ctatttacat ttcttctaga aatagccagt atttgttgag tgcctacatg   14100
ttagttcctt tactagttgc tttacatgta ttatcttata ttctgtttta aagtttcttc   14160
acagttacag attttcatga aatttactt ttaataaaag agaagtaaaa gtataaagta   14220
ttcactttta tgttcacagt cttttccttt aggctcatga tggagtatca gaggcatgag   14280
tgtgtttaac ctaagagcct taatggcttg aatcagaagc actttagtcc tgtatctgtt   14340
cagtgtcagc ctttcataca tcattttaaa tcccatttga ctttaagtaa gtcacttaat   14400
ctctctacat gtcaatttct tcagctataa aatgatggta tttcaataaa taaatacatt   14460
aattaaatga tattatactg actaattggg ctgttttaag gctcaataag aaaatttctg   14520
tgaaaggtct ctagaaaatg taggttccta tacaaataaa agataacatt gtgcttatag   14580
cttcggtgtt tatcatataa agctattctg agttatttga agagctcacc tactttttt   14640 tgtttttagt ttgttaaatt gttttatagg caatgttttt aatctgtttt ctttaactta   14700
cagtgccatc agctcacact tgcaaacctg tggctgttcc gttgtagtag gtagcagtgc   14760
agagaaagta aataaggtag tttatttat aatctagcaa atgatttgac tctttaagac   14820
tgatgatata tcatggattg tcatttaaat ggtaggttgc aattaaaatg atctagtagt   14880
ataaggaggc aatgtaatct catcaaattg ctaagacacc ttgtggcaac agtgagtttg   14940
aaataaactg agtaagaatc atttatcagt ttattttgat agctcggaaa taccagtgtc   15000
agtagtgtat aaatggtttt gagaatatat taaaatcaga tatataaaaa aaattactct   15060
tctatttccc aatgttatct ttaacaaatc tgaagatagt catgtacttt tggtagtagt   15120
tccaaagaaa tgttatttgt ttattcatct tgatttcatt gtcttcgctt tccttctaaa   15180
tctgtccctt ctagggagct attgggatta agtggtcatt gattattata ctttattcag   15240
taatgtttct gacccttcc ttcagtgcta cttgagttaa ttaaggatta atgaacagtt   15300
acatttccaa gcattagcta ataaactaaa ggattttgca cttttcttca ctgaccatta   15360
gttagaaaga gttcagagat aagtatgtgt atctttcaat ttcagcaaac ctaattttt   15420 aaaaaaagtt ttacatagga aatatgtggg aaatgatact ttacaaagat attcataatt   15480 ttttttttgta atcagctact ttgtatattt acatgagcct taatttatat ttctcatata   15540
```

```
accatttatg agagcttagt atacctgtgt cattatattg catctacgaa ctagtgacct    15600
tattccttct gttacctcaa acaggtggct ttccatctgt gatctccaaa gccttaggtt    15660
gcacagagtg actgccgagc tgctttatga agggagaaag gctccatagt tggagtgttt    15720
tttttttttt ttttaaacat ttttcccatc ctccatcctc ttgagggaga atagcttacc    15780
ttttatcttg ttttaatttg agaaagaagt tgccaccact ctaggttgaa aaccactcct    15840
ttaacataat aactgtggat atggtttgaa tttcaagata gttacatgcc ttttttatttt   15900 tcctaataga gctgtaggtc aaatattatt agaatcagat ttctaaatcc cacccaatga    15960
cctgcttatt ttaaatcaaa ttcaataatt aattctcttc tttttggagg atctggacat    16020
tctttgatat ttcttacaac gaatttcatg tgtagaccca ctaaacagaa gctataaaag    16080
ttgcatggtc aaataagtct gagaaagtct gcagatgata taattcacct gaagagtcac    16140
agtatgtagc caaatgttaa aggttttgag atgccataca gtaaatttac caagcatttt    16200
ctaaatttat ttgaccacag aatccctatt ttaagcaaca actgttacat cccatggatt    16260
ccaggtgact aaagaatact tatttcttag gatatgtttt attgataata acaattaaaa    16320
tttcagatat ctttcataag caaatcagtg gtcttttttac ttcatgtttt aatgctaaaa   16380
tattttcttt tatagatagt cagaacatta tgccttttttc tgactccagc agagagaaaa   16440
tgctccaggt tatgtgaagc agaatcatca tttaaatatg agtcagggct ctttgtacaa    16500
ggcctgctaa aggtatagtt tctagttatc acaagtgaaa ccacttttct aaaatcattt    16560
ttgagactct ttatagacaa atcttaaata ttagcattta atgtatctca tattgacatg    16620
cccagagact gacttccttt acacagttct gcacatagac tatatgtctt atggatttat    16680
agttagtatc atcagtgaaa caccatagaa tacccttttgt gttccaggtg ggtccctgtt   16740
cctacatgtc tagcctcagg actttttttt tttttaacaca tgcttaaatc aggttgcaca    16800
tcaaaaataa gatcatttct ttttaactaa atagatttga attttattga aaaaaaattt    16860
taaacatctt taagaagctt ataggattta agcaattcct atgtatgtgt actaaaatat    16920
atatatttct atatataata tatattagaa aaaaattgta tttttctttt atttgagtct    16980
actgtcaagg agcaaaacag agaaatgtaa attagcaatt atttataata cttaaaggga    17040
agaaagttgt tcaccttgtt gaatctatta ttgttatttc aattatagtc ccaagacgtg    17100
aagaaatagc tttcctaatg gttatgtgat tgtctcatag tgactacttt cttgaggatg    17160
tagccacggc aaaatgaaat aaaaaaattt aaaaattgtt gcaaatacaa gttatattag    17220
gcttttgtgc atttttcaata atgtgctgct atgaactcag aatgatagta tttaaatata    17280
gaaactagtt aaaggaaacg tagtttctat ttgagttata catatctgta aattagaact    17340
tctcctgtta aaggcataat aaagtgctta atacttttgt ttcctcagca ccctctcatt    17400
taattatata attttagttc tgaaagggac ctataccaga tgcctagagg aaatttcaaa    17460
actatgatct aatgaaaaaa tatttaatag ttctccatgc aaatacaaat catatagttt    17520
tccagaaaat acctttgaca ttatacaaag atgattatca cagcattata atagtaaaaa    17580
aatggaaata gcctctttct tctgttctgt tcatagcaca gtgcctcata cgcagtaggt    17640
tattattaca tggtaactgg ctaccccaac tgattaggaa agaagtaaat ttgttttata    17700
aaaatacata ctcattgagg tgcatagaat aattaagaaa ttaaaagaca cttgtaattt    17760
tgaatccagt gaatacccac tgttaatatt tggtatatct cttttctagtc ttttttttccc   17820 ttttgcatgt attttcttta agactcccac ccccactgga tcatctctgc atgttctaat    17880
ctgctttttt cacagcagat tctaagcctc tttgaatatc aacacaaact tcaacaactt    17940
```

```
catctataga tgccaaataa taaattcatt tttatttact taaccacttc ctttggatgc    18000
ttaggtcatt ctgatgtttt gctattgaaa ccaatgctat actgaacact tctgtcacta    18060
aaactttgca cacactcatg aatagcttct taggataaat ttttagagat ggatttgcta    18120
aatcagagac cattttttaa aattaaaaaa caattattca tatcgtttgg catgtaagac    18180
agtaaatttt ccttttattt tgacaggatt caactggaag ctttgtgctg cctttccggc    18240
aagtcatgta tgctccatat cccaccacac acatagatgt ggatgtcaat actgtgaagc    18300
agatgccacc ctgtcatgaa catatttata atcagcgtag atacatgaga tccgagctga    18360
cagccttctg gagagccact tcagaagaag acatggctca ggatacgatc atctacactg    18420
acgaaagctt tactcctgat ttgtacgtaa tgctctgcct gctggtactg tagtcaagca    18480
atatgaaatt gtgtctttta cgaataaaaa caaaacagaa gttgcattta aaagaaaga    18540 aatattacca gcagaattat gcttgaagaa acatttaatc aagcattttt ttcttaaatg    18600
ttcttctttt tccatacaat tgtgtttacc ctaaaatagg taagattaac ccttaaagta    18660
aatatttaac tatttgttta ataaatatat attgagctcc taggcactgt tctaggtacc    18720
gggcttaata gtgccaacc agacagcccc agccccagcc cctacattgt gtatagtcta    18780
ttatgtaaca gttattgaat ggacttatta acaaaaccaa agaagtaatt ctaagtcttt    18840
tttttcttga catatgaata taaaatacag caaaactgtt aaaatatatt aatgaacat    18900 ttttttactt tgcattttat attgttattc acttcttatt ttttttttaaa aaaaaaagcc    18960 tgaacagtaa attcaaaagg aaagtaatg ataattaatt gttgagcatg gacccaactt    19020
gaaaaaaaaa atgatgatga taaatctata atcctaaaac cctaagtaaa cacttaaaag    19080
atgttctgaa atcaggaaaa gaattatagt atacttttgt gtttctcttt tatcagttga    19140
aaaaaggcac agtagctcat gcctgtaaga acagagcttt gggagtgcaa ggcaggcgga    19200
tcacttgagg ccaggagttc cagaccagcc tgggcaacat agtgaaaccc catctctaca    19260
aaaaataaaa aagaattatt ggaatgtgtt tctgtgtgcc tgtaatccta gctattccga    19320
aagctgaggc aggaggatct tttgagccca ggagtttgag gttacaggga gttatgatgt    19380
gccagtgtac tccagcctgg ggaacaccga gactctgtct tatttaaaaa aaaaaaaaaa    19440
aaaatgcttg caataatgcc tggcacatag aaggtaacag taagtgttaa ctgtaataac    19500
ccaggtctaa gtgtgtaagg caatagaaaa attggggcaa ataagcctga cctatgtatc    19560
tacagaatca gtttgagctt aggtaacaga cctgtggagc accagtaatt acacagtaag    19620
tgttaaccaa aagcatagaa taggaatatc ttgttcaagg gacccccagc cttatacatc    19680
tcaaggtgca gaaagatgac ttaatatagg acccattttt tcctagttct ccagagtttt    19740
tattggttct tgagaaagta gtaggggaat gttttagaaa atgaattggt ccaactgaaa    19800
ttacatgtca gtaagttttt atatattggt aaattttagt agacatgtag aagttttcta    19860
attaatctgt gccttgaaac attttctttt ttcctaaagt gcttagtatt ttttccgttt    19920
tttgattggt tacttgggag cttttttgag gaaatttagt gaactgcaga atgggtttgc    19980
aaccatttgg tattttgtt ttgtttttta gaggatgtat gtgtatttta acatttctta    20040 atcatttta gccagctatg tttgttttgc tgatttgaca aactacagtt agacagctat    20100
tctcattttg ctgatcatga caaaataata tcctgaattt ttaaattttg catccagctc    20160
taaattttct aaacataaaa ttgtccaaaa aatagtattt tcagccacta gattgtgtgt    20220
taagtctatt gtcacagagt catttttactt ttaagtatat gttttttacat gttaattatg    20280
```

```
tttgttatttt ttaatttttaa cttttttaaaa taattccagt cactgccaat acatgaaaaa    20340
ttggtcactg gaattttttt tttgactttt attttaggtt catgtgtaca tgtgcaggtg    20400
tgttatacag gtaaattgcg tgtcatgagg gtttggtgta caggtgattt cattacccag    20460
gtaataagca tagtacccaa taggtagttt tttgatcctc acccttctcc caccctcaag    20520
taggccctgg tgttgctgtt tccttctttg tgtccatgta tactcagtgt ttagctccca    20580
cttagaagtg agaacatgcg gtagttggtt ttctgttcct ggattagttc acttaggata    20640
atgacctcta gctccatctg gttttatgg ctgcatagta ttccatggtg tatatgtatc    20700
acattttctt tatccagtct accattgata ggcatttagg ttgattccct gtctttgtta    20760
tcatgaatag tgctgtgatg aacatacaca tgcatgtgtc tttatggtag aaaaatttgt    20820
attcctttag gtacatatag aataatgggg ttgctagggt gaatggtagt tctattttca    20880
gttatttgag aaatcttcaa actgcttttc ataatagcta aactaattta cagtcccgcc    20940
agcagtgtat aagtgttccc ttttctccac aaccttgcca acatctgtga ttttttgact    21000
ttttaataat agccattcct agagaattga tttgcaattc tctattagtg atattaagca    21060
ttttttcata tgcttttag ctgtctgtat atattcttct gaaaaatttt catgtccttt    21120
gcccagtttg tagtggggtg ggttgttttt tgcttgttaa ttagttttaa gttccttcca    21180
gattctgcat atcccttgt tggatacatg gtttgcagat attttctcc cattgtgtag    21240 gttgtctttt actctgttga tagtttcttt tgccatgcag gagctcgtta ggtcccattt    21300
gtgtttgttt ttgttgcagt tgcttttggc gtcttcatca taaaatctgt gccagggcct    21360
atgtccagaa tggtatttcc taggttgtct tccagggttt ttacaatttt agattttacg    21420
tttatgtctt taatccatct tgagttgatt tttgtatatg gcacaaggaa ggggtccagt    21480
ttcactccaa ttcctatggc tagcaattat cccagcacca tttattgaat acggagtcct    21540
ttccccattg cttgttttt gtcaactttg ttgaagatca gatggttgta agtgtgtggc    21600
tttatttctt ggctctctat tctccattgg tctatgtgtc tgttttata acagtaccct    21660 gctgttcagg ttcctatagc cttttagtat aaaatcggct aatgtgatgc ctccagcttt    21720 gttcttttg cttaggattg cttggctat ttgggctcct ttttgggtcc atattaattt    21780
taaaacagtt ttttctggtt ttgtgaagga tatcattggt agtttatagg aatagcattg    21840
aatctgtaga ttgctttggg cagtatggcc atttaacaa tattaattct tcctatctat    21900
gaatatggaa tgttttttcca tgtgtttgtg tcatctcttt atacctgatg tataaagaaa    21960
agctggtatt attcctactc aatctgttcc aaaaaattga ggaggaggaa ctcttcccta    22020
atgaggccag catcattctg ataccaaaac ctggcagaga cacaacagaa aaagaaaac    22080 ttcaggccaa tatccttgat gaatatagat gcaaaatcc tcaacaaaat actagcaaac    22140
caaatccagc agcacatcaa aaagctgatc tactttgatc aagtaggctt tatccctggg    22200
atgcaaggtt ggttcaacat acacaaatca ataagtgtga ttcatcacat aaacagagct    22260
aaaaacaaaa accacaagat tatctcaata ggtagagaaa aggttgtcaa taaaatttaa    22320
catcctccat gttaaaaacc ttcagtaggt caggtgtagt gactcacacc tgtaatccca    22380
gcactttggg aggccaaggc gggcatatct cttaagccca ggagttcaag acgagcctag    22440
gcagcatggt gaaaccccat ctctacaaaa aaaaaaaaa aaaaaaatta gcttggtatg    22500
gtgacatgca cctatagtcc cagctattca ggaggttgag gtgggaggat tgtttgagcc    22560
cgggaggcag aggttggcag cgagctgaga tcatgccacc gcactccagc ctgggcaacg    22620
gagtgagacc ctgtctcaaa aaagaaaaat cacaaacaat cctaaacaaa ctaggcattg    22680
```

```
aaggaacatg cctcaaaaaa ataagaacca tctatgacag acccatagcc aatatcttac    22740
caaatgggca aaagctggaa gtattctcct tgagaaccgt aacaagacaa ggatgtccac    22800
tctcaccact ccttttcagc atagttctgg aagtcctagc cagagcaatc aggaaagaga    22860
aagaaagaaa gacattcaga taggaagaga agaagtcaaa ctatttctgt ttgcaggcag    22920
tataattctg tacctagaaa atctcatagt ctctgcccag aaactcctaa atctgttaaa    22980
aatttcagca aagttttggc attctctata ctccaacacc ttccaaagtg agagcaaaat    23040
caagaacaca gtcccattca caatagccgc aaaacgaata aaatacctag gaatccagct    23100
aaccagggag gtgaaagatc tctatgagaa ttacaaaaca ctgctgaaag aaatcagaga    23160
tgacacaaac aaatggaaat gttctttttt aacaccttgc tttatctaat tcacttatga    23220
tgaagatact cattcagtgg aacaggtata ataagtccac tcgattaaat ataagcctta    23280
ttctctttcc agagcccaag aagggcact atcagtgccc agtcaataat gacgaaatgc     23340
taatattttt cccctttacg gtttctttct tctgtagtgt ggtacactcg tttcttaaga    23400
taaggaaact tgaactacct tcctgtttgc ttctacacat acccattctc ttttttttgcc   23460 actctggtca ggtataggat gatccctacc actttcagtt aaaaactcct cctcttacta    23520
aatgttctct taccctctgg cctgagtaga acctagggaa aatggaagag aaaaagatga    23580
aagggaggtg gggcctggga agggaataag tagtcctgtt tgtttgtgtg tttgctttag    23640
cacctgctat atcctaggtg ctgtgttagg cacacattat tttaagtggc cattatatta    23700
ctactactca ctctggtcgt tgccaaggta ggtagtactt tcttggatag ttggttcatg    23760
ttacttacag atggtgggct tgttgaggca aacccagtgg ataatcatcg gagtgtgttc    23820
tctaatctca ctcaaatttt tcttcacatt ttttggtttg ttttggtttt tgatggtagt    23880
ggcttatttt tgttgctggt ttgttttttg ttttttttg agatggcaag aattggtagt     23940
tttatttatt aattgcctaa gggtctctac ttttttttaaa agatgagagt agtaaaatag   24000
attgatagat acatacatac ccttactggg gactgcttat attctttaga gaaaaaatta    24060
catattagcc tgacaaacac cagtaaaatg taaatatatc cttgagtaaa taaatgaatg    24120
tatattttgt gtctccaaat atatatatct atattcttac aaatgtgttt atatgtaata    24180
tcaatttata agaacttaaa atgttggctc aagtgaggga ttgtggaagg tagcattata    24240
tggccatttc aacatttgaa cttttttctt ttcttcattt tcttcttttc ttcaggaata    24300
tttttcaaga tgtcttacac agagacactc tagtgaaagc cttcctggat caggtaaatg    24360
ttgaacttga gattgtcaga gtgaatgata tgacatgttt tctttttttaa tatatcctac   24420 aatgcctgtt ctatatattt atattcccct ggatcatgcc ccagagttct gctcagcaat    24480
tgcagttaag ttagttacac tacagttctc agaagagtct gtgagggcat gtcaagtgca    24540
tcattacatt ggttgcctct tgtcctagat ttatgcttcg ggaattcaga cctttgttta    24600
caatataata aatattattg ctatcttttta aagatataat aataagatat aaagttgacc   24660
acaactactg ttttttgaaa catagaattc ctggtttaca tgtatcaaag tgaaatctga    24720
cttagctttt acagatataa tatatacata tatatatcct gcaatgcttg tactatatat    24780
gtagtacaag tatatatata tgtttgtgtg tgtatatata tatagtacga gcatatatac    24840
atattaccag cattgtagga tatatatatg tttatatatt aaaaaaaagt tataaactta    24900
aaaccctatt atgttatgta gagtatatgt tatatatgat atgtaaaata tataacatat    24960
actctatgat agagtgtaat atattttta tatatattt aacatttata aaatgataga      25020
```

```
attaagaatt gagtcctaat ctgttttatt aggtgctttt tgtagtgtct ggtctttcta    25080
aagtgtctaa atgattttc cttttgactt attaatgggg aagagcctgt atattaacaa    25140
ttaagagtgc agcattccat acgtcaaaca acaaacattt taattcaagc attaacctat    25200
aacaagtaag tttttttttt tttttttgaga aagggaggtt gtttatttgc ctgaaatgac    25260 tcaaaatat ttttgaaaca tagtgtactt atttaaataa catctttatt gtttcattct    25320
tttaaaaaat atctacttaa ttacacagtt gaaggaaatc gtagattata tggaacttat    25380
ttcttaatat attacagttt gttataataa cattctgggg atcaggccag gaaactgtgt    25440
catagataaa gctttgaaat aatgagatcc ttatgtttac tagaaatttt ggattgagat    25500
ctatgaggtc tgtgacatat tgcgaagttc aaggaaaatt cgtaggcctg gaatttcatg    25560
cttctcaagc tgacataaaa tccctcccac tctccacctc atcatatgca cacattctac    25620
tcctacccac ccactccacc ccctgcaaaa gtacaggtat atgaatgtct caaaaccata    25680
ggctcatctt ctaggagctt caatgttatt tgaagatttg ggcagaaaaa attaagtaat    25740
acgaaataac ttatgtatga gttttaaaag tgaagtaaac atggatgtat tctgaagtag    25800
aatgcaaaat ttgaatgcat ttttaaagat aaattagaaa acttctaaaa actgtcagat    25860
tgtctgggcc tggtggctta tgcctgtaat cccagcactt tgggagtccg aggtgggtgg    25920
atcacaaggt caggagatcg agaccatcct gccaacatgg tgaaacccg tctctactaa    25980 gtatacaaaa attagctggg cgtggcagcg tgtgcctgta atcccagcta cctgggaggc    26040
tgaggcagga gaatcgcttg aacccaggag gtgtaggttg cagtgagtca agatcgcgcc    26100
actgcacttt agcctggtga cagagctaga ctccgtctca aaaaaaaaa aaaatatcag    26160 attgttccta cacctagtgc ttctatacca cactcctgtt aggggcatc agtggaaatg    26220 gttaaggaga tgtttagtgt gtattgtctg ccaagcactg tcaacactgt catagaaact    26280
tctgtacgag tagaatgtga gcaaattatg tgttgaaatg gttcctctcc ctgcaggtct    26340
ttcagctgaa acctggctta tctctcagaa gtactttcct tgcacagttt ctacttgtcc    26400
ttcacagaaa agccttgaca ctaataaaat atatagaaga cgatacgtga gtaaaactcc    26460
tacacggaag aaaaaccttt gtacattgtt ttttgtttt gttccttg tacattttct    26520 atatcataat ttttgcgctt cttttttttt ttttttttt ttttttcca ttattttag    26580 gcagaaggga aaaagccct ttaaatctct tcggaacctg aagatagacc ttgatttaac    26640
agcagagggc gatcttaaca taataatggc tctggctgag aaaattaaac caggcctaca    26700 ctctttatc tttggaagac cttctacac tagtgtgcaa gaacgagatg ttctaatgac    26760 ttttaaatg tgtaacttaa taagcctatt ccatcacaat catgatcgct ggtaaagtag    26820
ctcagtggtg tggggaaacg ttcccctgga tcatactcca gaattctgct ctcagcaatt    26880
gcagttaagt aagttacact acagttctca caagagcctg tgaggggatg tcaggtgcat    26940
cattacattg ggtgtctctt ttcctagatt tatgcttttg ggatacagac ctatgtttac    27000
aatataataa atattattgc tatcttttaa agatataata ataggatgta aacttgacca    27060
caactactgt ttttttgaaa tacatgattc atggtttaca tgtgtcaagg tgaaatctga    27120
gttggctttt acagatagtt gactttctat cttttggcat tctttggtgt gtagaattac    27180
tgtaatactt ctgcaatcaa ctgaaaacta gagcctttaa atgatttcaa ttccacagaa    27240
agaaagtgag cttgaacata ggatgagctt tagaaagaaa attgatcaag cagatgttta    27300
attggaattg attattagat cctacttgt ggatttagtc cctgggattc agtctgtaga    27360
aatgtctaat agttctctat agtccttgtt cctggtgaac cacagttagg gtgttttgtt    27420
```

```
tattttattg ttcttgctat tgttgatatt ctatgtagtt gagctctgta aaaggaaatt   27480
gtattttatg ttttagtaat tgttgccaac ttttttaaatt aatttttcatt atttttgagc   27540 caaattgaaa tgtgcacctc ctgtgccttt tttctcctta gaaatctaa ttacttggaa   27600 caagttcaga tttcactggt cagtcatttt catcttgttt tcttcttgct aagtcttacc   27660
atgtacctgc tttggcaatc attgcaactc tgagattata aaatgcctta gagaatatac   27720
taactaataa gatcttttttt tcagaaacag aaaatagttc cttgagtact tccttcttgc   27780
atttctgcct atgttttga agttgttgct gtttgcctgc aataggctat aaggaatagc   27840
aggagaaatt ttactgaagt gctgttttcc taggtgctac tttggcagag ctaagttatc   27900
ttttgttttc ttaatgcgtt tggaccattt tgctggctat aaaataactg attaatataa   27960
ttctaacaca atgttgacat tgtagttaca caaacacaaa taaatatttt atttaaaatt   28020
ctggaagtaa tataaaaggg aaaatatatt tataagaaag ggataaaggt aatagagccc   28080
ttctgccccc cacccaccaa atttacacaa caaaatgaca tgttcgaatg tgaaaggtca   28140
taatagcttt cccatcatga atcagaaaga tgtggacagc ttgatgtttt agacaaccac   28200
tgaactagat gactgttgta ctgtagctca gtcatttaaa aaatatataa atactacctt   28260
gtagtgtccc atactgtgtt ttttacatgg tagattctta tttaagtgct aactggttat   28320
tttctttggc tggtttattg tactgttata cagaatgtaa gttgtacagt gaaataagtt   28380
attaaagcat gtgtaaacat tgttatatat cttttctcct aaatggagaa ttttgaataa   28440
aatatatttg aaattttgcc tctttcagtt gttcattcag aaaaaaatac tatgatattt   28500
gaagactgat cagcttctgt tcagctgaca gtcatgctgg atctaaactt ttttttaaaat   28560 taattttgtc ttttcaaaga aaaaatattt aaagaagctt tataatataa tcttatgtta   28620
aaaaaacttt ctgcttaact ctctggattt cattttgatt tttcaaatta tatattaata   28680
tttcaaatgt aaaatactat ttagataaat tgttttttaaa cattcttatt attataaaat   28740
taatataacc taaactgaag ttattcatcc caggtatcta atacatgtat ccaaagtaaa   28800
aatccaagga atctgaacac tttcatctgc aaagctagga ataggtttga cattttcact   28860
ccaagaaaaa gttttttttt gaaaatagaa tagttgggat gagaggtttc tttaaaagaa   28920
gactaactga tcacattact atgattctca aagaagaaac caaaacttca tataatacta   28980
taaagtaaat ataaaatagt tccttctata gtatatttct ataatgctac agtttaaaca   29040
gatcactctt atataactact attttgattt tgatgtagaa ttgcacaaat tgatatttct   29100
cctatgatct gcagggtata gcttaaagta acaaaaacag tcaaccacct ccatttaaca   29160
cacagtaaca ctatgggact agttttatta cttccatttt acaaatgagg aaactaaagc   29220
ttaaagatgt gtaatacacc gcccaaggtc acacagctgg taaaggtgga tttcatccca   29280
gacagttaca gtcattgcca tgggcacagc tcctaactta gtaactccat gtaactggta   29340
ctcagtgtag ctgaattgaa aggagagtaa ggaagcaggt tttacaggtc tacttgcact   29400
attcagagcc cgagtgtgaa tccctgctgt gctgcttgga gaagttactt aacctatgca   29460
aggttcattt tgtaaatatt ggaaatggag tgataatacg tacttcacca gaggatttaa   29520
tgagacctta tacgatcctt agttcagtac ctgactagtg cttcataaat gcttttcat   29580 ccaatctgac aatctccagc ttgtaattgg ggcatttaga acatttaata tgattattgg   29640
catggtaggt taaagctgtc atcttgctgt tttctatttg ttcttttgt tttctcctta   29700 cttttggatt tttttattct actatgtctt ttctattgtc ttattaacta tactctttga   29760
```

-continued

```
tttattttag tggttgtttt agggttatac ctctttctaa tttaccagtt tataaccagt   29820
ttatatacta cttgacatat agcttaagaa acttactgtt gttgtctttt tgctgttatg   29880
gtcttaacgt ttttatttct acaaacatta taaactccac actttattgt ttttttaattt  29940 tacttataca gtcaattatc ttttaaagat atttaaatat aaacattcaa aacaccccaa   30000
t                                                                  30001

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
tggccccggc ccggcccca a                                              21

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
tcggccccgg ccccggccca a                                             21

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
tccggccccg gccccggcca a                                             21

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
tcccggcccc ggccccggca a                                             21

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
tccccggccc cggccccgga a                                             21

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
```
tgccccggcc ccggccccga a                                              21

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
tggccccgac cccggcccca a                                              21

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
tcggccccag ccccggccca a                                              21

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10
tccggcccag gccccggcca a                                              21

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
tcccggccac ggccccggca a                                              21

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
tccccggcac cggccccgga a                                              21

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
tgccccggac ccggccccga a                                              21

<210> SEQ ID NO 14
<211> LENGTH: 21
<212> TYPE: DNA

```
<213> ORGANISM: Artificial sequence
<220> FEATURE:
<223> OTHER INFORMATION: Synthetic oligonucleotide

<400> SEQUENCE: 14
tggccccgac cccagcccca a                                          21

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15
tcggccccag cccaggccca a                                          21

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 16
tccggcccag gccacggcca a                                          21

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
tcccggccac ggcaccggca a                                          21

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
tccccggcac cggacccgga a                                          21

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
tgccccggac ccgaccccga a                                          21

<210> SEQ ID NO 20
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 20
tggccccgaa accggcccca a                                          21
```

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
tcggccccaa acccggccca a                                                  21

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
tccggcccaa accccggcca a                                                  21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
tcccggccaa agccccggca a                                                  21

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24
tccccggcaa aggccccgga a                                                  21

<210> SEQ ID NO 25
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 25
tgccccggaa acggccccga a                                                  21

<210> SEQ ID NO 26
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 26
tggggccggg gccggggcca a                                                  21

<210> SEQ ID NO 27
<211> LENGTH: 21
<212> TYPE: DNA
<213> ORGANISM: Artificial sequence
<220> FEATURE:

<223> OTHER INFORMATION: Synthetic oligonucleotide

<400> SEQUENCE: 27
tcggggccgg ggccggggca a                                              21

<210> SEQ ID NO 28
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 28
tccggggccg gggccgggga a                                              21

<210> SEQ ID NO 29
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 29
tgccggggcc ggggccggga a                                              21

<210> SEQ ID NO 30
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 30
tggccggggc cggggccgga a                                              21

<210> SEQ ID NO 31
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 31
tgggccgggg ccggggccga a                                              21

<210> SEQ ID NO 32
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 32
tggggccgag gccggggcca a                                              21

<210> SEQ ID NO 33
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 33
tcggggccag ggccggggca a                                              21

```
<210> SEQ ID NO 34
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 34
tccggggcag gggccgggga a                                              21

<210> SEQ ID NO 35
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 35
tgccggggac ggggccggga a                                              21

<210> SEQ ID NO 36
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 36
tggccgggac cggggccgga a                                              21

<210> SEQ ID NO 37
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 37
tgggccggag ccggggccga a                                              21

<210> SEQ ID NO 38
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 38
tggggccgag gccagggcca a                                              21

<210> SEQ ID NO 39
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 39
tcggggccag ggcaggggca a                                              21

<210> SEQ ID NO 40
<211> LENGTH: 21
<212> TYPE: DNA
<213> ORGANISM: Artificial sequence
<220> FEATURE:
<223> OTHER INFORMATION: Synthetic oligonucleotide
```

```
<400> SEQUENCE: 40
tccggggcag gggacgggga a                                          21

<210> SEQ ID NO 41
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 41
tgccggggac gggaccggga a                                          21

<210> SEQ ID NO 42
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 42
tggccgggac cggagccgga a                                          21

<210> SEQ ID NO 43
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 43
tgggccggag ccgaggccga a                                          21

<210> SEQ ID NO 44
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 44
tggggccgaa accggggcca a                                          21

<210> SEQ ID NO 45
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 45
tcggggccaa agccggggca a                                          21

<210> SEQ ID NO 46
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 46
tccggggcaa aggccgggga a                                          21

<210> SEQ ID NO 47
<211> LENGTH: 21
```

-continued

<212> TYPE: DNA
<213> ORGANISM: Artificial sequence
<220> FEATURE:
<223> OTHER INFORMATION: Synthetic oligonucleotide

<400> SEQUENCE: 47 tgccgggaa agggccggga a                                    21

<210> SEQ ID NO 48
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 48
tggccgggaa aggggccgga a                                   21

<210> SEQ ID NO 49
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 49
tgggccggaa acggggccga a                                   21

<210> SEQ ID NO 50
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 50
tcugcugcaa augcugcuga a                                   21

<210> SEQ ID NO 51
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: n is a, c, g, or t

<400> SEQUENCE: 51
nnnnnnnnnn nnnnnnnnnn n                                   21

<210> SEQ ID NO 52
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 52
taacuucagg gucagcuuga a                                          21

<210> SEQ ID NO 53
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 53
cggccccgaa accggcccct t                                          21

<210> SEQ ID NO 54
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 54
gcuauaccag cgucgucaut t                                          21

<210> SEQ ID NO 55
<211> LENGTH: 22
<212> TYPE: DNA
<213> ORGANISM: Artificial sequence
<220> FEATURE:
<223> OTHER INFORMATION: primer

<400> SEQUENCE: 55
agaaggcaca gagagaatgg aa                                         22

<210> SEQ ID NO 56
<211> LENGTH: 26
<212> TYPE: DNA
<213> ORGANISM: Artificial sequence
<220> FEATURE:
<223> OTHER INFORMATION: primer

<400> SEQUENCE: 56
tcatcatcat tgagtactgt atcagc                                     26

<210> SEQ ID NO 57
<211> LENGTH: 23
<212> TYPE: DNA
<213> ORGANISM: Artificial sequence
<220> FEATURE:
<223> OTHER INFORMATION: primer

<400> SEQUENCE: 57
acgcctgcac aatttcagcc caa                                        23

<210> SEQ ID NO 58
<211> LENGTH: 24
<212> TYPE: DNA
<213> ORGANISM: Artificial sequence
<220> FEATURE:
<223> OTHER INFORMATION: primer

<400> SEQUENCE: 58

```
caagtctgtg tcatctcgga gctg                                    24

<210> SEQ ID NO 59
<211> LENGTH: 23
<212> TYPE: DNA
<213> ORGANISM: Artificial sequence
<220> FEATURE:
<223> OTHER INFORMATION: primer

<400> SEQUENCE: 59
gtcatcaatg gaaatcccat cac                                     23

<210> SEQ ID NO 60
<211> LENGTH: 20
<212> TYPE: DNA
<213> ORGANISM: Artificial sequence
<220> FEATURE:
<223> OTHER INFORMATION: primer

<400> SEQUENCE: 60
ttctccatgg tggtgaagac                                         20
```